US012580044B1

(12) United States Patent
McDonnell

(10) Patent No.: US 12,580,044 B1
(45) Date of Patent: Mar. 17, 2026

(54) SYSTEMS AND METHODS FOR IDENTIFYING CELLS THAT ARE ANTIGEN-SPECIFIC FOR AN IMMUNOGENIC FEATURE

(71) Applicant: 10X Genomics, Inc., Pleasanton, CA (US)

(72) Inventor: Wyatt J. McDonnell, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 247 days.

(21) Appl. No.: 17/464,561

(22) Filed: Sep. 1, 2021

Related U.S. Application Data

(60) Provisional application No. 63/073,830, filed on Sep. 2, 2020.

(51) Int. Cl.
| | |
|---|---|
| *G16B 25/10* | (2019.01) |
| *C12Q 1/6881* | (2018.01) |
| *G16B 20/20* | (2019.01) |

(52) U.S. Cl.
CPC ........... *G16B 25/10* (2019.02); *C12Q 1/6881* (2013.01); *G16B 20/20* (2019.02)

(58) Field of Classification Search
USPC ........................................................ 702/19
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |

(Continued)

FOREIGN PATENT DOCUMENTS

| | | | |
|---|---|---|---|
| EP | 1336662 A2 | 8/2003 | |
| WO | WO 2000/063437 A2 | 10/2000 | |

(Continued)

OTHER PUBLICATIONS

Liu, Peng, et al. "Recent advances in computer-assisted algorithms for cell subtype identification of cytometry data." Frontiers in cell and developmental biology 8 (2020): 234. (Year: 2020).*

(Continued)

*Primary Examiner* — Larry D Riggs, II
*Assistant Examiner* — EMilie A Neulen

(57) ABSTRACT

Systems and methods of identifying antigen-specific cells include obtaining a representation, for each respective immunogenic feature in a plurality of features, of a corresponding count of the respective feature bound to each immune cell in a population of cells. The immune cells are clustered using the representation to identify a plurality of clusters, each including a different subset of the plurality of cells. The total number of unique clonotypes and the total number of clonotypes detected within the subset of cells represented by a particular cluster is determined. This total number of unique clonotypes and total number of clonotypes are used, together with a distribution of a corresponding count of a first immunogenic feature bound to each cell within the subset of cells represented by a particular cluster, to determine whether the subset of cells represented by the respective cluster is antigen-specific for the first immunogenic feature.

25 Claims, 47 Drawing Sheets

(56) References Cited

U.S. PATENT DOCUMENTS

| | | |
|---|---|---|
| 4,800,159 A | 1/1989 | Mullis et al. |
| 4,965,188 A | 10/1990 | Mullis et al. |
| 5,472,881 A | 12/1995 | Beebe et al. |
| 5,512,462 A | 4/1996 | Cheng et al. |
| 5,599,675 A | 2/1997 | Brenner |
| 5,610,287 A | 3/1997 | Nikiforov et al. |
| 5,807,522 A | 9/1998 | Shalon et al. |
| 5,837,860 A | 11/1998 | Anderson et al. |
| 5,919,626 A | 7/1999 | Shi et al. |
| 6,172,218 B1 | 1/2001 | Brenner |
| 6,210,891 B1 | 4/2001 | Nyren et al. |
| 6,258,568 B1 | 7/2001 | Nyren |
| 6,265,552 B1 | 7/2001 | Schatz |
| 6,266,459 B1 | 7/2001 | Walt et al. |
| 6,274,320 B1 | 8/2001 | Rotherbert et al. |
| 6,306,597 B1 | 10/2001 | Macevicz |
| 6,355,431 B1 | 3/2002 | Chee et al. |
| 6,391,937 B1 | 5/2002 | Beuhler et al. |
| 6,737,236 B1 | 5/2004 | Pieken et al. |
| 6,770,441 B2 | 8/2004 | Dickinson et al. |
| 6,859,570 B2 | 2/2005 | Walt et al. |
| 6,867,028 B2 | 3/2005 | Janulaitis et al. |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,259,258 B2 | 8/2007 | Kozlov et al. |
| 7,375,234 B2 | 5/2008 | Sharpless et al. |
| 7,427,678 B2 | 9/2008 | Pieken et al. |
| 7,709,198 B2 | 5/2010 | Luo et al. |
| 8,460,865 B2 | 6/2013 | Chee et al. |
| 8,604,182 B2 | 12/2013 | Luo et al. |
| 8,951,726 B2 | 2/2015 | Luo et al. |
| 9,012,390 B2 | 4/2015 | Holtze et al. |
| 9,512,422 B2 | 12/2016 | Barnard et al. |
| 9,694,361 B2 | 7/2017 | Bharadwaj et al. |
| 9,727,810 B2 | 8/2017 | Fodor et al. |
| 9,783,841 B2 | 10/2017 | Nolan et al. |
| 9,889,422 B2 | 2/2018 | Smith et al. |
| 10,002,316 B2 | 6/2018 | Fodor et al. |
| 10,041,949 B2 | 8/2018 | Bendall et al. |
| 10,053,723 B2 | 8/2018 | Hindson et al. |
| 10,059,990 B2 | 8/2018 | Boyden et al. |
| 10,071,377 B2 | 9/2018 | Bharadwaj et al. |
| 10,137,449 B2 | 11/2018 | Bharadwaj et al. |
| 10,138,509 B2 | 11/2018 | Church et al. |
| 10,150,117 B2 | 12/2018 | Bharadwaj et al. |
| 10,150,964 B2 | 12/2018 | Hindson et al. |
| 10,179,932 B2 | 1/2019 | Church et al. |
| 10,221,442 B2 | 3/2019 | Hindson et al. |
| 10,343,166 B2 | 7/2019 | Bharadwaj et al. |
| 10,347,365 B2 | 7/2019 | Wong et al. |
| 10,400,235 B2 | 9/2019 | Belhocine et al. |
| 10,428,326 B2 | 10/2019 | Belhocine et al. |
| 10,550,429 B2 | 2/2020 | Harada et al. |
| 10,610,865 B2 | 4/2020 | Bharadwaj et al. |
| 10,815,525 B2 | 10/2020 | Lucero et al. |
| 11,041,202 B2 * | 6/2021 | Robins ................. C12Q 1/6804 |
| 12,168,801 B1 | 12/2024 | Hill |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Ost et al. |
| 2007/0166705 A1 | 7/2007 | Milton et al. |
| 2008/0280773 A1 | 11/2008 | Fedurdo et al. |
| 2009/0026082 A1 | 1/2009 | Rothberg et al. |
| 2009/0127589 A1 | 5/2009 | Rothberg et al. |
| 2010/0055733 A1 | 3/2010 | Lutolf et al. |
| 2010/0137143 A1 | 6/2010 | Rothberg et al. |
| 2010/0282617 A1 | 11/2010 | Rothberg et al. |
| 2011/0059865 A1 | 3/2011 | Smith et al. |
| 2011/0172105 A1 | 7/2011 | Gage |
| 2012/0270305 A1 | 10/2012 | Williamson et al. |
| 2013/0079232 A1 | 3/2013 | Kain et al. |
| 2013/0260372 A1 | 10/2013 | Buermann et al. |
| 2014/0079923 A1 | 3/2014 | George et al. |
| 2014/0155295 A1 | 6/2014 | Hindson et al. |
| 2014/0378345 A1 | 12/2014 | Hindson et al. |
| 2015/0218620 A1 | 8/2015 | Behlke |
| 2015/0376609 A1 | 12/2015 | Hindson et al. |
| 2015/0376700 A1 | 12/2015 | Schnall-Levin |
| 2016/0298185 A1 | 10/2016 | Shukla |
| 2017/0016053 A1 | 1/2017 | Beechem et al. |
| 2017/0253918 A1 | 9/2017 | Kohman et al. |
| 2018/0052081 A1 | 2/2018 | Kohman et al. |
| 2018/0105808 A1 | 4/2018 | Mikkelsen et al. |
| 2018/0156784 A1 | 6/2018 | Usmani et al. |
| 2018/0245142 A1 | 8/2018 | So et al. |
| 2018/0312873 A1 | 11/2018 | Zheng |
| 2019/0032121 A1 | 1/2019 | Daugharthy et al. |
| 2019/0177800 A1 | 6/2019 | Boutet et al. |
| 2019/0323088 A1 | 10/2019 | Boutet et al. |
| 2019/0367969 A1 | 12/2019 | Bell et al. |
| 2020/0392479 A1 | 12/2020 | Blainey |
| 2021/0174898 A1 | 6/2021 | Bell |
| 2021/0241853 A1 | 8/2021 | Helpler et al. |
| 2022/0220470 A1 | 7/2022 | Pan |

FOREIGN PATENT DOCUMENTS

| | | |
|---|---|---|
| WO | WO 2005/065814 A1 | 7/2005 |
| WO | WO 2006/064199 A1 | 6/2006 |
| WO | WO 2007/010251 A2 | 1/2007 |
| WO | WO 2009099602 A1 | 8/2009 |
| WO | WO 2011/094669 A1 | 8/2011 |
| WO | WO 2011/127099 A1 | 10/2011 |
| WO | WO 2012/140224 A1 | 10/2012 |
| WO | WO 2014/060483 A1 | 4/2014 |
| WO | WO 2014/163886 A1 | 10/2014 |
| WO | WO 2014/189957 | 11/2014 |
| WO | WO 2014/210225 A1 | 12/2014 |
| WO | WO 2014/210233 A1 | 12/2014 |
| WO | WO 2014/210353 | 12/2014 |
| WO | WO 2015/161173 A1 | 10/2015 |
| WO | WO 2015/200871 | 12/2015 |
| WO | WO 2016/007839 | 1/2016 |
| WO | WO 2016/057552 | 4/2016 |
| WO | WO 2016/162309 | 10/2016 |
| WO | WO 2016/166128 | 10/2016 |
| WO | WO 2017/027367 | 2/2017 |
| WO | WO 2017/027368 | 2/2017 |
| WO | WO 2017/144338 | 8/2017 |
| WO | WO 2017/147483 | 8/2017 |
| WO | WO 2017/222453 | 12/2017 |
| WO | WO 2018/022809 | 2/2018 |
| WO | WO 2018/045181 | 3/2018 |
| WO | WO 2018/045186 | 3/2018 |
| WO | WO 2018/057999 | 3/2018 |
| WO | WO 2018/075693 | 4/2018 |
| WO | WO 2018/091676 | 5/2018 |
| WO | WO 2018/107054 | 6/2018 |
| WO | WO 2018/119447 | 6/2018 |
| WO | WO 2018/136856 | 7/2018 |
| WO | WO 2018/218226 | 11/2018 |
| WO | WO 2019/068880 | 4/2019 |
| WO | WO 2019/075091 | 4/2019 |
| WO | WO 2019/157529 | 8/2019 |
| WO | WO 2020092646 A1 | 5/2020 |
| WO | WO 2021242793 A2 | 12/2021 |

OTHER PUBLICATIONS

Diggins, Kirsten E., P. Brent Ferrell Jr, and Jonathan M. Irish. "Methods for discovery and characterization of cell subsets in high dimensional mass cytometry data." Methods 82 (2015): 55-63. (Year: 2015).*

Petegrosso, Raphael, Zhuliu Li, and Rui Kuang. "Machine learning and statistical methods for clustering single-cell RNA-sequencing data." Briefings in bioinformatics 21.4 (2020): 1209-1223. (Year: 2020).*

Klinger M, Pepin F, Wilkins J, Asbury T, Wittkop T, et al. (2015) Multiplex Identification of Antigen-Specific T Cell Receptors Using a Combination of Immune Assays and Immune Receptor Sequenc-

(56) References Cited

OTHER PUBLICATIONS ing. PLOS ONE 10(10): e0141561. 21 pages, https://doi.org/10.1371/journal.pone.0141561 (Year: 2015).*
U.S. Appl. No. 63/011,779, entitled "Systems and Methods for Visualizing Adaptive Immune Cell Clonotyping Data," filed Apr. 17, 2020.
U.S. Appl. No. 63/011,783, entitled "Systems and Methods for Identifying Adaptive Immune Cell Clonotypes," filed Apr. 17, 2020.
U.S. Appl. No. 63/073,830, entitled "Systems and Methods for Identifying Cells That are Antigen-Specific for an Immunogenic Feature," filed Sep. 2, 2020.
U.S. Appl. No. 62/017,589, entitled "Processes and Systems for Nucleic Acid Sequence Assembly" filed Jun. 26, 2014.
U.S. Appl. No. 62/969,897 entitled "Systems and Methods for Index Hopping Filtering," filed Feb. 4, 2020.
U.S. Appl. No. 63/022,988 entitled "Systems and Methods for Index Hopping Filtering," filed May 11, 2020.
U.S. Appl. No. 62/041,825, entitled "Pipeline for Spatial Analysis of Analytes," filed Jun. 20, 2020.
U.S. Appl. No. 62/047,678, entitled "Systems and Methods for Identifying Morphological Patterns in Tissue Samples," filed Jun. 20, 2020.
U.S. Appl. No. 62/047,678 entitled "Biomarkers for Distinguishing Between Aggressive Prostate Cancer and Non-Aggressive Prostate Cancer," filed Jul. 2, 2020.
U.S. Appl. No. 62/839,346 entitled "Spatial Transcriptomics of Biological Analytes in Tissue Samples," filed Apr. 26, 2019.
U.S. Appl. No. 62/886,233, entitled "Systems and Methods for Using the Spatial Distribution of Haplotypes to Determine a Biological Condition" filed Aug. 13, 2019.
U.S. Appl. No. 62/929,686 entitled "Capturing Targeted Genetic Targets Using a Hybridization/Capture Approach", filed.
U.S. Appl. No. 62/938,336, entitled "Pipeline for Spatial Analysis of Analytes," filed Nov. 21, 2019.
U.S. Appl. No. 62/970,066, entitled "Capturing Targeted Genetic Targets Using a Hybridization/Capture Approach", filed Feb. 4, 2020.
U.S. Appl. No. 62/979,889, entitled "Capturing Targeted Genetic Targets Using a Hybridization/Capture Approach", filed Feb. 21, 2020.
U.S. Appl. No. 17/078,288, entitled "Capturing Targeted Genetic Targets Using a Hybridization/Capture Approach" filed Oct. 23, 2020.
10X Genomics, "What is a template switch oligo (TSO)?," https://kb.10xgenomics.com/hc/en-us/articles/360001493051-What-is-a-template-switch-oligo-TSO-.
10X Genomics, "What is the difference between Single Cell 3' and 5' Gene Expression libraries?" available on the Internet at kb.10xgenomics.com/hc/en-us/articles/360000939852-What-is-the-difference-between-Single-Cell-3-and-5-Gene-Expression-libraries-.
10X Genomics, "Enclone", Internet at Github at 10XGenomics/enclone, last accessed Aug. 31, 2020.
10X Genomics, A "MegaCell Demonstration" by (10X Genomics Datasets, 2017, on the Internet at 10xgenomics.com/solutions/single-cell/).
10X Genomics, 2020, "Technical Note—Interpreting Intronic and Antisense Reads in Single Cell Gene Expression Data", Document No. CG000376, Rev A.
10X Genomics, 2019, "Chromium Next GEM Single Cell 3' Reagent Kits v3.1 User Guide", Document No. CG000204, Rev D.
10X Genomics, 2017, "Chromium Single Cell 3' Reagent Kits v2 User Guide," Document No. CG00052 Rev B.
10X Genomics, 2020, "Chromium Single Cell V(D)J Reagents Kits User Guide," Document No. CG000086, Rev M.
10X Genomics, 2021, "Targeted Gene Expression—Single Cell User Guide", Document No. CG000293, Rev E.
Bailey et al., 2018, "Comprehensive Characterization of Cancer Driver Genes and Mutations," Cell 173(2), pp. 371-385.
Behan et al., 2019, Prioritization of cancer therapeutic targets using CRISPR-Cas9 screens, Nature 568, pp. 511-516.

Blasi et al. 2016, "Label-free cell cycle analysis for high-throughput imaging flow cytometry," Nat. Commun. 7:10256 doi: 10.1038/ncomms10256.
Blondel et al., Jul. 25, 2008, "Fast unfolding of communities in large networks," arXiv:0803.0476v2.
Bourcy et al., 2014, "A Quantitative Comparison of Single-Cell Whole Genome Amplification Methods," PLOS ONE 9(8), e105585.
Caicedo et al., 2017, "Data-analysis strategies for image-based cell profiling," Nature Methods 14(9), pp. 849-863.
Chen et al., 2010, "Clustering-based identification of clonally-related immunoglobulin gene sequence sets," Immunome Res. 6 Suppl 1:S4.
Chen et al., Science 348(6233):aaa6090, 2015.
Compeau et al., 2017, "Why are de Bruijn graphs useful for genome assembly?" Nat Biotechnol. 29(11):987-991: doi:10.1038/nbt.2023.
Costello et al., 2018, "Characterization and remediation of sample index swaps by non-redundant dual indexing on massively parallel sequencing platforms," BMC Genomics.
Cunningham, 2007, "Dimension Reduction," University College Dublin, Technical Report UCD-CSI-2007-7.
Cunningham et al., Ensembl 2019, PubMed PMID: 30407521, doi:10.1093/nar/gky1113.
Dave Tang's Blog, "10x single cell BAM files", https://davetang.org/muse/2018/06/06/10x-single-cell-bam-files/.
Denisenko et al., 2019, "Systematic assessment of tissue dissociation and storage biases in single-cell and single-nucleus RNA-seq workflows," bioRxiv preprint doi: https://doi.org/10.1101/832444.
De Vos, 2010, "High content image cytometry in the context of subnuclear organization," Cytometry Part A 77A, pp. 64-75.
Diggins, K.E., P. Brent Ferrell Jr, and Jonathan M. Irish. "Methods for discovery and characterization of cell subsets in high dimensional mass cytometry data." Methods 82 (2015): 55-63.
Fang et al., 2003, "Fluoride-Cleavable Biotinylation Phosphoramidite for 5'-end-Labelling and Affinity Purification of Synthetic Oligonucleotides," Nucleic Acids Res. 31(2), pp. 708-715.
Fang et al., 2019, "A genetics-led approach defines the drug target landscape of 30 immune-related traits," Nature Genetics 51(7); pp. 1082-1091.
Farouni et al., 2019, "Statistical modeling, estimation, and remediation of sample index hopping in multiplexed droplet-based single-cell RNA-seq data," bioRxiv preprint posted online Apr. 24, 2019; doi: 10.1101/617225.
Fodor, 2002, "A survey of dimension reduction techniques," Center for Applied Scientific Computing, Lawrence Livermore National, Technical Report UCRL-ID-148494.
Ganusov et al., 2007, "Do most lymphocytes in humans really reside in the gut?," Trends Immunol, 208(12), pp. 514-518.
Gao et al., BMC Biol. 15:50, 2017.
Giansanti, 2020, "Fast analysis of scATAC-seq data using a pre-defined set of genomic regions," F1000Research 9, 199.
Gnirke et al., 2009, "Solution Hybrid Selection with Ultra-long Oligonucleotides for Massively Parallel Targeted Sequencing," Nature Biotechnology. Feb. 27(2): 182-189, doi:10.1038/nbt. 1523.
Griffiths et al., 2018, "Detection and removal of barcode swapping in single-cell RNA-seq data," Nature Communications 9, Article No. 2667.
Gupta et al., Nature Biotechnol. 36:1197-1202, 2018.
Hershberg et al., 2015, "The analysis of clonal expansion in normal and autoimmune B cell repertoires," Philos Trans R Soc Lond B Biol Sci. 370(1676).
Hoadley et al., 2018, Cell-of-Origin Patterns Dominate the Molecular Classification of 10,000 Tumors from 33 Types of Cancer, Cell 173(2), pp. 291-304.
Hong, 2018, "QSurface: fast identification of surface expression markers in cancer," BMC Syst Biol. 12(Suppl 2):17, doi:10.1186/s12918-018-0541-6.
Illumina, "Effects of index misassignment on multiplexing and downstream analysis," on the Internet at illumina.com, 2017.
Illumina, "An introduction to Next-Generation Sequencing Technology" illumina.com/content/dam/illumina-marketing/documents/products/illumina_sequencing_introduction.pdf, last accessed Feb. 1, 2020.

(56)        References Cited

OTHER PUBLICATIONS

Kandoth et al., 2013, "Mutational landscape and significance across 12 major cancer types," Nature 502(7471), p. 333-339.

Kurtz et al., 2004, "Versatile and open software for comparing large genomes," Genome Biol doi: 10.1186/GB-2004-5-2-r12.

Kuznetsova et al., 2017, "Generation of populations of antigen-specific cytotoxic T cells using DSs transfected with DNA construct encoding HER2/neu tumor antigen epitopes," BMI Immunology 18:31.

Larsson, A.J.M et al., "Computational correction of index switching in multiplexed sequencing libraries" Nature Methods vol. 14No. 5 May 2018.

Lee et al., "Fluorescent in situ Sequencing (FISSEQ) of RNA for Gene Expression Profiling in Intact Cells and Tissues", Nat. Protoc. 10(3):442-458, 2015.

Lee et al., 2019, "Multi-ATOM: Ultrahigh-throughput single-cell quantitative phase imaging with subcellular resolution," Journal of Biophotonics doi.org/10.1002/jbio.201800479.

Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi:10.1182/blood-2003-11-3857.

Li, Q., "Reliable multiplex sequencing with rare index mis-assignment on DNB-based NGS platform" BMC Genomics (2019) 20:215.

Liu, D. 2019. Algorithms for efficiently collapsing reads with Unique Molecular Identifiers. Peer J 7:e8275 http://doi.org/10.7717/peerj.8275 (Year: 2019).

Liu, P., et al. "Recent advances in computer-assisted algorithms for cell subtype identification of cytometry data." Frontiers in cell and developmental biology 8 (2020): 234.

Macconaill, L.E. et al., (2018). "Unique, dual-indexed sequencing adapters with UMIs effectively eliminate index cross-talk and significantly improve sensitivity of massively parallel sequencing." BMC genomics, 19, 1-10.

Malkov and Yashunin, 2016, "Efficient and robust approximate nearest neighbor search using Hierarchical Navigable Small World graphs," arXiv: 1603.09320 at arxiv.org/abs/1603.09320.

Marks et al., 2020, "How repertoire data is changing antibody science," The Journal of Biological Chemistry 295, 9823-9837.

Matsuda et al., 1998, "The complete nucleotide sequence of the human immunoglobulin heavy chain variable region locus," The Journal of Experimental Medicine. 188 (11): 2151-62, doi:10.1084/jem.188.11.2151.

Miles et al., 2011, "Bias in the ap T-cell repertoire: implications for disease pathogenesis and vaccination," Immunol Cell Biol. 89, pp. 375-387.

Mostovoy et al., 2016, "A hybrid approach for de novo human genome sequence assembly and phasing," Nat. Methods 13, 587-590.

Narasimhan et al., 2016, "Health and population effects of rare gene knockouts in adult humans with related parents," Science 352, pp. 474-477 (2016).

Navin et al., 2011, "Tumour evolution inferred by single-cell sequencing," Nature 472, pp. 90-94.

Ning, Z., et al., "A Fast Search Method for Large DNA Databases. Genome Research," 2001, 11, 1725-1729.

Padmaja, et al. (Aug. 18, 2016). 2016 IEEE 6th International Conference on Advanced Computing (IACC). pp. 31-34. doi:10.1109/IACC.2016.16, ISBN 978-1-4673-8286-1.

Peng et al., 2015, "Reducing amplification artifacts in high multiplex amplicon sequencing by using molecular barcodes," BMC Genomics. 16(1):589, doi: 10.1186/s12864-015-1806-8.

Petegrosso, R. et al. "Machine learning and statistical methods for clustering single-cell RNA-sequencing data." Briefings in bioinformatics 21.4 (2020): 1209-1223.

Quadratic-Time, https://inst.eecs.berkeley.edu/~cs10/labs/cur/programming/algorithms/timing/quadratic-time.html?topic=berkeley_bjc%2Fareas%2Falgorithm-complexity.topic&course=berkeley_bjc.html&noassignment.

Ramani, V., et al. (2017). Massively multiplex single-cell Hi-C. Nature methods, 14(3), 263-266.

Rodriques et al., Science 363(6434):1463-1467, 2019.

Rosati, 2017, "Overview of methodologies for T-cell receptor repertoire analysis," BMC Biotechnology 17:61.

Sanchez-Vega et al., 2018, "Oncogenic Signaling Pathways in The Cancer Genome Atlas," Cell 173(2), pp. 321-337.

Sinha et al., 2017, "Index switching causes 'spreading-of-signal' among multiplexed samples in Illumina HISEQ 4000 DNA sequencing," bioRxiv.

Smith, A.N.S. et al., (2019). Dual indexed design of in-Drop single-cell RNA-seq libraries improves sequencing quality and throughput. bioRxiv, 835488.

Snyder et al., 2012, "Clonal Evolution of Preleukemic Hematopoietic Stem Cells Precedes Human Acute Myeloid Leukemia," Science Translational Medicine 4, 149ra118.

Spitzer et al., 2016, "Mass Cytometry: Single Cells, Many Features," Cell 165(4), pp. 780-791.

Stassen et al., "PARC: ultrafast and accurate clustering of phenotypic data of millions of single cells," BioRxiv preprint doi.org/10.1101/765628.

Stoeckius, M. et al. "Cell Hashing with barcoded antibodies enables multiplexing and doublet detection for single cell genomics" Genome Biology (2018) 19:224 (Year: 2018).

Tandonnet et al., 2017, "Traditional versus 3' RNA-seq in a non-model species," Genom Data. 11:9-16, doi:10.1016/j.gdata.2016.11.002.

Tario et al., 2015, "Dextramer Reagents are Effective Tools for Quantifying CMV Antigen-Specific T Cells from Peripheral Blood Samples," Cytometry Part B (Clinical Cytometry) 888:6-20.

Thermofisher Scientific Invitrogen, technical note "How to prevent index hopping" 2019.

Thorsson et al., 2018, "The Immune Landscape of Cancer," Immunity 48(4), pp. 812-830.

Traag et al., 2019, "From Louvain to Leiden: guaranteeing well-connected communities," Scientific Reports 9: 5233 at doi.org/10.1038/s41598-019-41695-z.

Trejo et al., PLoS ONE 14(2):e0212031, 2019.

Turner et al., 2006, Structural determinants of T cell receptor bias in immunity, Nat Rev Immunol 6, pp. 883-894.

Unix & Linux Stack Exchange, "Sorting Lexicographically by 'all fields'", https://unix.stackexchange.com/questions/307293/sorting-lexicographically-by-all-fields.

Vigneron, 2015, "Human Tumor Antigens and Cancer Immunotherapy," BioMed Research International 2015, Article ID 948501.

Voet et al., 2013, "Single-cell paired-end genome sequencing reveals structural variation per cell cycle," Nucleic Acids Res 41: 6119-6138.

Wentian et al., 2014, "Diminishing return for increased Mappability with longer sequencing reads: implications of the k-mer distributions in the human genome," BMC Bioinformatics 15(2).

Wolfgang et al., 2007, "Graphs in molecular biology," BMC Bioinformatics. 8(Suppl 6): S8: doi:10.1186/1471-2105-8-S6-S8.

Wu et al., 2015, "Maturation and Diversity of the VRC01-Antibody Lineage over 15 Years of Chronic HIV-1 Infection," Cell 161(3), pp. 470-485.

Xu et al., 2015, "A Comprehensive Survey of Clustering Algorithms," Ann. Data. Sci. 2(2) 165-193.

Yaari et al., 2015, "Practical guidelines for B cell repertoire sequencing analysis," Genome Medicine 7:121.

Yassai et al., 2009, "A clonotype nomenclature for T cell receptors," Immunogenetics 61, pp. 493-502.

Zahorian et al., 2011, "Nonlinear Dimensionality Reduction Methods for Use with Automatic Speech Recognition," Speech Technologies. doi:10.5772/16863. ISBN 978-953-307-996-7.

Zheng et al., 2016 "Haplotyping germline and cancer genomes with high-throughput linked-read sequencing," Nat. Biotechnol. 34, pp. 303-311.

(56) References Cited

OTHER PUBLICATIONS

Zheng et al., 2017, "Massively parallel digital transcriptional profiling of single cells," Nat. Commun. 8, 14049 doi: 10.1038/ncomms14049.

Zong et al., 2012, "Genome-wide detection of single nucleotide and copy-number variations of a single human cell," Science 338, pp. 1622-1626.

Ray et al., Comprehensive identification of mRNA isoforms reveals the diversity of neural cell-surface molecules with roles in retinal u development and disease, Nat Commun. Jul. 3, 2020;11 (1):3328. doi: 10.1038/s41467-020-17009-7.

Yap et al., Polarizing the Neuron through Sustained Co-expression of Alternatively Spliced Isoforms, Cell Rep. May 1, 2016 O; 15(6): 1316-28. doi: 10.1016/j.celrep.2016.04.012. Epub Apr. 2, 20168.

Fan, Wenjun, et al., "Widespread Genetic Heterogeneity of Human Ribosomal RNA Genes," RNA (2022) 28:478-492.

* cited by examiner

| TRA | TRB | Count |
|---|---|---|
| CAGGGSQGNLIF (Seq ID No.: 1) | CASSIRSSYEQYF (Seq ID No.: 2) | 3 |
| CAGGGSQGNLIF (Seq ID No.: 3) | CASSVRSSYEQYF (Seq ID No.: 4) | 3 |
| CAGASGSSNTGKLIF (Seq ID No.: 5) | CASSIRSAYEQYF (Seq ID No.: 6) | 2 |
| CAFMKDAGGTSYGKLTF (Seq ID No.: 7) | CASSIGVYGYTF (Seq ID No.: 8) | 1 |
| CAENDGNQFYF, CAGGGSQGNLIF (Seq ID No.: 9) (Seq ID No.: 10) | CASSLERGTDTQYF, CASSIRSSYEQYF (Seq ID No.: 11) (Seq ID No.: 12) | 1 |
| CAVRDGTGANNLFF (Seq ID No.: 13) | CASSISSTGELFF (Seq ID No.: 14) | 1 |
| CAVVLGSGNTGKLIF (Seq ID No.: 15) | CASSIRSAYEQYF (Seq ID No.: 16) | 1 |
| CAVVPGNTGKLIF (Seq ID No.: 17) | CASSIRSGESRAFF (Seq ID No.: 18) | 1 |

Figure 20

| TRA | TRB | Count |
|---|---|---|
| CAGGGSQGNLIF (Seq ID No.: 33) | CASSIRSSYEQYF (Seq ID No.: 34) | 16 |
| CAGGGSQGNLIF (Seq ID No.: 35) | CASSVRSSYEQYF (Seq ID No.: 36) | 7 |
| CAGAHGSSNTGKLIF (Seq ID No.: 37) | CASSIRSAYEQYF (Seq ID No.: 38) | 7 |
| CAVTDGGSQGNLIF (Seq ID No.: 39) | CASSIRSSYEQYF (Seq ID No.: 40) | 5 |
| CAFMTNAGGTSYGKLTF (Seq ID No.: 41) | CASSQGAYGYTF (Seq ID No.: 42) | 3 |
| CAVAVGVSGGGADGLTF (Seq ID No.: 43) | CASSQGAYGYTF (Seq ID No.: 44) | 3 |
| ... | ... | ... |

44 more singleton clonotypes

CD8a + 1

3600

3602

Identify cells that are antigen-specific for a first immunogenetic feature by first obtaining a representation, in electronic form, for each respective immunogenetic feature in a plurality of immunogenetic features, of a corresponding count of the respective immunogenetic feature bound to each immune cell in a population of cells. In some embodiments, the population of cells comprises at least 100, 500, or 1000 immune cells and the plurality of immunogenetic features comprises at least 2, 10, or 20 immunogenetic features.

3604

The population of cells is from a single subject.

3606

The population of cells consists of B cells.

3608

The population of cells consists of T cells.

3609

Acquire the corresponding count of the respective immunogenetic feature bound to each immune cell in the population of cells through flow cytometry, mass cytometry, or high-content imaging cytometry.

3610

The at least 100, 500, or 1000 immune cells are B cells, and the first immunogenetic feature is associated with B cells.

3612

The first immunogenetic feature is CD19, CD20, CD79a, or PAX5.

3614

The at least 100, 500 or 1000 immune cells are T cells, and the first immunogenetic feature is associated with T cells.

3616

The first immunogenetic feature is MHC tetramer, peptide-MHC tetramer, MHC dextramer, or a peptide-MHC dextramer.

3618

The first immunogenetic feature is CD3 or CD8a

3620

The first immunogenetic feature is a tumor antigen.

3622

The population of cells comprises at least 3,000, at least 5,000, at least 10,000, or at least 40,000 cells.

3624

The plurality of immunogenetic features comprises at least 40 immunogenetic features, at least 60 immunogenetic features, at least 80 immunogenetic features, at least 100 immunogenetic features, or at least 200 immunogenetic features.

Each feature in the plurality of features is a cell surface feature.

3628

Each cell surface feature is a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, or an adherens junction.

3630

The representation, for each representative immunogenetic feature in the plurality of immunogenetic features, is collectively in the form of a two-dimensional $l \times m$ features matrix, where $l$ is a positive integer of 100, 500, or 1000 or greater that represents the number of cells in the population of cells, $m$ is a positive integer of 2, 10, 20 or greater that represents the number of immunogenetic features, and each element in the matrix uniquely represents a different feature in the plurality of features and a different cell in the population of cells and provides a count of the number of the different feature that has been detected as bound to the different cell.

3632

Cluster the plurality of immune cells using the representation, thereby obtaining a plurality of clusters. Each cluster in the plurality of clusters includes a different subset of the population of cells.

3634

The clustering comprises phenotyping by accelerated refined community-partitioning.

3636

The clustering is performed using hierarchical clustering, unsupervised clustering, k-means clustering, fuzzy k-means clustering, or Jarvis-Patrick clustering.

3638

The plurality of clusters is between three and one hundred clusters.

3640

The clustering has a time complexity of at least O(n), where n is a product of (i) the number of cells in the population of cells and (ii) a number of immunogenetic features in the plurality of immunogenetic features.

3642

The clustering has a time complexity of at least O(log n), where n is a product of (i) the number of cells in the population of cells and (ii) a number of immunogenetic features in the plurality of immunogenetic features.

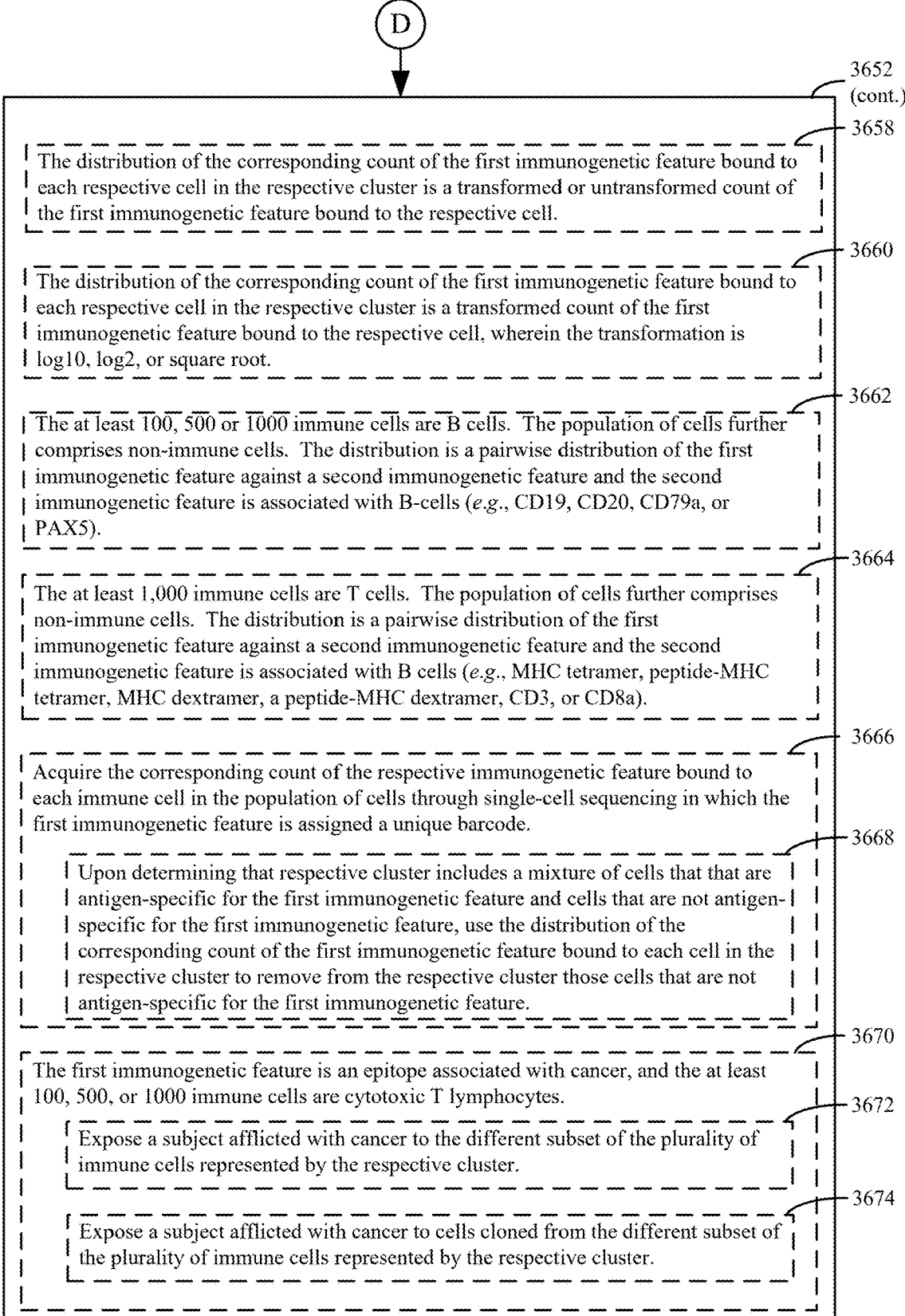

D 3652
(cont.)

3658
The distribution of the corresponding count of the first immunogenetic feature bound to each respective cell in the respective cluster is a transformed or untransformed count of the first immunogenetic feature bound to the respective cell.

3660
The distribution of the corresponding count of the first immunogenetic feature bound to each respective cell in the respective cluster is a transformed count of the first immunogenetic feature bound to the respective cell, wherein the transformation is log10, log2, or square root.

3662
The at least 100, 500 or 1000 immune cells are B cells. The population of cells further comprises non-immune cells. The distribution is a pairwise distribution of the first immunogenetic feature against a second immunogenetic feature and the second immunogenetic feature is associated with B-cells (*e.g.*, CD19, CD20, CD79a, or PAX5).

3664
The at least 1,000 immune cells are T cells. The population of cells further comprises non-immune cells. The distribution is a pairwise distribution of the first immunogenetic feature against a second immunogenetic feature and the second immunogenetic feature is associated with B cells (*e.g.*, MHC tetramer, peptide-MHC tetramer, MHC dextramer, a peptide-MHC dextramer, CD3, or CD8a).

3666
Acquire the corresponding count of the respective immunogenetic feature bound to each immune cell in the population of cells through single-cell sequencing in which the first immunogenetic feature is assigned a unique barcode.

3668
Upon determining that respective cluster includes a mixture of cells that that are antigen-specific for the first immunogenetic feature and cells that are not antigen-specific for the first immunogenetic feature, use the distribution of the corresponding count of the first immunogenetic feature bound to each cell in the respective cluster to remove from the respective cluster those cells that are not antigen-specific for the first immunogenetic feature.

3670
The first immunogenetic feature is an epitope associated with cancer, and the at least 100, 500, or 1000 immune cells are cytotoxic T lymphocytes.

3672
Expose a subject afflicted with cancer to the different subset of the plurality of immune cells represented by the respective cluster.

3674
Expose a subject afflicted with cancer to cells cloned from the different subset of the plurality of immune cells represented by the respective cluster.

Figure 36D

SYSTEMS AND METHODS FOR IDENTIFYING CELLS THAT ARE ANTIGEN-SPECIFIC FOR AN IMMUNOGENIC FEATURE

CROSS REFERENCE TO RELATED PATENT APPLICATION

This application claims priority to U.S. Provisional Patent Application No. 63/073,830, entitled "Systems and Methods for Identifying Cells That are Antigen-Specific for an Immunogenic Feature," filed Sep. 2, 2020, which is hereby incorporated by reference in its entirety.

TECHNICAL FIELD

This specification describes technologies to identify cells that are antigen-specific for a particular immunogenic feature.

BACKGROUND

Rapid development in single-cell technologies, notably flow cytometry, mass cytometry, high-content imaging cytometry, as well as single-cell RNA-sequencing (scRNA-seq), has revolutionized approaches to measuring a multitude of cellular characteristics (from gene and protein expression, to biophysical and morphological phenotypes) at the single-cell precision. This attribute holds the key not only to defining the diversity of cell types, states and functions, but also understanding how the phenotypic variability within an enormous and heterogeneous population of cells plays a role in tissue development, health, and disease. See, Stassen et al., "PARC: ultrafast and accurate clustering of phenotypic data of millions of single cells," BioRxiv preprint doi.org/10.1101/765628. Both single-cell measurement depth and throughput, through techniques such as flow cytometry and mass cytometry, have increased over the years and thus have resulted in a tremendous growth of large-scale single-cell data. Another parallel advance is scRNA-seq. There has been a proliferation in scRNA-seq data with droplet-based systems sequencing hundreds of cells per second (Zheng et al., 2017, "Massively parallel digital transcriptional profiling of single cells," Nat. Commun. 8, 14049 doi: 10.1038/ncomms14049) resulting in tens of thousands of cells across samples in an experiment. A "MegaCell Demonstration" by 10× Genomics (10× Genomics Datasets, 2017, on the Internet at 10×genomics.com/solutions/single-cell/) recently featured a scRNA-seq data set of 1.3 million E18 mouse brain cells, showcasing the very high throughput it can achieve.

One such application of such single-cell measurement is the identification of cells that are antigen-specific for a set of one or more immunogenic features, or antigens. Depending on the nature of the immunogenic feature, such cells have a wide range of applications, from the development of laboratory reagents to development of immune-based therapies. For instance, the minimal residual disease remaining after resection of the major tumor burden underlies the existing problems of tumor recurrence and metastasis, which increase the mortality and morbidity rates among cancer patients. In this connection, there is a need for the development of new technologies that can improve the recognition and elimination of single cancer cells remaining in a patient's body after radiation therapy, chemotherapy, or surgical resection. Currently, cytotoxic T lymphocytes (CTLs) are considered the main effectors in cell-mediated antitumor immunity. It is desirable to isolate CTLs specific to certain antigenic determinants from heterogeneous peripheral blood mononuclear cell (PBMC) populations, in order to target specific cell-mediated immune responses against tumor cells carrying these antigens. See Kuznetsova et al., 2017, "Generation of populations of antigen-specific cytotoxic T cells using DSs transfected with DNA construct encoding HER2/neu tumor antigen epitopes," BMI Immunology 18:31. A large number of antigenic peptides recognized by anti-tumor CTL have been identified. These antigens are classified according to the expression pattern of the parent gene. A regularly updated database of those antigenic peptides effectively presented by tumor cells is found on the Internet at cancerimmunity.org. See, Vigneron, 2015, "Human Tumor Antigens and Cancer Immunotherapy," BioMed Research International 2015, Article ID 948501.

The adaptive human immune system is comprised of B cells and T cells. During T cell and B cell development these cells express unique heterodimeric receptors that are used for recognition of pathogens; in some cases homodimeric receptors can constitute a functional antigen receptor. Each of these receptor chains is generated by a somatic recombination process that joins different segments of the TCR and BCR genes and creates a novel gene segment. This joining process is imprecise with insertion of non-templated nucleotides (N nucleotides) in the junction site, as well as 3'- and 5'-nucleotide deletion from the germline genes participating in the rearrangement. This region of random nucleotide insertion or deletion referred to as the third complementarity-determining region (CDR3). The resulting CDR3 has a unique nucleotide sequence that is specific to that particular B or T cell and all its progeny, with additional mutations occurring over time in the progeny of B cells through a process termed somatic hypermutation. This gives rise to the clonotypic nature of the receptors. The CDR3 is the portion of these receptors that is most commonly involved in interactions with intact soluble antigens (B cells) or intracellular processed antigens presented as immunogenic peptides loaded in MHC molecules (T cells); however, mutations in the first two CDRs, and in the framework regions (FWRs) can also be essential to recognize a given antigen. See Yassai et al., 2009, "A clonotype nomenclature for T cell receptors," Immunogenetics 61, pp. 493-502; and Wu et al., 2015, "Maturation and Diversity of the VRC01-Antibody Lineage over 15 Years of Chronic HIV-1 Infection," Cell 161 (3), pp. 470-485, which is hereby incorporated by reference.

Central to the technologies that make use of cells that are antigen-specific for a particular immunogenic feature, is the identification of such cells. Attempts to raise such cells often produce a mixture of cells, some of which have no specificity to the desired antigen, some that are specific only to the desired antigen, and some that bind to the desired antigen but also bind to antigens that are not desired. Moreover, methods for determining whether a population is in fact a mixture of such cells or not are laborious, inexact, or otherwise unsatisfactory. Given the importance of identifying cells that are antigen-specific for a particular immunogenic feature, what is needed in the art are improved systems and methods to identify such cells.

SUMMARY

The following presents a summary of the invention in order to provide a basic understanding of some of the aspects of the invention. This summary is not an extensive overview of the invention. It is not intended to identify key or critical elements of the invention or to delineate the scope of the invention. Its sole purpose is to present some of the concepts of the invention in a simplified form as a prelude to the more detailed description that is presented later.

The present disclosure addresses the shortcomings in identifying cells that are antigen-specific for an immunogenic feature. In the present disclosure, a representation, in electronic form, is obtained for each respective immunogenic feature in a plurality of immunogenic features, of a corresponding count of the respective immunogenic feature bound to or presented by each immune cell in a population of cells. In some embodiments, the plurality of immunogenic features includes the first immunogenic feature, the population of cells comprises at least 100 immune cells, at least 500 immune cells, or at least 1000 immune cells, and the plurality of immunogenic features comprises at least 2 immunogenic features. The plurality of immune cells is clustered using the representation, thereby obtaining a plurality of clusters, where each cluster in the plurality of clusters includes a different and unique subset of the plurality of immune cells. There is obtained, for a first cluster in the plurality of clusters, a total number of unique immune cell receptor clonotypes detected within the different and unique subset of the plurality of immune cells represented by the first cluster. There is also obtained a total number of immune cell receptor clonotypes detected within the different and unique subset of the plurality of immune cells represented by the first cluster. The present disclosure uses (i) a distribution of a corresponding count of the first immunogenic feature bound to or presented by each cell in the first cluster, a (ii) total number of unique immune cell receptor clonotypes detected within the different and unique subset of the plurality of immune cells represented by the first cluster, and (iii) the total number of immune cell receptor clonotypes detected within the different and unique subset of the plurality of immune cells represented by the first cluster to determine whether the different and unique subset of the plurality of immune cells represented by the first cluster is antigen-specific for the first immunogenic feature.

In some embodiments, the population of cells is from a single subject.

In some embodiments, more than one cell in the respective cluster are members of the same clonotype. In some embodiments, more than ten cells in the respective cluster are members of the same clonotype.

In some embodiments, the total number of unique immune cell receptor clonotypes in the respective cluster comprises 25 clonotypes or comprises 100 clonotypes.

In some embodiments, the total number of unique immune cell receptor clonotypes in the respective cluster comprises a single clonotype with 25 or more exact subclonotypes (e.g. a lymphoma sample).

In some embodiments, the population of cells consists of B cells.

In some embodiments, the population of cells consists of T cells.

In some embodiments, the method further comprises calculating the clonotypic enrichment ratio from the total number of unique immune cell receptor clonotypes detected within the different subset of the population of cells represented by the respective cluster and the total number of immune cell receptor clonotypes detected within the different subset of the population of cells represented by the respective cluster, and also using the clonotypic enrichment ratio to determine whether the different subset of the population of cells represented by the respective cluster is antigen-specific for the first immunogenic feature.

In some embodiments, the total number of unique immune cell receptor clonotypes detected within the different subset of the population of cells represented by the respective cluster and the total number of immune cell receptor clonotypes detected within the different subset of the population of cells represented by the respective cluster is expressed as a clonotypic enrichment ratio, and the distribution of the corresponding count of the first immunogenic feature bound to or presented by each cell in the respective cluster and the clonotypic enrichment ratio is used to determine whether the different subset of the population of cells represented by the respective cluster is antigen-specific for the first immunogenic feature.

In some embodiments, the representation is in the form of a two-dimensional $l \times m$ features matrix, $l$ is a positive integer of 100 or greater, 500 or greater, or 1000 or greater that represents the number of cells in the population of cells, $m$ is a positive integer of 2 or greater that represents the number of immunogenic features, and each element in the two-dimensional $l \times m$ features matrix uniquely represents a different feature in the plurality of features and a different cell in the population of cells and provides a count of the number of the different feature that has been detected as bound to or presented by the different cell.

In some embodiments, the clustering has a time complexity of at least $O(n)$, and $n$ is a product of (i) a number of cells in the population of cells and (ii) a number of immunogenic features in the plurality of immunogenic features.

In some embodiments, the clustering has a time complexity of at least $O (\log n)$, and $n$ is a product of (i) a number of cells in the population of cells and (ii) a number of immunogenic features in the plurality of immunogenic features.

In some embodiments, the clustering comprises phenotyping by accelerated refined community-partitioning.

In some embodiments, the population of cells comprises at least 3,000, at least 5,000, at least 10,000, or at least 40,000 cells.

In some embodiments, the plurality of immunogenic features comprises at least 40 immunogenic features, at least 60 immunogenic features, at least 80 immunogenic features, at least 100 immunogenic features, or at least 200 immunogenic features.

In some embodiments, each feature in the plurality of features is a cell surface feature. In some such embodiments, each cell surface feature is a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T cell receptor, a T cell receptor, a B cell receptor, a chimeric antigen receptor, a gap junction, or an adherens junction.

In some embodiments, the distribution of the corresponding count of the first immunogenic feature bound to or presented by each respective cell in the respective cluster is a transformed or untransformed count of the first immunogenic feature bound to or presented by the respective cell.

In some embodiments, the distribution of the corresponding count of the first immunogenic feature bound to or presented by each respective cell in the respective cluster is a transformed count of the first immunogenic feature bound to or presented by the respective cell, where the transformation is $\log_{10}$, $\log_2$, or square root.

In some embodiments, the at least 100 immune cells, at least 500 immune cells or at least 1000 immune cells are B cells, the population of cells further comprises non-immune cells, the distribution is a pairwise distribution of the first immunogenic feature against a second immunogenic feature, and the second immunogenic feature is associated with B cells. In some such embodiments, the second immunogenic feature is CD19, CD20, CD79a, or PAX5.

In some embodiments, the at least 100, at least 500 or at 1000 immune cells are T cells, the population of cells further comprises non-immune cells, the distribution is a pairwise distribution of the first immunogenic feature against a second immunogenic feature, and the second immunogenic feature is associated with T cells. In some such embodiments, the second immunogenic feature is a MHC tetramer, peptide-MHC tetramer, MHC dextramer, a peptide-MHC dextramer, or peptide-MHC multimer of higher order (e.g., pentamers, octamers, dextramers, polymers, etc.). In alternative embodiments, the second immunogenic feature is CD3 or CD8a.

In some embodiments, the at least 100, at least 500 or at least 1000 immune cells are B cells, and the first immunogenic feature is associated with B cells. In some such embodiments, the first immunogenic feature is CD19, CD20, CD79a, or PAX5.

In some embodiments, the at least 100, at least 500, or at least 1000 immune cells are T cells, and the first immunogenic feature is associated with T cells. In some such embodiments, the first immunogenic feature is a MHC tetramer, peptide-MHC tetramer, MHC dextramer, or a peptide-MHC dextramer. In alternative embodiments the first immunogenic feature is CD3 or CD8a.

In some embodiments, the method further comprises acquiring the corresponding count of the respective immunogenic feature bound to or presented by each immune cell in the population of cells through single-cell sequencing in which the first immunogenic feature is assigned a unique barcode. In some embodiments, the method further comprises determining that the respective cluster includes a mixture of cells that that are antigen-specific for the first immunogenic feature and cells that are not antigen-specific for the first immunogenic feature, and using the distribution of the corresponding count of the first immunogenic feature bound to or presented by each cell in the respective cluster to remove from the respective cluster those cells that are not antigen-specific for the first immunogenic feature.

In some embodiments, the method further comprises acquiring the corresponding count of the respective immunogenic feature bound to or presented by each immune cell in the population of cells through flow cytometry, mass cytometry, or high-content imaging cytometry.

In some embodiments, the first immunogenic feature is an epitope associated with cancer, and the at least 100 immune cells are cytotoxic T lymphocytes. In some such embodiments, the method further comprises exposing a subject afflicted with cancer to the different subset of the plurality of immune cells represented by the respective cluster. In alternative embodiments, the method further comprises exposing a subject afflicted with cancer to cells cloned from the different subset of the plurality of immune cells represented by the respective cluster.

In some embodiments, the first immunogenic feature is a tumor antigen.

In some embodiments, the plurality of clusters is between three and one hundred clusters.

In some embodiments, the clustering is performed using hierarchical clustering, unsupervised clustering, k-means clustering, fuzzy k-means clustering, negative matrix factorization, or Jarvis-Patrick clustering.

Another aspect of the present disclosure provides a computer system comprising one or more processors, memory and one or more programs. The one or more programs are stored in the memory and are configured to be executed by the one or more processors. The one or more programs are for identifying cells that are antigen-specific for a first immunogenic feature. The one or more programs comprise instructions for obtaining a representation, in electronic form, for each respective immunogenic feature in a plurality of immunogenic features, of a corresponding count of the respective immunogenic feature bound to or presented by each immune cell in a population of cells. In some embodiments, the plurality of immunogenic features includes the first immunogenic feature, the population of cells comprises at least 100, at least 500, or at least 1000 immune cells, and the plurality of immunogenic features comprises at least 2, at least 10, or at least 20 immunogenic features. In some embodiments, the plurality of immunogenic features includes both antigens that are known to bind with great specificity to certain immune cells as well as non-specific control antigens that are known to not bind with any particular specificity to immune cells. The one or more programs further comprise instructions for clustering the plurality of immune cells using the representation, thereby obtaining a plurality of clusters, where each cluster in the plurality of clusters includes a different subset of the population of cells. The one or more programs further comprise instructions for obtaining, for a respective cluster in the plurality of clusters, a total number of unique immune cell receptor clonotypes detected within the different subset of the plurality of immune cells represented by the respective cluster. The one or more programs further comprise instructions for obtaining a total number of immune cell receptor clonotypes detected within the different subset of the population of cells represented by the respective cluster. The one or more programs further comprise instructions for using (i) a distribution of a corresponding count of the first immunogenic feature bound to or presented by each cell in the respective cluster, (ii) the total number of unique immune cell receptor clonotypes detected within the different subset of the plurality of immune cells represented by the respective cluster, and (iii) the total number of immune cell receptor clonotypes detected within the different subset of the population of cells represented by the respective cluster to determine whether the different subset of the population of cells represented by the respective cluster is antigen-specific for the first immunogenic feature.

Another aspect of the present disclosure provides a computer readable storage medium storing one or more programs. The one or more programs comprising instructions, which when executed by an electronic device with one or more processors and a memory, cause the electronic device to identify cells that are antigen-specific for a first immunogenic feature by a method. The method comprises obtaining a representation, in electronic form, for each respective immunogenic feature in a plurality of immunogenic features, of a corresponding count of the respective immunogenic feature bound to or presented by each immune cell in a population of cells, where the plurality of immunogenic features includes the first immunogenic feature, the population of cells comprises at least 100, at least 500, or at least 1000 immune cells, and the plurality of immunogenic features comprises at least 2, at least 10, or at least 20 immunogenic features. The method further comprises clustering the plurality of immune cells using the representation, thereby obtaining a plurality of clusters, where each cluster in the plurality of clusters includes a different subset of the population of cells. The method further comprises obtaining, for a respective cluster in the plurality of clusters, a total number of unique immune cell receptor clonotypes detected within the different subset of the plurality of immune cells represented by the respective cluster. The method further comprises obtaining a total number of immune cell receptor clonotypes detected within the different subset of the population of cells represented by the respective cluster. The method further comprises using (i) a distribution of a corresponding count of the first immunogenic feature bound to or presented by each cell in the respective cluster, (ii) the total number of unique immune cell receptor clonotypes detected within the different subset of the plurality of immune cells represented by the respective cluster, and (iii) the total number of immune cell receptor clonotypes detected within the different subset of the population of cells represented by the respective cluster to determine whether the different subset of the population of cells represented by the respective cluster is antigen-specific for the first immunogenic feature.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIG. 20 illustrates the clonotypes represented in the cells of cluster 10 of FIG. 18, which indicate that the cluster contains influenza-specific T cells in accordance with an embodiment of the present disclosure.

FIGS. 36A, 35B, 36C, and 36D illustrate exemplary methods in which optional elements of such methods are indicated by dashed boxes in accordance with an embodiment of the present disclosure.

DETAILED DESCRIPTION

Figure 1A:
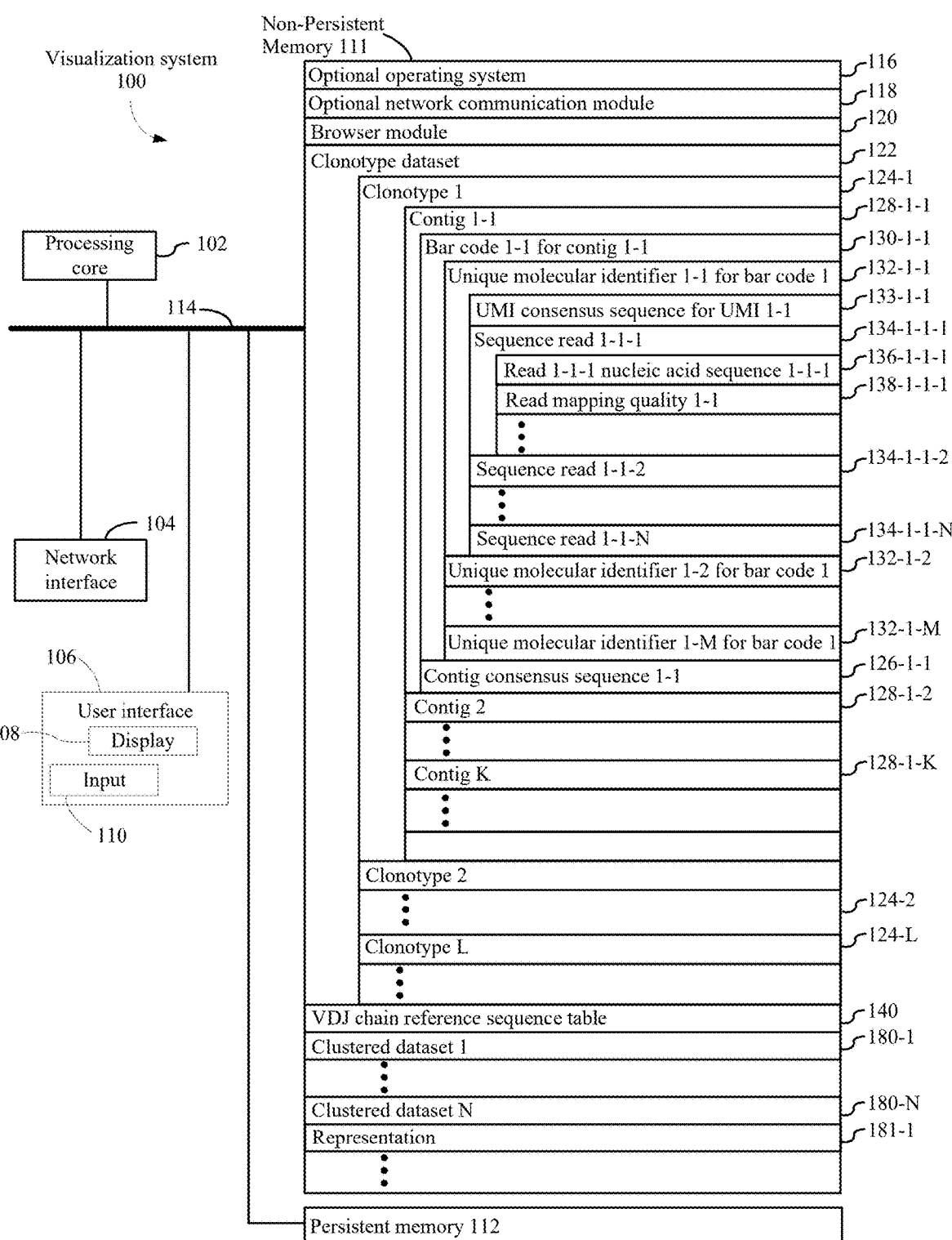
FIGS. 1A and 1B provide an example block diagram illustrating a computing device in accordance with some implementations.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to analyze datasets. An example of such datasets are datasets arising from pipelines that sequence all or a portion of the VDJ regions in single cells, such as B cells and T cells, and that also determine a number of antigens bound to such cells and/or quantify particular cell surface markers presented by such cells. Details of implementations are now described in conjunction with the Figures.

The term "B cells", also known as B lymphocytes, refer to a type of white blood cell of the small lymphocyte subtype. They function in the humoral immunity component of the adaptive immune system by expressing and/or secreting antibodies. B cells are highly diverse, each expressing a practically unique B cell immunoglobulin (e.g., B cell immunoglobulin receptor-BCR). There are approximately $10^{10}$-$10^{11}$ B cells in a human adult. See Ganusov et al., 2007, "Do most lymphocytes in humans really reside in the gut?," Trends Immunol, 208 (12), pp. 514-518, which is hereby incorporated by reference. B cells are important components of adaptive immunity, and directly bind to pathogens through B cell immunoglobulin receptors (BCRs) expressed on the cell surface of the B cells. Each B cell in an organism (e.g. human) expresses a different BCR that allows it to recognize a particular set of molecular patterns. Individual B cells gain this specificity during their development in the bone marrow, where they undergo a somatic rearrangement process that combines multiple germline-encoded gene segments to procure the BCR, as illustrated in FIG. 1 of Yaari and Kleinstein, 2015, "Practical guidelines for B cell repertoire sequencing analysis," Genome Medicine 7:121, which is hereby incorporated by reference. Human antibody molecules (and B cell immunoglobulins) are composed of heavy and light chains (each of which contains both constant (C) and variable (V) regions), which are encoded by genes on three loci: the immunoglobulin heavy locus on chromosome 14, containing the gene segments for the immunoglobulin heavy chain, the immunoglobulin kappa (κ) locus on chromosome 2, containing the gene segments for part of the immunoglobulin light chain, the immunoglobulin lambda (λ) locus on chromosome 22, containing the gene segments for the remainder of the immunoglobulin light chain. Each heavy chain and light chain gene contains multiple copies of three different types of gene segments for the variable regions of the antibody proteins. For example, the human immunoglobulin heavy chain region contains two Constant (Cμ and Cδ) gene segments and 44 Variable (V) gene segments plus 27 Diversity (D) gene segments and 6 Joining (J) gene segments. See Matsuda et al., 1998, "The complete nucleotide sequence of the human immunoglobulin heavy chain variable region locus," The Journal of Experimental Medicine. 188 (11): 2151-62, doi: 10.1084/jem. 188.11.2151; and Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi: 10.1182/blood-2003-11-3857, each of which is incorporated by reference. The light chains also possess two constant (Cμ and Cδ) gene segments and numerous V and J gene segments, but do not have D gene segments. DNA rearrangement causes one copy of each type of gene segment to go in any given lymphocyte, generating an enormous antibody repertoire, although some are removed due to self-reactivity.

The term "T cells", also known as T lymphocytes, refer to a type of an adaptive immune cell. T cells play a central role in the immune response of the body. T cells can be distinguished from other lymphocytes by the presence of a T cell receptor (TCR) on the cell surface. These immune cells originate as precursor cells, derived from bone marrow, and then develop into several distinct types of T cells once they have migrated to the thymus gland. T cell differentiation continues even after they have left the thymus. T cells include, but are not limited to, helper T cells, cytotoxic T cells, memory T cells, regulatory T cells, and killer T cells. Helper T cells stimulate B cells to make antibodies and help killer cells develop. T cells can also include engineered T cells that can attack specific cancer cells. A patient's T cells can be collected and genetically engineered to produce chimeric antigen receptors (CAR). These engineered T cells are called CAR T cells, which forms the basis of the developing technology called CAR-T therapy. These engineered CAR T cells are grown by the billions in the laboratory and then infused into a patient's body, where the cells are designed to multiply and recognize the cancer cells that express the specific protein. This technology, also called adoptive cell transfer is emerging as a potential next-generation immunotherapy treatment. T cells, such as the killer T cells, can directly kill cells that have already been infected by a foreign invader. TCRs are highly diverse heterodimers, consisting of a combination of α and β chains (αβ TCR) expressed by the majority of T cells, or γδ chains (γδ TCR) expressed by T cells in peripheral blood and T cells found at mucosal sites. The TCR chains consist of a variable region, important for antigen recognition, and a constant region. The variable region of TCRα and δ chains is encoded by a number of variable (V) and joining (J) genes, while TCRβ and γ chains are additionally encoded by diversity (D) genes (Miles et al., 2011, "Bias in the αβ T-cell repertoire: implications for disease pathogenesis and vaccination," Immunol Cell Biol. 89, pp. 375-87, and Burtrum et al., 1996, "TCR gene recombination and alpha beta-gamma delta lineage divergence: productive TCR-beta rearrangement is neither exclusive nor preclusive of gamma delta cell development," J Immunol. 157 (10), pp. 4293-6). During VDJ recombination, one random allele of each gene segment is recombined with the others to form a functional variable region. Recombination of the variable region with a constant gene segment results in a functional TCR chain transcript. Additionally, random nucleotides are added and/or deleted at the junction sites between the gene segments. This process leads to strong combinatorial (depending on which gene regions will recombine) and junctional diversity (which and how many nucleotides will be added/deleted), resulting in a large and highly variable TCR repertoire. Additional diversity is achieved by the pairing of α and β or γ and δ chains to form a functional TCR (Turner et al., 2006, Structural determinants of T cell receptor bias in immunity," Nat Rev Immunol 6, pp. 883-94). Each TCR chain contains three hypervariable loops in its structure, termed complementarity determining regions (CDR1-3). CDR1 and 2 are encoded by V genes and are required for interaction of the TCR with the MHC complex. CDR3, however, is encoded by the junctional region between the V and J or D and J genes and is therefore highly variable. It plays an important role in the interaction of the TCR with the peptide-MHC complex, as it is the region of the TCR in direct contact with the peptide antigen. For this reason, CDR3 is often used as the region of interest to determine T cell clonotypes, as it is highly unlikely that two T cells will express the same CDR3 nucleotide sequence, unless they have derived from the same clonally expanded T cell. However, other definitions for T cell clonotype can be used as disclosed herein.

The term "V(D)J recombination" refers to a genetic recombination mechanism that occurs in developing lymphocytes during the early stages of T and B cell maturation. Through somatic recombination, this mechanism produces a highly diverse repertoire of antibodies/immunoglobulins and T cell receptors (TCRs) found in B cells and T cells, respectively. This process is a defining feature of the adaptive immune system and these receptors are defining features of adaptive immune cells. V(D)J recombination occurs in the primary immune organs (bone marrow for B cells and thymus for T cells) and in a generally random fashion. The process leads to the rearranging of variable (V), joining (J), and in some cases, diversity (D) gene segments. The process ultimately results in novel amino acid sequences in the antigen-binding regions of immunoglobulins and TCRs that allow for the recognition of antigens from nearly all pathogens including, for example, bacteria, viruses, and parasites. Furthermore, the recognition can also be allergic in nature or may recognize host tissues and lead to autoimmunity. Because of the rearrangement undergone of the V(D)J region in T cells and B cells, only parts of the V(D)J regions (the V, D, and J segments) can be traced back to segments encoded in highly repetitive regions of the germline that are not typically sequenced directly from the germ line DNA. Furthermore, the V, D, and J segments can be significantly modified during the V(D)J rearrangement process and through, in the case of B cells, somatic hypermutation. As such, there are typically no pre-existing full-length templates to align to sequence reads of the V(D)J regions of T cell receptors and B cell immunoglobulins. Clonal grouping, referred to herein as clonotyping, involves clustering the set of B cell immunoglobulin V(D)J sequences (in the case of B cells) or the set of T cell receptor V(D)J sequences, in the case to T cells into clones, which are defined as a group of cells that are descended from a common ancestor. Members of a B cell clone do not carry identical V(D)J sequences, but differ because of somatic hypermutation. Thus, defining clones (clonotyping) based on BCR sequence data requires machine learning techniques in some instances. See, for example, Chen et al., 2010, "Clustering-based identification of clonally-related immunoglobulin gene sequence sets," Immunome Res. 6 Suppl 1: S4; and Hershberg and Prak, 2015, "The analysis of clonal expansion in normal and autoimmune B cell repertoires," Philos Trans R Soc Lond B Biol Sci. 370 (1676), each of which is hereby incorporated by reference.

Figure 1B:
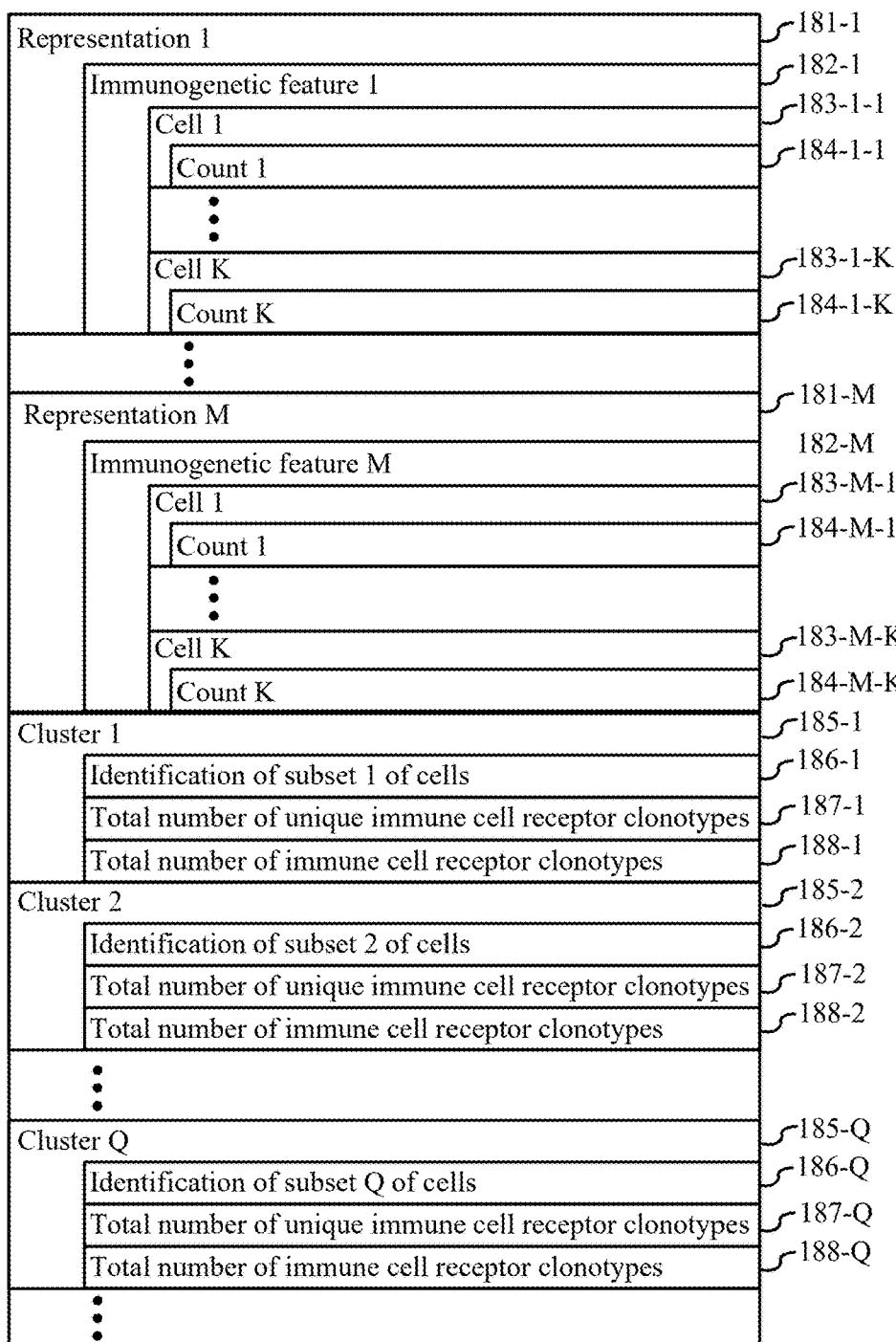

FIGS. 1A and 1B provide a block diagram illustrating a visualization system 100 in accordance with some implementations. The device 100 in some implementations includes one or more central processing units CPU(s) 102 (also referred to as processors), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

an optional operating system 116, which includes procedures for handling various basic system services and for performing hardware dependent tasks;

an optional network communication module (or instructions) 118 for connecting the visualization system 100 with other devices, or a communication network;

a browser module 120 for selecting clonotype datasets 122 and/or representations 181 from persistent memory 112 and presenting an analysis of them;

a clonotype dataset 122, the clonotype dataset comprising a plurality of clonotypes 124, and for each chain in each clonotype 124 (e.g. T cell receptor α chain, T cell receptor β chain, B cell light chain, B cell heavy chain, etc.) in the plurality of clonotypes a consensus sequence for a VDJ region 126 of the chain, where the consensus sequence for the VDJ region 126 is derived from a plurality of contigs 128 of that chain in that clonotype, each contig 128 associated with (i) a barcode 130, (ii) one or more unique molecular identifiers 132, and (iii) a contig consensus sequence 126 across the sequence reads of the unique molecular identifier, each unique molecular identifier 132 supported by a plurality of sequence reads 134 that contribute to the contig consensus sequence 126, each sequence read including information such as a read nucleic acid sequence 136 and a read mapping quality 138;

an optional VDJ chain reference sequence table or donor reference sequence table 140 that includes the reference sequence of all the V genes and J genes in a genome, or at least the ones represented by a given clonotype dataset 122;

optionally, all or a portion of one or more clustered datasets 180 (equivalent to clustered dataset 128 of U.S. Pat. No. 10,347,365), each clustered dataset 180 comprising a plurality of clusters 5002, each cluster 5002 (equivalent to cluster 158 of U.S. Pat. No. 10,347,365) including a subset of cells (second entities 126 of U.S. Pat. No. 10,347,365) 5004, and each respective cell identified by a barcode 130 that supports the cell;

a representation 181 for each respective immunogenic feature 182 in a plurality of immunogenic features, of a corresponding count of the respective immunogenic feature bound to or presented by each immune cell 183 in a population of cells 184; and a plurality of clusters, where each cluster 184 in the plurality of clusters includes an identification of a different subset 186 of the population of cells, a total number of unique immune cell receptor clonotypes 187 detected within the different subset, and a total number of immune cell receptor clonotypes 188 detected within the different subset.

In some implementations, one or more of the above identified elements are stored in one or more of the previously mentioned memory devices and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "visualization system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

While a system in accordance with the present disclosure has been disclosed with reference to FIG. 1, a method in accordance with the present disclosure is now detailed with reference to FIGS. 2 through 39.

Block 3602. Referring to block 3602 of FIG. 36A, the disclosed systems and methods are directed to identifying cells that are antigen-specific for an immunogenic feature. This is done by obtaining a representation 181, in electronic form, for each respective immunogenic feature in a plurality of immunogenic features, of a corresponding count of the respective immunogenic feature 182 bound to or presented by each immune cell 183 in a population of cells.

In some embodiments, the population of cells comprises at least 100 immune cells, at least 200 immune cells, at least 500 immune cells, at least 1,000 immune cells or at least 10,000 immune cells. In some embodiments the population of cells includes both immune cells and cells that are not immune cells.

In some embodiments the plurality of immunogenic features comprises two or more immunogenic features, three or more immunogenic features, four or more immunogenic features, five or more immunogenic features, at least 10 immunogenic features, at least 20 immunogenic features, at least 30 immunogenic features, or at least 50 immunogenic features. In some embodiments, the plurality of immunogenic features includes both antigens that are known to bind with great specificity to certain immune cells as well as non-specific control antigens that are known to not bind with any particular specificity to immune cells.

As discussed in more detail below, examples of immunogenic features generally include, but are not limited to, markers (e.g., proteins, moieties, biomolecules) presented on a cell surface and/or antigens bound to or presented by such cells.

In the systems and systems described herein, one or more labelling agents capable of binding to or otherwise coupling to one or more such immunogenic features may be used to characterize cells and/or cell features. Non-limiting examples of labelling agents include, but are not limited to, proteins, peptides, antibodies (or epitope binding fragments thereof), lipophilic moieties (such as cholesterol), cell surface receptor binding molecules, receptor ligands, small molecules, bi-specific antibodies, bi-specific T cell engagers, T cell receptor engagers, B cell receptor engagers, pro-bodies, aptamers, nanobodies, monobodies, affimers, darpins, and protein scaffolds, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. In some embodiments, the immunogenic feature under study binds to cells and is itself labeled. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In a particular example, a library of potential cell feature labelling agents may be provided associated with nucleic acid reporter molecules, e.g., where a different reporter oligonucleotide sequence is associated with each labelling agent capable of binding to a specific cell feature. In some aspects, different members of the library may be characterized by the presence of a different oligonucleotide sequence label, e.g., an antibody capable of binding to a first type of protein may have associated with it a first known reporter oligonucleotide sequence, while an antibody capable of binding to a second protein (e.g., different than the first protein) may have a different known reporter oligonucleotide sequence associated with it. Prior to partitioning, the cells may be incubated with the library of labelling agents, that may represent labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a bead, such as a gel bead). As a result, the partitions may include the cell or cells, as well as the bound labelling agents and their known, associated reporter oligonucleotides.

In other instances, e.g., to facilitate sample multiplexing, a labelling agent that is specific to a particular cell immunogenic feature may have a first plurality of the labelling agent (e.g., an antibody or lipophilic moiety) coupled to a first reporter oligonucleotide and a second plurality of the labelling agent coupled to a second reporter oligonucleotide. In this way, different samples or groups can be independently processed and subsequently combined together for pooled analysis (e.g., partition-based barcoding as described elsewhere herein). See, e.g., U.S. Pat. Pub. 20190323088, which is hereby incorporated by reference its entirety.

In some aspects these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., LIGHTNING-LINK® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang et al., 2003, "Fluoride-Cleavable Biotinylation Phosphoramidite for 5'-end-Labelling and Affinity Purification of Synthetic Oligonucleotides," Nucleic Acids Res. 31 (2), pp. 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink, TriLink, and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photo-labile, thermally labile, etc.). In some instances, the reporter oligonucleotides may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some embodiments, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

Figure 37:
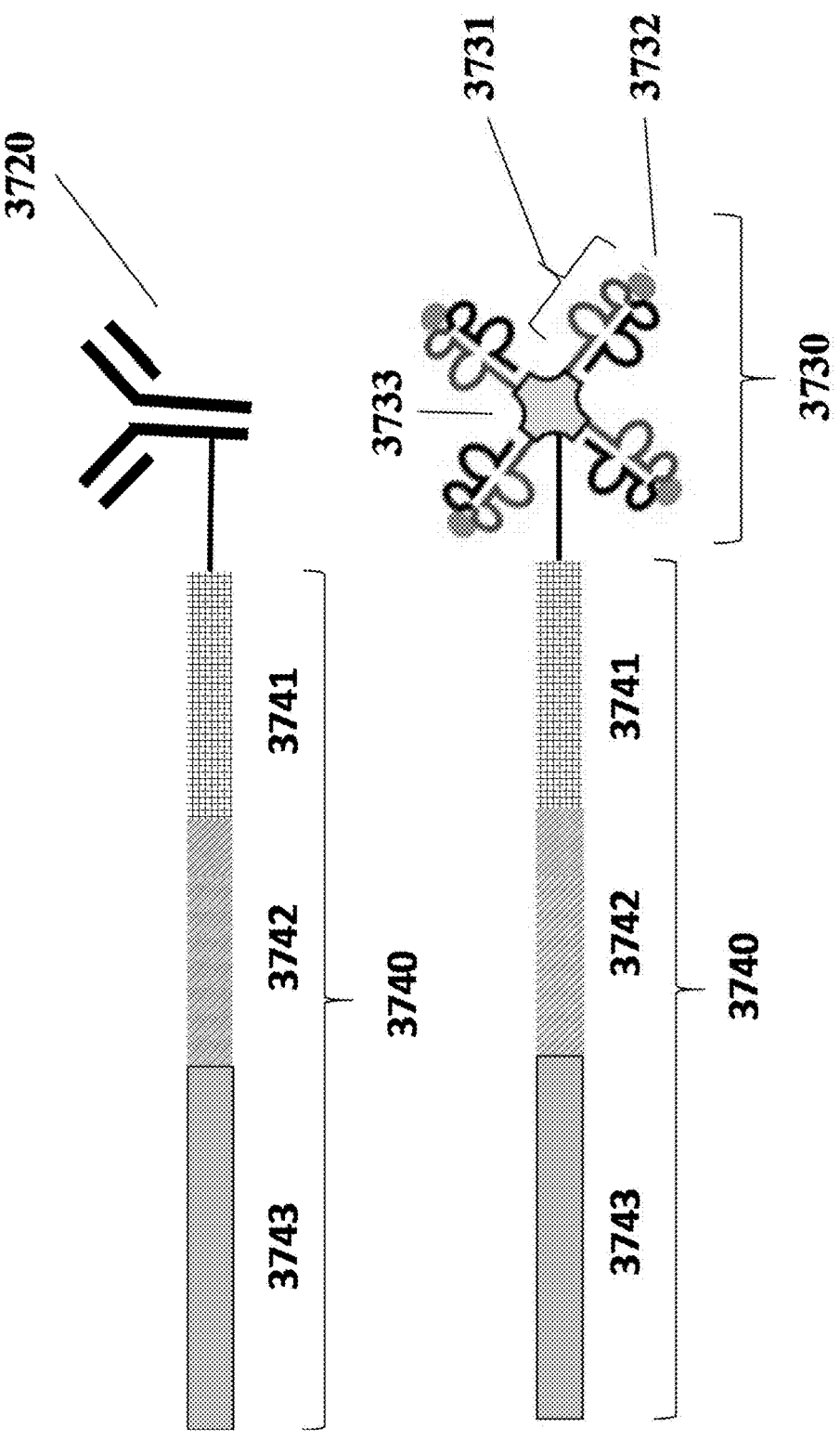
FIG. 37 illustrates exemplary labelling agents in accordance with an embodiment of the present disclosure.

FIG. 37 describes exemplary labelling agents (3710, 3720, 3730) comprising reporter oligonucleotides (3740) attached thereto. Labelling agent 3710 (e.g., any of the labelling agents described herein) is attached (either directly, e.g., covalently attached, or indirectly) to reporter oligo-nucleotide 3740. Reporter oligonucleotide 3740 may comprise barcode sequence 3742 that identifies labelling agent 3710. Reporter oligonucleotide 3740 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 37, in some embodiments, reporter oligonucleotide 3740, conjugated to a labelling agent (e.g., 3710, 3720, 3730), comprises a primer sequence 3741, a barcode sequence that identifies the labelling agent (e.g., 3710, 3720, 3730), and functional sequence 3743. Functional sequence 3743 may be configured to hybridize to a complementary sequence, such as a complementary sequence present on a nucleic acid barcode molecule 3790 (not shown), such as those described elsewhere herein. In some embodiments, nucleic acid barcode molecule 3790 is attached to a support (e.g., a bead, such as a gel bead), such as those described elsewhere herein. For example, nucleic acid barcode molecule 3790 may be attached to the support via a releasable linkage (e.g., comprising a labile bond). In some embodiments, reporter oligonucleotide 3740 comprises one or more additional functional sequences, such as those described above.

In some embodiments, the labelling agent 3710 is a protein or polypeptide (e.g., an antigen or prospective anti-gen) comprising reporter oligonucleotide 3740. Reporter oligonucleotide 3740 comprises barcode sequence 3742 that identifies polypeptide 3710 and can be used to infer the presence of, e.g., a binding partner of polypeptide 3710 (e.g., a molecule or compound to which the polypeptide binds). In some instances, the labelling agent 3710 is a lipophilic moiety (e.g., cholesterol) comprising reporter oligonucle-otide 3740, where the lipophilic moiety is selected such that labelling agent 3710 integrates into a membrane of a cell or nucleus. Reporter oligonucleotide 3740 comprises barcode sequence 3742 that identifies lipophilic moiety 3710 which in some instances is used to tag cells (e.g., groups of cells, cell samples, etc.) for multiplex analyses as described else-where herein. In some embodiments, the labelling agent is an antibody 3720 (or an epitope binding fragment thereof) comprising reporter oligonucleotide 3740. Reporter oligo-nucleotide 3740 comprises barcode sequence 3742 that identifies antibody 3720 and can be used to infer the presence of, e.g., a target of antibody 3720 (e.g., a molecule or compound to which antibody 3720 binds). In other embodiments, labelling agent 3730 comprises an MHC molecule 3731 comprising peptide 3732 and reporter oligo-nucleotide 3740 that identifies peptide 3732. In some instances, the MHC molecule is coupled to a support 3733. In some instances, support 3733 is streptavidin (e.g., MHC molecule 3731 may comprise biotin). In other embodiments, support 3733 is a polysaccharide, such as dextran. In some instances, reporter oligonucleotide 3740 may be directly or indirectly coupled to MHC labelling agent 3730 in any suitable manner, such as to MCH molecule 3731, support 3733, or peptide 3732. In some embodiments, labelling agent 3730 comprises a plurality of MHC molecules, e.g., is an MHC multimer, which may be coupled to a support (e.g., 3733). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., PRO5® MHC Class I Pentamers, (ProImmune, Ltd.), MHC octamers, MHC dodecamers, MHC decorated dextran molecules (e.g., MHC DEX-TRAMER® (Immudex)), etc. For a description of exem-plary labelling agents, including antibody and MHC-based labelling agents, reporter oligonucleotides, and methods of use, see, e.g., U.S. Pat. No. 10,550,429 and U.S. Pat. Pub. 20190367969, which are each incorporated by reference herein in their entirety.

Figures 38A, 38B:
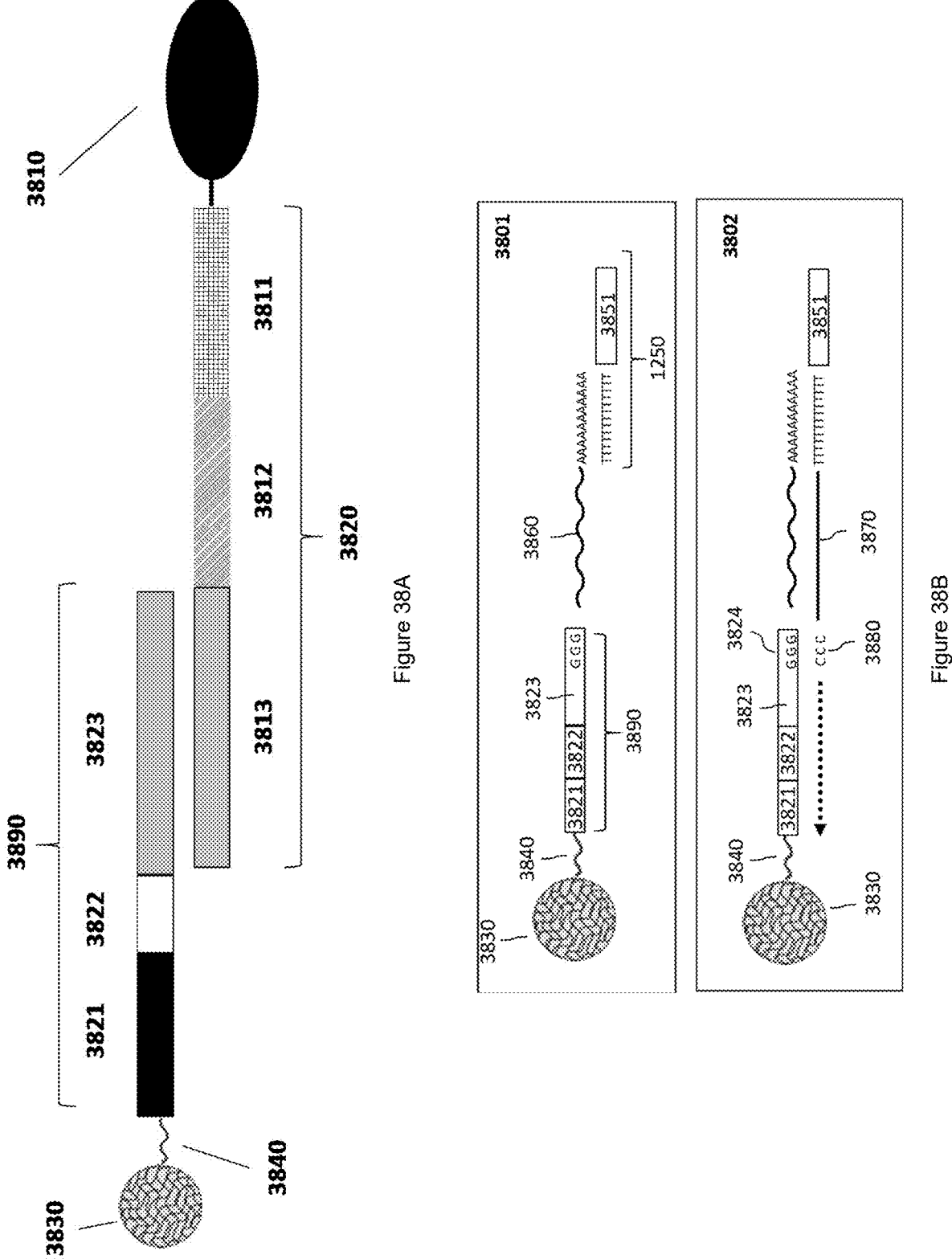
FIGS. 38A, 38B, and 38C illustrate exemplary workflows in accordance with various embodiments of the present disclosure.

In some instances, analysis of one or more analytes (e.g., using the labelling agents described herein) comprises a workflow as generally depicted in FIG. 38A. For example, in some embodiments, cells are contacted with one or more reporter oligonucleotide 3820 conjugated labelling agents 3810 (e.g., polypeptide, antibody, or pMHC molecule or complex) and optionally further processed prior to barcod-ing. Optional processing steps may include one or more washing and/or cell sorting steps. In some instances, a cell bound to labelling agent 3810 (e.g., polypeptide, antibody, or pMHC molecule or complex) conjugated to oligonucle-otide 3820 and support 3830 (e.g., a bead, such as a gel bead) comprising nucleic acid barcode molecule 1290 are parti-tioned into a partition amongst a plurality of partitions (e.g., a droplet of a droplet emulsion or a well of a micro/nanowell array). In some instances, the partition comprises at most a single cell bound to labelling agent 3810. In some embodi-ments, nucleic acid barcode molecule 3890 is attached to support 3830 via a releasable linkage 3840 (e.g., comprising a labile bond).

With continued reference to FIG. 38A, in some embodi-ments, reporter oligonucleotide 3820 conjugated to labelling agent 3810 (e.g., polypeptide, an antibody, pMHC molecule such as an MHC multimer, etc.) comprises a first adapter sequence 3811 (e.g., a primer sequence), a barcode sequence 3812 that identifies the labelling agent 3810 (e.g., the polypeptide, antibody, or peptide of a pMHC molecule or complex), and an adapter sequence 3813. Adapter sequence 3813 may be configured to hybridize to a complementary sequence, such as a complementary sequence 3823 present on a nucleic acid barcode molecule 3890, such as those described elsewhere herein. In some instances, nucleic acid barcode molecule 3890 is attached to a support 3830 (e.g., a bead, such as a gel bead), such as those described elsewhere herein. For example, nucleic acid barcode molecule 3890 may be attached to support 3830 via a releasable linkage 3840 (e.g., comprising a labile bond), such as those described elsewhere herein. In some instances, oligonucleotide 3820 comprises one or more additional functional sequences, such as those described above.

Figure 38C:
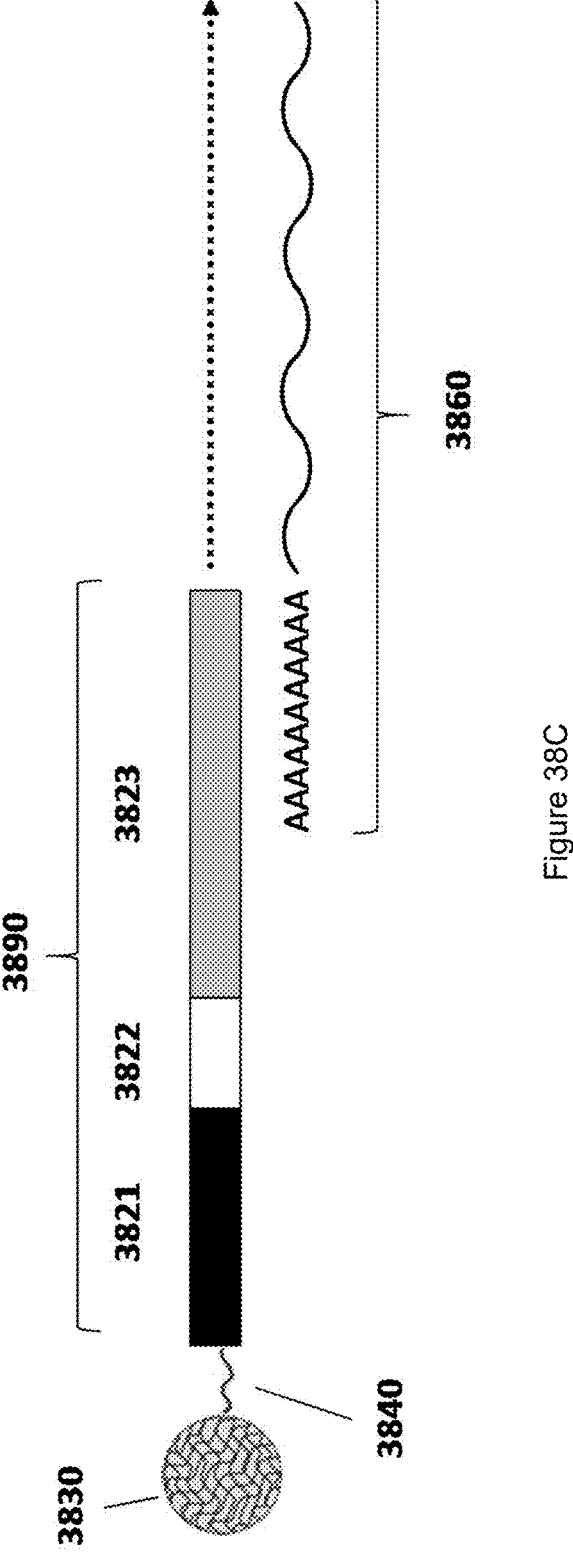

In some instances, analysis of multiple analytes (e.g., RNA and one or more analytes using labelling agents described herein) comprises a workflow as generally depicted in FIGS. 38A-C. Cells are contacted with labeling agents and processed as generally described above and depicted in FIG. 38A. For example, sequence 3813 may then be hybridized to complementary sequence 3823 to generate (e.g., via a nucleic acid reaction, such as nucleic acid extension or ligation) a barcoded nucleic acid molecule comprising cell (e.g., partition specific) barcode sequence 3822 (or a reverse complement thereof) and reporter barcode sequence 3812 (or a reverse complement thereof). Referring to FIGS. 38B-C, in some embodiments, nucleic acid molecules derived from a cell (such as RNA molecules) can be similarly processed to append the cell (e.g., partition-specific) barcode sequence 3822 to these molecules or derivatives thereof (e.g., cDNA molecules). For example, referring to FIG. 38B, in some embodiments, primer 1250 comprises a sequence complementary to a sequence of RNA molecule 3860 (such as an RNA encoding for a BCR sequence) from a cell. In some embodiments, primer 3850 comprises one or more adapter sequences 3851 that are not complementary to RNA molecule 3860. In some embodiments, primer 3850 comprises a poly-T sequence. In some embodiments, primer 3850 comprises a sequence complementary to a target sequence in an RNA molecule. In some embodiments, primer 3850 comprises a sequence complementary to a region of an immune molecule, such as the constant region of a TCR or BCR sequence. Primer 3850 is hybridized to RNA molecule 3860 and cDNA molecule 3870 is generated in a reverse transcription reaction. In some embodiments, the reverse transcriptase enzyme is selected such that several non-templated bases 3880 (e.g., a poly-C sequence) are appended to the cDNA. Nucleic acid barcode molecule 3890 comprises a sequence 3824 complementary to the non-templated bases, and the reverse transcriptase performs a template switching reaction onto nucleic acid barcode molecule 3890 to generate a barcoded nucleic acid molecule comprising cell (e.g., partition specific) barcode sequence 3822 (or a reverse complement thereof) and a sequence of cDNA 3870 (or a portion thereof). In another example, referring to FIG. 38C, in some embodiments, nucleic acid barcode molecule 3890 comprises sequence 3823 complementary to a sequence of RNA molecule 3860 from a cell. In some embodiments, sequence 3823 comprises a sequence specific for an RNA molecule. In some embodiments, sequence 3823 comprises a poly-T sequence. In some embodiments, sequence 3823 comprises a sequence specific for an RNA molecule. In some embodiments, sequence 3823 comprises a sequence complementary to a region of an immune molecule, such as the constant region of a TCR or BCR sequence. Sequence 3823 is hybridized to RNA molecule 3860 and a cDNA molecule 3870 is generated in a reverse transcription reaction generating a barcoded nucleic acid molecule comprising cell (e.g., partition specific) barcode sequence 3822 (or a reverse complement thereof) and a sequence of cDNA 3870 (or a portion thereof). Barcoded nucleic acid molecules can then be optionally processed as described elsewhere herein, e.g., to amplify the molecules and/or append sequencing platform specific sequences to the fragments. See, e.g., U.S. Pat. Pub. 20180105808, which is hereby incorporated by reference in its entirety. Barcoded nucleic acid molecules, or derivatives generated therefrom, can then be sequenced on a suitable sequencing platform.

Figure 39A:
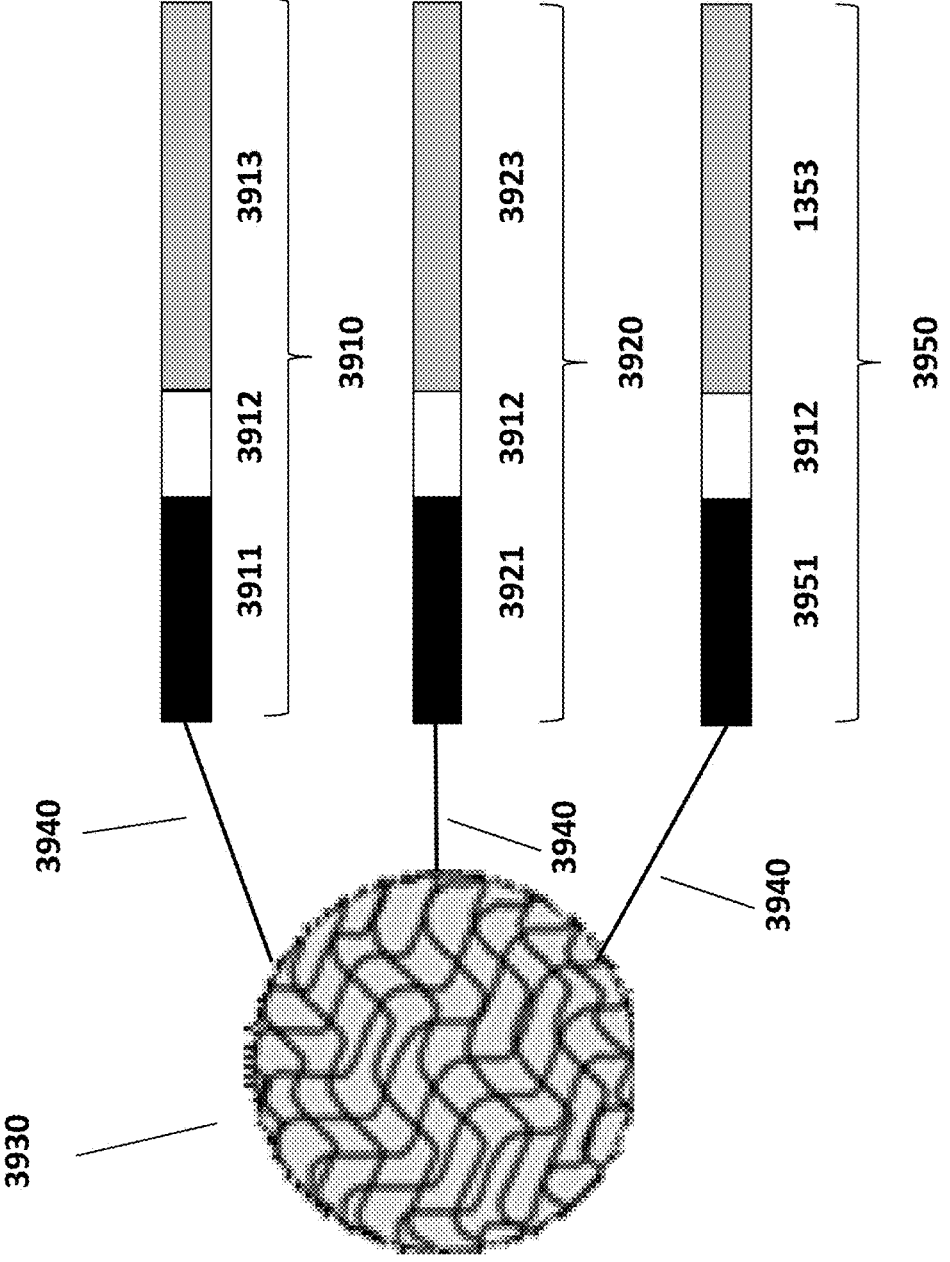
FIGS. 39A, 39B, and 39C illustrate exemplary workflows in accordance with various embodiments of the present disclosure.
Figures 39B, 39C:
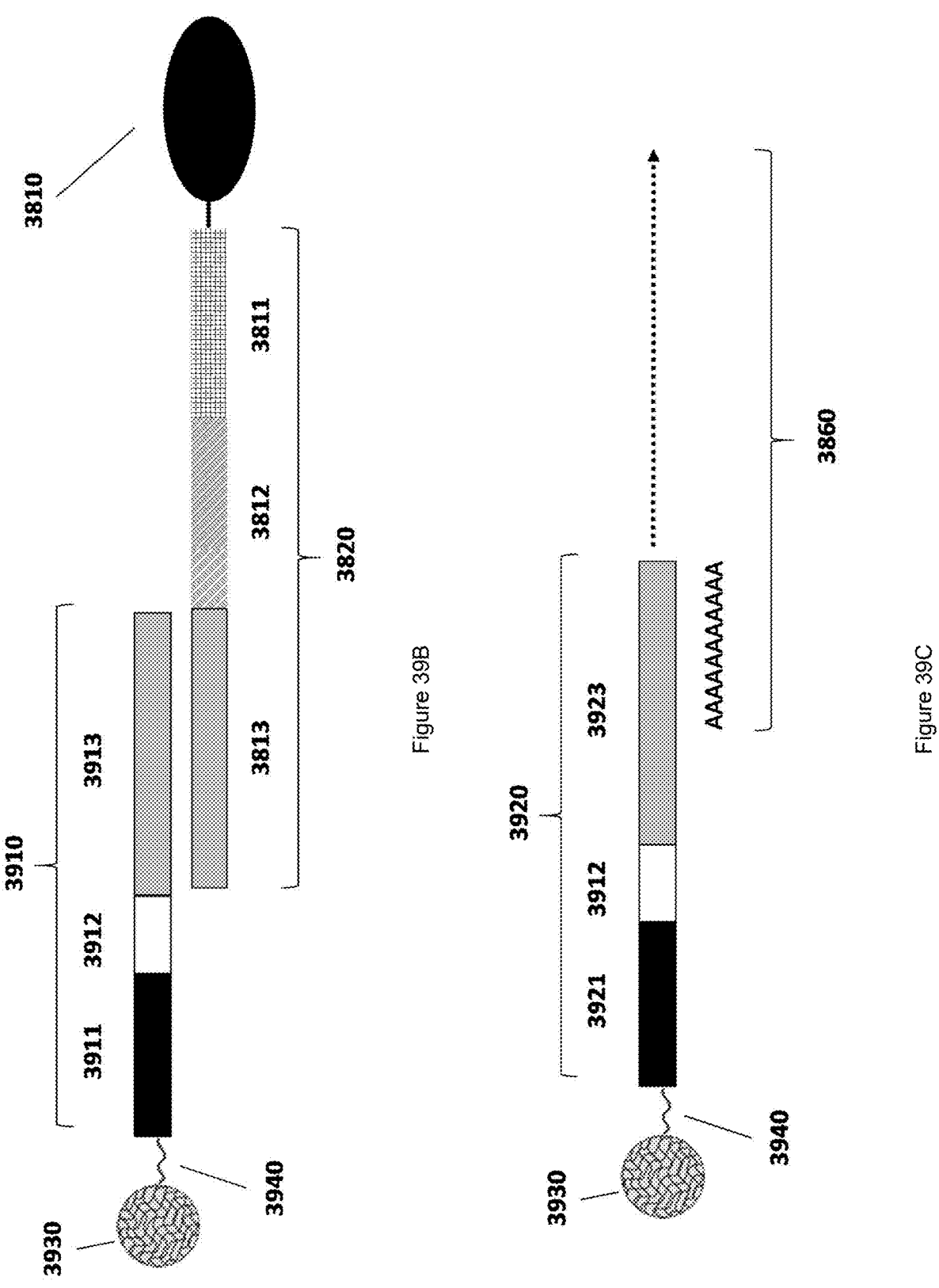

In some embodiments, analysis of multiple analytes (e.g., RNA and one or more analytes using labelling agents described herein) comprises a workflow as generally depicted in FIGS. 39A-C. For example, in some embodiments, cells are contacted with one or more reporter oligonucleotide 3920 conjugated labelling agents 3910 (e.g., polypeptide, antibody, or pMHC molecule or complex) and optionally further processed prior to barcoding. Optional processing steps may include one or more washing and/or cell sorting steps. In some instances, a cell bound to labelling agent 3910 (e.g., polypeptide, antibody, or pMHC molecule or complex) conjugated to oligonucleotide 3920 and support 3930 (e.g., a bead, such as a gel bead) comprising nucleic acid barcode molecules 3910 and 3920 comprising common barcode sequence 3912 are partitioned into a partition amongst a plurality of partitions (e.g., a droplet of a droplet emulsion or a well of a micro/nanowell array). In some instances, the partition comprises at most a single cell bound to labelling agent 3910. In some embodiments, nucleic acid barcode molecules 3910 and 3920 are attached to support 3930 via a releasable linkage 3940 (e.g., comprising a labile bond) as described elsewhere herein. Nucleic acid barcode molecule 3910 may comprise adapter sequence 3911, barcode sequence 3912 and adapter sequence 3913. Nucleic acid barcode molecule 3920 may comprise adapter sequence 3921, barcode sequence 3912, and adapter sequence 3923, where adapter sequence 3923 comprises a different sequence than adapter sequence 3913. In some instances, adapter 3911 and adapter 3921 comprise the same sequence. In some instances, adapter 3911 and adapter 3921 comprise different sequences. Although support 3930 is shown comprising nucleic acid barcode molecules 3910 and 3920, any suitable number of barcode molecules comprising common barcode sequence 3912 are contemplated herein. For example, in some embodiments, support 3930 further comprises nucleic acid barcode molecule 3950. Nucleic acid barcode molecule 3950 may comprise adapter sequence 3951, barcode sequence 3912 and adapter sequence 3953, where adapter sequence 3953 comprises a different sequence than adapter sequence 3913 and 3923. In some instances, nucleic acid barcode molecules (e.g., 3910, 3920, 3950) comprise one or more additional functional sequences, such as a UMI or other sequences described herein.

Subsequent to partitioning, referring to FIG. 39B, in some embodiments, sequence 3813 is hybridized to complementary sequence 3913 of nucleic acid barcode molecule 3910 to generate (e.g., via a nucleic acid reaction, such as nucleic acid extension or ligation) a barcoded nucleic acid molecule comprising cell (e.g., partition specific) barcode sequence 3912 (or a reverse complement thereof) and reporter barcode sequence 3912 (or a reverse complement thereof). Nucleic acid molecules derived from a cell (such as RNA molecules) can be similarly processed to append the cell (e.g., partition-specific) barcode sequence 3912 to these molecules or derivatives thereof (e.g., cDNA molecules). For example, referring to FIG. 39C, in some embodiments, nucleic acid barcode molecule 3920 comprises sequence 3923 complementary to a sequence of RNA molecule 3860 from a cell. In some embodiments, sequence 3923 comprises a poly-T sequence. In other embodiments, sequence 3923 comprises a sequence complementary to a target sequence in an RNA molecule. In some embodiments, sequence 3923 comprises a sequence complementary to a region of an immune molecule, such as the constant region of a TCR or BCR sequence. Sequence 3923 is hybridized to RNA molecule 3860 and a barcoded cDNA molecule is generated in a reverse transcription reaction comprising cell (e.g., partition specific) barcode sequence 3923 (or a reverse complement thereof) and a cDNA sequence corresponding to mRNA 3860 (or a portion thereof). Barcoded nucleic acid molecules can then be optionally processed as described elsewhere herein, e.g., to amplify the molecules and/or append sequencing platform specific sequences to the fragments. See, e.g., U.S. Pat. Pub. 20180105808, which is hereby incorporated by reference in its entirety. Barcoded nucleic acid molecules, or derivatives generated therefrom, can then be sequenced on a suitable sequencing platform.

Block 3604. Referring to block 3604 of FIG. 36A, in some embodiments the population of cells is from a single subject. In other embodiments the population of cells is pooled from a plurality of subjects (e.g., two or more, three or more, or five or more subjects).

Block 3606. Referring to block 3606 of FIG. 36A, in some embodiments the population of cells consists of B cells. In other embodiments, the population of cells comprises both B cells and cells that are not B cells. For example, in some embodiments the population of cells comprises both B cells and T cells. As another example, in some embodiments the population of cells comprises B cells and cells that are not antigen-specific to any of the immunogenic features. As yet another example, in some embodiments the population of cells comprises B cells of varying affinities to 1 or more immunogenic features. In some embodiments, the population comprises a mixture of B cells with different affinities for various antigens.

Block 3608. Referring to block 3608 of FIG. 36A, in some embodiments the population of cells consists of T cells. In other embodiments, the population of cells comprises both T cells and cells that are not T cells. For example, in some embodiments the population of cells comprises T cells and cells that are not immunogenic. In some embodiments, the population comprises a mixture of T cells with different affinities for various antigens.

Block 3609. Referring to block 3609 of FIG. 36A, in some embodiments the corresponding count of the respective immunogenic feature bound to each immune cell in the population of cells is acquired through flow cytometry, active droplet-sorting microfluidics, mass cytometry, or high-content imaging cytometry.

Flow cytometry is a single-cell measurement technique that traditionally offers high-throughput measurements (~10,000-100,000 cells/sec), typically with ~10 or more features (cell-surface markers and intracellular proteins). Integrated with high-speed imaging techniques, imaging flow cytometry has emerged with the concurrent boost in measurable parameters and throughput because of its ability to allow high-resolution single-cell image-based phenotyping without compromising the throughput significantly. See, Caicedo et al., 2017, "Data-analysis strategies for image-based cell profiling," Nature Methods 14 (9), pp. 849-863; and Blasi et al. 2016, "Label-free cell cycle analysis for high-throughput imaging flow cytometry," Nat. Commun. 7:10256 doi: 10.1038/ncomms10256; and Lee et al., 2019, "Multi-ATOM: Ultrahigh-throughput single-cell quantitative phase imaging with subcellular resolution," Journal of Biophotonics doi.org/10.1002/jbio.201800479, each of which is hereby incorporated by reference.

Example active droplet-sorting microfluidics are disclosed in U.S. Pat. Nos. 10,053,723; 10,071,377; 10,137, 449; 10,150,117; 10,221,442; 10,343,166; 10,400,235; and 10,428,326, each of which is hereby incorporated by reference.

Mass cytometry by time of flight (CyTOF) offers single-cell measurements of millions of cells with simultaneous detection of forty or more proteins (features) for a given experiment albeit often at a lower throughput compared to flow cytometry. See, Spitzer and Nolan, 2016, "Mass Cytometry: Single Cells, Many Features," Cell 165(4), pp. 780-91, which is hereby incorporated by reference.

High content image cytometry is described in De Vos, 2010, "High content image cytometry in the context of subnuclear organization," Cytometry Part A 77A, pp. 64-75, which is hereby incorporated by reference.

In some embodiments the corresponding count of the respective immunogenic feature bound to each immune cell in the population of cells is acquired through high content screening (HCS) or automated microscope-based screening measurements of biological activity in single cells. In such embodiments, multiple features of the cell are measured with one or more fluorescent dyes leading to the term high content. HCS is interchangeably referred to as high content analysis (HCA), high content imaging (HCI) or image cytometry (IC). Generally, HCA, HCI and IC refer to lower throughput automated microscope based assays (<100,000 samples or data points), although HCA sometimes refers to the analysis portion of HCS. In contrast to traditional HTS, which has a single read out of activity, HCS allows for measurement of many properties or features of individual cells at once. See, Buchser et al., 2012 (Updated 2014 Sep. 22), "Assay Development Guidelines for Image-Based High Content Screening, High Content Analysis and High Content Imaging," In: Sittampalam et al., editors, Assay Guidance Manual [(Internet) Bethesda (MD): Eli Lilly & Company and the National Center for Advancing Translational Sciences available at ncbi.nlm.nih.gov/books/NBK100913/, which is hereby incorporated by reference.

Blocks 3610-3612. Referring to block 3610 of FIG. 36A, in some embodiments the at least 1,000 immune cells are B cells, and the first immunogenic feature is associated with B cells. Referring to block 3612 of FIG. 32A, in some embodiments the first immunogenic feature is CD19, CD20, CD79a, or PAX5.

Blocks 3614-3618. Referring to block 3614 of FIG. 36A, in some embodiments the at least 100, 500, or 1000 immune cells are T cells, and the first immunogenic feature is associated with T cells. Referring to block 3616 of FIG. 36A, in some embodiments the first immunogenic feature is MHC tetramer, peptide-MHC tetramer, MHC dextramer, peptide-MHC dextramer, or a peptide-MHC multimer of higher order. Referring to block 3618 of FIG. 36A, in some embodiments the first immunogenic feature is CD3 or CD8a.

Block 3620. Referring to block 3618 of FIG. 36A, in some embodiments the first immunogenic feature is a tumor antigen.

In some embodiments, the first immunogenic feature is a marker that is presented on the surface of cells in the population of cells. For instance, in some embodiments, the first immunogenic feature is a cell surface glycolipid or glycoprotein. In some embodiments, the first immunogenic feature is a cell surface protein. In some embodiments, the first immunogenic feature is CDH17, CD138, a members of the integrin family, SEZ6L2, epidermal growth factor receptor (EGFR), or HER2. See Hong, 2018, "QSurface: fast identification of surface expression markers in cancer,"

BMC Syst Biol. 12 (Suppl 2): 17, doi: 10.1186/s12918-018-0541-6, which is hereby incorporated by reference.

In some embodiments, the first immunogenic feature is a tumor-associated antigenic peptide. For instance, in some embodiments the first immunogenic feature is a peptide with a HLA-binding motif inside a protein of interest, such as proteins encoded by mutated oncogenes or genes that are either selectively expressed or overexpressed by tumors. In such embodiments, the tumor-associated antigenic peptide is pulsed onto the population of cells prior to obtaining the measurement of the corresponding count of the respective immunogenic feature for the representation. See, for example, Vigneron, 2015 "Human Tumor Antigens and Cancer Immunotherapy," Biomed Res Int. 948501. doi: 10.1155/2015/948501, which is hereby incorporated by reference.

Block 3622. Referring to block 3622 of FIG. 36A, in some embodiments the population of cells comprises at least 3,000, at least 5,000, at least 10,000, or at least 40,000 cells. In some embodiments, the population of cells comprises two or more different cell types, three or more different cell types, four or more different cell types, or five or more different cell types.

Block 3624. Referring to block 3622 of FIG. 36A, in some embodiments the plurality of immunogenic features comprises at least 40 immunogenic features, at least 60 immunogenic features, at least 80 immunogenic features, at least 100 immunogenic features, or at least 200 immunogenic features.

Blocks 3626-3628. Referring to block 3626 of FIG. 36B, in some embodiments each feature in the plurality of features is a cell surface feature. Referring to block 3628 of FIG. 36B, in some embodiments each cell surface feature is a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T cell receptor, a T cell receptor, a B cell receptor, a chimeric antigen receptor, a fusion protein or other small or large protein, a gap junction, or an adherens junction.

Block 3630. Referring to block 3630 of FIG. 36B, in some embodiments the representation for each representative immunogenic feature in the plurality of immunogenic features, is collectively in the form of a two-dimensional/x m features matrix, where/is a positive integer of 100 or greater, 200 or greater, 500 or greater or 1000 or greater that represents the number of cells in the population of cells, m is a positive integer of 2 or greater, 3 or greater, 4 or greater, 5 or greater, 10 or greater, or 20 or greater that represents the number of immunogenic features, and each element in the matrix uniquely represents a different feature in the plurality of features and a different cell in the population of cells and provides a count of the number of the different feature (or proxy thereof) that has been detected as bound to or presented by the different cell.

Figure 13:
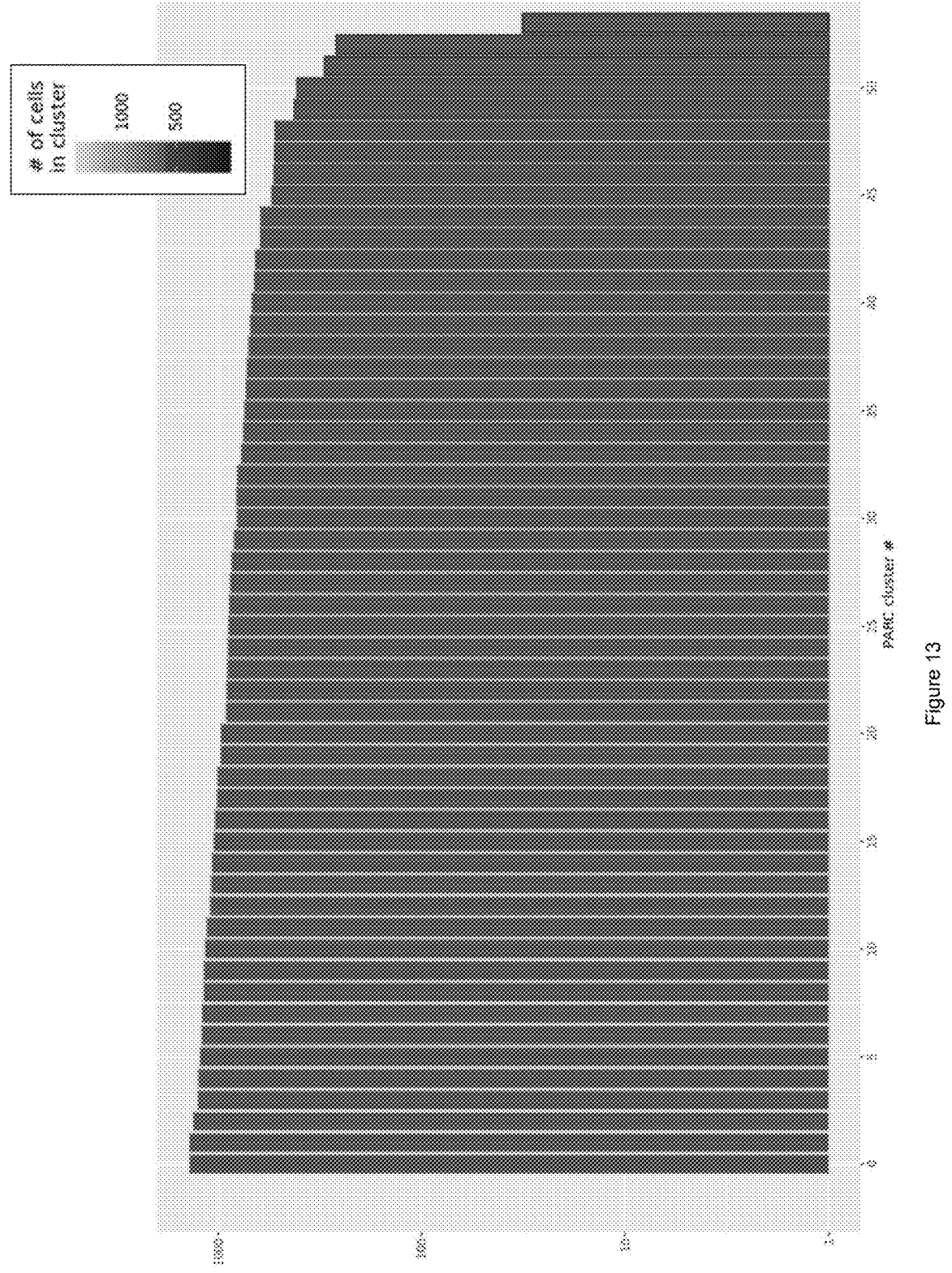
FIG. 13 illustrates the number of cells in each cluster in a plurality of clusters that were obtained upon clustering a population of cells based on the number and types of markers presented by such cells in accordance with an embodiment of the present disclosure.

Block 3632-3636. Referring to block 3632 of FIG. 36B, in some embodiments the plurality of immune cells are clustered using the representation, thereby obtaining a plurality of clusters. Each cluster in the plurality of clusters includes a different subset of the population of cells. FIG. 13 illustrates the result of such clustering, in which a population of cells has been clustered into 53 clusters. Each of the 53 clusters consists of a different subset of the population of cells and the clusters are formed based on the unique distribution of the counts of the various immunogenic features in the plurality of immunogenic features for which measurement data is available.

For clustering in accordance with one embodiment of the systems and methods of the present disclosure, consider the case in which there are measurements for ten immunogenic features for each cell. In such instances, each cell can be expressed as a vector:

$$\vec{X}_{10}=\{x_1, x_2, x_3, x_4, x_5, x_6, x_7, x_8, x_9, x_{10}\}$$

where each $x_i$ is the count of the number of a respective feature that has been detected as bound to or presented by the cell. Thus, consider the case where the population comprises one thousand cells. In this case, 1000 vectors are defined. Those cells that exhibit similar measurement values across the set of immunogenic features will tend to cluster together. In some embodiments, the vectors are reduced in dimension prior to clustering using any of a number of dimensional reduction algorithms such as a linear dimension reduction algorithm or a non-linear dimension reduction algorithm. In some embodiments, the dimension reduction algorithm is principal component analysis algorithm, a factor analysis algorithm, Sammon mapping, curvilinear components analysis, a stochastic neighbor embedding (SNE) algorithm, an Isomap algorithm, a maximum variance unfolding algorithm, a locally linear embedding algorithm, a t-SNE algorithm, a non-negative matrix factorization algorithm, a kernel principal component analysis algorithm, a graph-based kernel principal component analysis algorithm, a linear discriminant analysis algorithm, a generalized discriminant analysis algorithm, a uniform manifold approximation and projection (UMAP) algorithm, a LargeVis algorithm, a Laplacian Eigenmap algorithm, or a Fisher's linear discriminant analysis algorithm. See, for example, Fodor, 2002, "A survey of dimension reduction techniques," Center for Applied Scientific Computing, Lawrence Livermore National, Technical Report UCRL-ID-148494; Cunningham, 2007, "Dimension Reduction," University College Dublin, Technical Report UCD-CSI-2007-7, Zahorian et al., 2011, "Nonlinear Dimensionality Reduction Methods for Use with Automatic Speech Recognition," Speech Technologies. doi: 10.5772/16863. ISBN 978-953-307-996-7; and Lakshmi et al. (18 Aug. 2016). 2016 IEEE 6th International Conference on Advanced Computing (IACC). pp. 31-34. doi: 10.1109/IACC.2016.16, ISBN 978-1-4673-8286-1, each of which is hereby incorporated by reference.

Clustering is described on pages 211-256 of Duda and Hart, *Pattern Classification and Scene Analysis,* 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples (here, cells) in the same cluster will be significantly less than the distance between samples in different clusters. However, as stated on page 215 of Duda 1973, clustering does not require the use of a distance metric. For example, a nonmetric similarity function s (x, x') can be used to compare two vectors x and x'. Conventionally, s (x, x') is a symmetric function whose value is large when x and x' are somehow "similar." An example of a nonmetric similarity function s (x, x') is provided on page 216 of Duda 1973.

Once a method for measuring "similarity" or "dissimilarity" between points (here cells) in a dataset has been selected, clustering requires a criterion function that measures the clustering quality of any partition of the data. Partitions of the dataset that extremize the criterion function are used to cluster the data. See page 217 of Duda 1973. Criterion functions are discussed in Section 6.8 of Duda 1973.

More recently, Duda et al., *Pattern Classification*, Second edition, John Wiley & Sons, Inc. New York, which is hereby incorporated by reference, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (Third Edition), Wiley, New York, N.Y.; and Backer, 1995, Computer-Assisted Reasoning in Cluster Analysis, Prentice Hall, Upper Saddle River, N.J. Particular exemplary clustering techniques that can be used in the systems and methods of the present disclosure to cluster a plurality of representations, where each respective representation is in the form of a vector and comprises the corresponding count of each respective immunogenic feature in the plurality of immunogenic features bound to or presented by a cell corresponding to the respective representation includes but is not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, negative matrix factorization, and Jarvis-Patrick clustering.

Thus, in some embodiments, the representations are clustered thereby assigning each respective cell in the population of cells to a corresponding cluster 185 in a plurality of clusters.

In one embodiment of the present disclosure, k-means clustering is used. The goal of k-means clustering is to cluster the representations based upon the corresponding counts of the respective immunogenic features bound to or presented by each cell in the population of cells. In some such embodiments, the value k for the k-means clustering is a number between 2 and 100 inclusive meaning that the k-means clustering forces the population into k clusters. In some embodiments, the value k is set to a predetermined number such as 10. In some embodiments, the number k is optimized for a particular populations of cells. In some embodiments, a user sets the number k used for the clustering of the population of cells. In some embodiments, no predetermined number of clusters is selected. Instead, clustering is performed until predetermined convergence criteria are achieved. In embodiments where a predetermined number of clusters is determined, k-means clustering is then initialized with k cluster centers $u_1, \ldots, u_K$ randomly initialized in two-dimensional space. As discussed above, for each respective cell i in the dataset, a vector $X_i$ is constructed of each immunogenic feature measurement value associated with the respective cell. In the case where k is equal to 10, ten such vectors $\vec{X}$ are selected to be the centers of the ten clusters. Then, each remaining vector $\vec{X}_i$, corresponding to the cells that were not selected to be cluster centers, is assigned to its closest cluster center:

$$C_k = \left\{ n: k = \arg_k^{min} \left\| \vec{X}_i - \mu_k \right\|^2 \right\}$$

where $C_k$ is the set of examples closest to $\mu_k$ using the objective function:

$$J(\mu, r) = \sum_{n=1}^{N} \sum_{k=1}^{K} r_{nk} \left\| \vec{X}_i - \mu_k \right\|^2$$

where $\mu_1, \ldots, \mu_K$ are the k cluster centers and $r_{nk} \in \{0, 1\}$ is an indicator denoting whether a cell $\vec{X}_i$ belongs to a cluster k. Then, new cluster centers $\mu_k$ are recomputed (mean/centroid of the set $C_k$):

$$\mu_k = \frac{1}{|C_k|} \sum_{n \in C_k} \vec{X}_i$$

Then, all vectors $\vec{X}_i$, corresponding to the cells are assigned to the closest updated cluster centers as before. This is repeated while not converged. Any one of a number of convergence criteria can be used. One possible convergence criteria is that the cluster centers do not change when recomputed. The k-means clustering computes a score for each respective cell that takes into account the distance between the respective cell and the centroid of the cluster 158 that the respective cell has been assigned.

In typical embodiments, each respective cluster consists of a unique different subset of the population of cells.

The k-means clustering algorithm described herein elucidates like clusters within the data. There is no guarantee that all the clusters represent physiologically significant events. In other words, a priori, it is not known what the cell clusters mean in some instances. What is known is that the algorithm has determined that there are differences between the cells that are in different clusters. The systems and methods of the present disclosure provide tools for determining whether there is any meaning behind the differences between the clusters.

In some embodiments, of the present disclosure, rather than using k-means clustering, a Louvain or Leiden modularity algorithm is used. See, Blondel et al., Jul. 25, 2008, "Fast unfolding of communities in large networks," arXiv: 0803.0476v2 [physical.coc-ph], which is hereby incorporated by reference. In some embodiments, the user can choose a clustering algorithm. In some embodiments, clustering the dataset comprises application of a Louvain modularity algorithm to a map, the map comprising a plurality of nodes and a plurality of edges. In such embodiments, each node in the plurality of nodes represents a cell in the plurality of cells. The coordinates in N-dimensional space of a respective node in the plurality of nodes are a set of immunogenic feature measurement values of the corresponding cell in the population of cells. An edge exists in the plurality of edges between a first node and a second node in the plurality of nodes when the first node is among the k nearest neighboring nodes of the second node in the first plurality of node, where the k nearest neighboring nodes to the second node is determined by computing a distance in the N-dimensional space between each node in the plurality of nodes, other than the second node, and the second node. In some embodiments, the distance is a Euclidean distance. In other embodiments, other distance metrics are used (e.g., Chebyshev distance, Mahalanobis distance, Manhattan distance, etc.). In typical embodiments, the nodes and the edges are not weighted for the Louvain modularity algorithm. In other words, each node and each edge receives the same weight in such embodiments Referring to block 3634 of FIG. 36B, in some embodiments the clustering comprises phenotyping by accelerated refined community-partitioning. See, Stassen et al., 2019, "PARC: ultrafast and accurate clustering of phenotypic data of millions of single cells," bioRxiv preprint doi: org/10.1101/765628, which is hereby incorporated by reference. PARC is built upon a nearest-neighbor graph architecture in which each node is a single cell, connected to a neighborhood of its similar cells by a group of edges. PARC employs three steps to enable data-driven clustering of heterogeneous single-cell data. PARC first constructs the graph based on an accelerated k-nearest-neighbor (k-NN) search using hierarchical small world (HNSW). See, Malkov and Yashunin, 2016, "Efficient and robust approximate nearest neighbor search using Hierarchical Navigable Small World graphs," arXiv: 1603.09320 at arxiv.org/abs/1603.09320, which is hereby incorporated by reference. HNSW-based k-NN search offers logarithmic complexity scaling. Second, data-driven graph pruning (on both local and global scale) is implemented in order to remove extraneous edges guided by the distribution of edges weighted by the Jaccard and Euclidean metric. This step is motivated by the distribution of weights which generally resembles a long-tailed distribution in various single-cell data sets in consideration. Based on histogram analysis, the Jaccard (and also Euclidean) weight for weak (potentially 'spurious') and majority (around median weight) links are similar, conceivably a consequence of the high dimensionality of the data being clustered. The tail thus carries most of the important neighbors, but its high weight score also diminishes the relative difference between weak and majority links. Consequently, the optimization function employed in the subsequent community-detection step sees the weak and majority links as very similar. The detected subcommunities are thus more susceptible to being merged by spurious links due to the "resolution limit"-a common limitation in community detection (Barabasi et. al., 2019, Network Science Communities, Chapter 9 at networksciencebook.com/chapter/9 #introduction9) resulting in undesirable merging of clusters. True communities are considered to have adequate strong and 'majority' level weight neighbors to still emerge as stand-alone clusters even after pruning (evidenced by no excessive fragmentation of communities in the final output). Pruning considerably improves sensitivity to rare but distinct populations. Hence, the data-driven pruning procedure offers a two-fold impact in reducing the sample size of edges and improving the k-NN graph representation of the underlying data structure, both of which improve the subsequent community detection step in speed and robustness. Third, a community-detection approach, the Leiden algorithm (Traag et al., 2019, "From Louvain to Leiden: guaranteeing well-connected communities," Scientific Reports 9:5233 at doi.org/10.1038/s41598-019-41695-z), is employed to partition the large pruned networks in the graph into communities. The Leiden algorithm demonstrates fast computation time, scalability, and minimizes badly connected communities (Id.). The data input to PARC is a matrix of n cells×m dimensions representing n cells single cells, each of which has m dims phenotypes (dimensions) measured by different single-cell technologies, e.g. flow cytometry, CyTOF, scRNA-seq, and imaging cytometry (e.g. multi-ATOM in this study), etc.

Referring to block 3636 of FIG. 36B, in some embodiments the clustering is performed using hierarchical clustering, unsupervised clustering, k-means clustering, fuzzy k-means clustering, or Jarvis-Patrick clustering.

Block 3638. Referring to block 3638 of FIG. 36B, in some embodiments the plurality of clusters is between three and one hundred clusters.

Blocks 3640-3642. Referring to block 3640 and 3642 of FIG. 36B, in some embodiments the clustering has a time complexity of at least $O(n)$ or at least $O (\log n)$, where here n is a product of (i) the number of cells in the population of cells and (ii) a number of immunogenic features in the plurality of immunogenic features. For example, in the case where the number of cells is 1000 cells and the number of features is 20, n would be 20×1000. As discussed above, aspects of PARC perform in $O(\log n)$. For a review of time complexity of various clustering algorithms, as well as clustering algorithms that can be used with the present disclosure see Xu and Tian, 2015, "A Comprehensive Survey of Clustering Algorithms," Ann. Data. Sci. 2 (2) 165-193, which is hereby incorporated by reference.

Block 3644. Referring to block 3644 of FIG. 36C there is obtained, for a respective cluster in the plurality of clusters, a total number of unique immune cell receptor clonotypes detected within the different subset of the plurality of immune cells represented by the respective cluster. Workflows for obtaining, at single-cell resolution, both sequence information (e.g., from cellular mRNA) and a corresponding count of respective immunogenic features bound to or presented by such cells has been described above in conjunction with FIGS. 37 through 39. Moreover, the following discussion, in conjunction with FIGS. 2 through 8, describes how the sequence information can be used to determine the clonotypes for each of the cells. It follows that the total number of unique immune cell receptor clonotypes detected within the different subset of the plurality of immune cells represented by a respective cluster can be derived from such information, e.g., by counting the number of unique immune cell receptor clonotypes across the cells in the different subset of the plurality of immune cells represented by the respective cluster.

Figure 2:
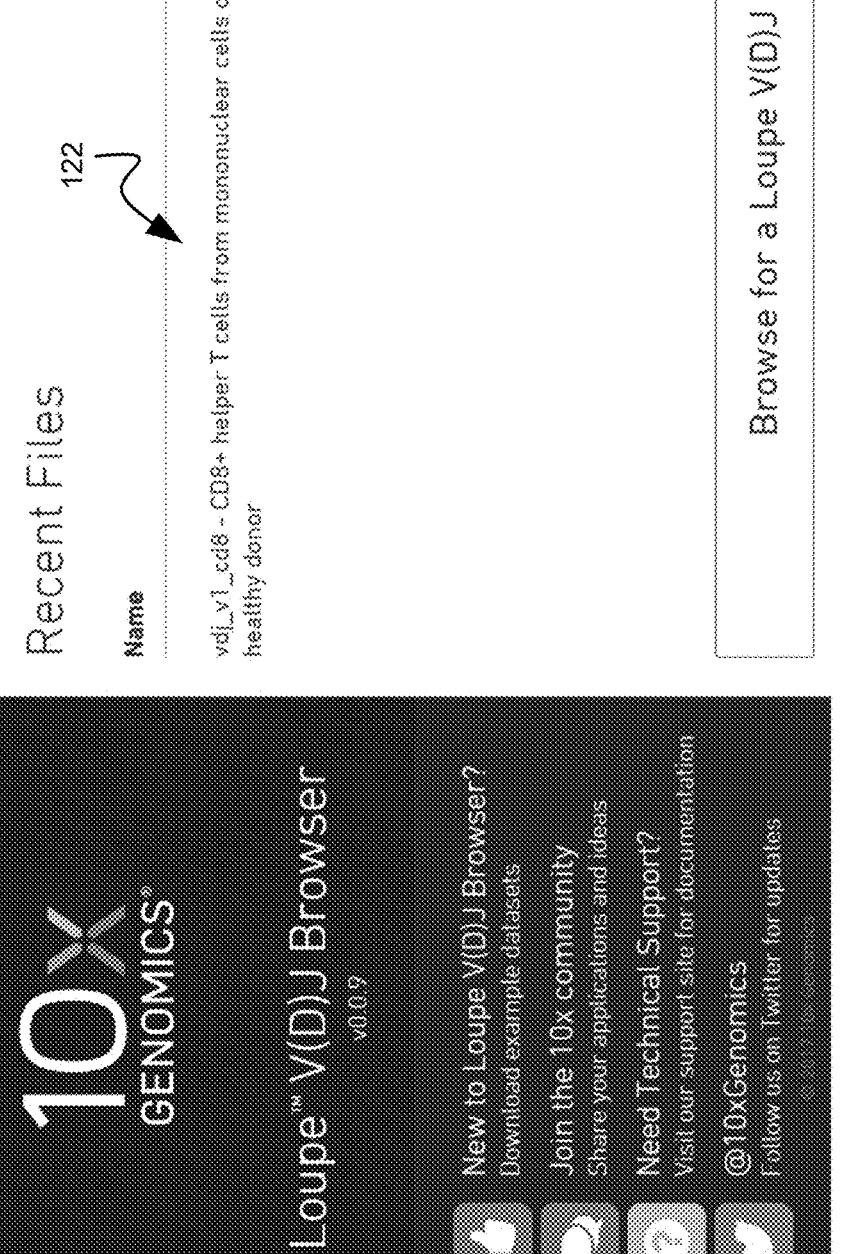
FIG. 2 illustrates a user interface for obtaining a dataset in accordance with some embodiments.
Figure 3:
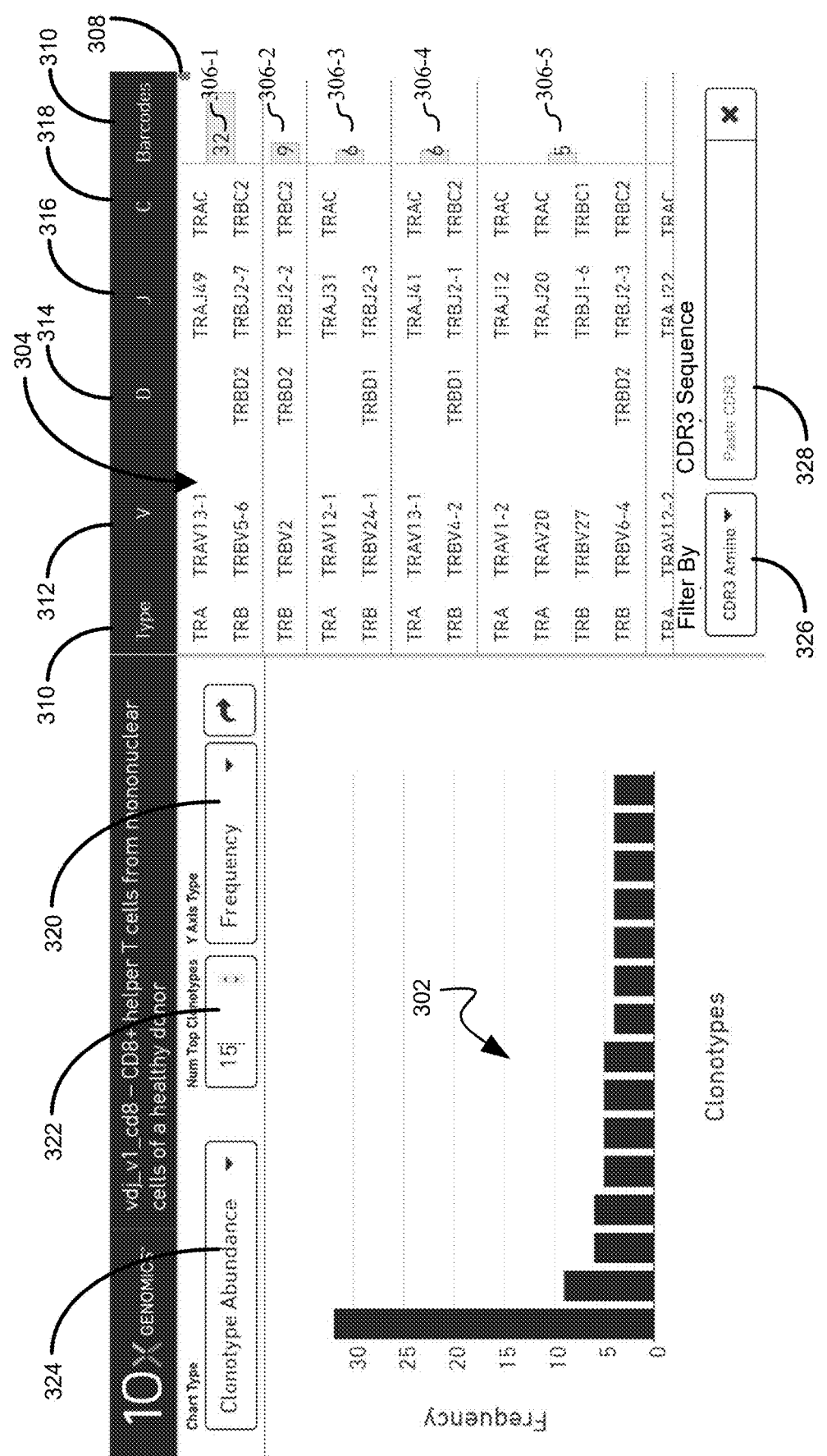
FIG. 3 illustrates an example display for visualizing clonotype abundance as a function of clonotype frequency in a population of cells in accordance with some embodiments.

FIG. 2 illustrates the initial panel that is displayed by a browser module 120 when a user executes the module in some embodiments in order to obtain information about the clonotypes in a dataset comprising a population of cells. In particular, FIG. 2 illustrates how the browser module 120 provides some information regarding a given population of cells such as the name of the dataset, the number of cells that are assumed to be represented by the population of cells, and the last time the dataset was accessed. The number of cells that are assumed to be represented by the dataset is derived by evaluation of the number of unique barcodes that are estimated to be uniquely associated with cells in the dataset. In some embodiments, a respective barcode is deemed to be uniquely associated with a cell if there exists within the dataset a contig that (i) is associated with the respective barcode and (ii) is supported by at least two unique molecular identifiers that each are supported by sequence reads in the data set. In other words, each cell that is assumed to be represented by the dataset is supported within the dataset by a barcode for a contig, where the contig, in turn, is supported by at least two different unique molecular identifiers, where each such unique molecular identifier is, in turn, supported by sequence reads in the dataset. Upon selecting a clonotype dataset, process control turns to the display 302 of FIG. 3. FIG. 3 displays various data from a clonotype dataset. In particular, at a top level, nucleic acid sequences in the VDJ region of cells is organized by clonotypes in some embodiments. In some embodiments, this sequence information, in the form of sequence reads, is obtained using a droplet based single-cell RNA-sequencing (scRNA-seq) microfluidics system that enables 3' or 5' messenger RNA (mRNA) digital counting of thousands of single cells. In such sequencing, droplet-based platform enables barcoding of cells.

The scRNAseq microfluidics system builds on the GemCode technology, which has been used for genome haplotyping, structural variant analysis and de novo assembly of a human genome. See, Zheng et al., 2016 "Haplotyping germline and cancer genomes with high-throughput linked-read sequencing," Nat. Biotechnol. 34, pp. 303-311; Narasimhan et al., 2016, "Health and population effects of rare gene knockouts in adult humans with related parents," Science 352, pp. 474-477 (2016); and Mostovoy et al., 2016, "A hybrid approach for de novo human genome sequence assembly and phasing," Nat. Methods 13, 587-590, each of which is incorporated by reference, for a general description of GemCode technology. Such sequencing uses a gel bead-in-emulsion (GEM).

GEM generation takes place in a multi-channel microfluidic chip that encapsulates single gel beads at a predetermined fill rates, such as approximately 80%. For the clonotype datasets of the present disclosure, in some embodiments, a 5' gene expression protocol is followed rather than a 3' gene expression protocol. In the case where the sample comprises T cells, this provides full-length (5' UTR to constant region), paired T cell receptor (TCR) transcripts from a number of (e.g., 100-10,000) individual lymphocytes per sample. In the case where the sample comprises B cells, this provides full-length (5' UTR to constant region), paired B cell immunoglobulin heavy chain and light chain transcripts from a number of (e.g., 100-10,000) individual lymphocytes per sample.

In some embodiments, as in the case of 3' gene expression protocol described in Zheng et al., id., 5' expression protocol includes partitioning the cells into GEMs. In particular, in some embodiments, single cell resolution is achieved by delivering the cells at a limiting dilution, such that the majority (~90-99%) of generated GEMs contains no lymphocyte (cell), while the remainder largely contain a single lymphocyte. In some embodiments, upon dissolution of the single cell 5' gel bead in a GEM, oligonucleotides containing (i) a read 1 sequencing primer (e.g., ILLUMINA R1 sequence), (ii) a barcode, (iii) a unique molecular identifier (UMI), and (iv) a switch oligonucleotide are released and mixed with cell lysate and a master mix that contains poly(dT) primers. Incubation of the GEMs then produces barcoded, full-length cDNA from poly-adenylated mRNA. After incubation, the GEMs are broken and the pooled fractions are recovered. In some embodiments, magnetic beads (e.g., silane beads) are used to remove leftover biochemical reagents and primers from the post GEM reaction mixture. The barcoded, full-length V(D)J segments from lymphocyte cDNA are enriched by PCR amplification prior to library construction. In some embodiments, enzymatic fragmentation and size selection are used to generate variable length fragments that collectively span the V(D)J segments of the enriched receptor chains prior to library construction.

In some embodiments, R1 (read 1 primer sequence) is added to the molecules during GEM incubation. P5 is added during target enrichment. P7, a sample index and R2 (read 2 primer sequence) are added during library construction via end repair, A-tailing, adaptor ligation and implementation of the polymerase chain reaction (PCR). The resulting single cell V(D)J libraries contain the P5 and P7 primers used in Illumina bridge amplification. See the Internet, at assets.contentful.com/an68im79xiti/ 26tufAiwIOKCYA0ou2gCWK/8d313d2b126a7a1652d13 81073e72015/CG000086_SingleCellVDJReagentKits UserGuide_RevA.pdf, last accessed May 18, 2017, pp. 2-4, which is hereby incorporated by reference. See also, "Multiplexed Sequencing with the Illumina Genome Analyzer System," copyright 2008, on the Internet at www. illumina.com/documents/products/datasheets/datasheet_sequencing_multiplex.pdf, last accessed May 18, 2017, hereby incorporated by reference, for documentation on the P5 and P7 primers. In some embodiments, the sequenced single cell V(D)J library is in the form of a standard ILLUMINA BCL data output folder. In some such embodiments, the BCL data includes the paired-end Read 1 (comprising the barcode, the UMI, the switch oligonucleotide, as well as 5' end of a receptor chain cDNA) and Read 2 (comprising a random part of the of the same receptor chain cDNA) and the sample index in the i7 index read. In some embodiments, a computer program such as the 10× CELL RANGER analysis pipeline performs secondary analysis on the BCL data such as using the barcodes to group read pairs from the same cells, assemble full-length V(D)J segments in the form of contigs, and thereby create the clonotype dataset.

Adaptive immune cell receptors are somatically rearranged in precursor cells. Multiple rearrangements lead to the expression of paired, mature sequences—these pairs constitute the functional immune cell receptor for T cells and B cells, each with its own antigen specificity (the ability of an immune cell to recognize a target via its immune cell receptor). As an immune cell is exposed to and recognizes its target, it proliferates in a process called clonal expansion. In the case of T lymphocytes, this produces daughter cells that carry identical T cell receptors at both the nucleotide and amino acid sequence levels. In the case of B lymphocytes, this produces daughter cells that can bear the same nucleotide and amino acid sequence for the B cell receptor, or different sequences that are mutated from the original progenitor sequence for the B cell receptor. Acquisition of these mutations in B cell receptors is an important biological function that confers enhanced binding affinity, and this affinity maturation is achieved through somatic hypermutation. Thus, many B cell receptors that differ from each other at the nucleotide and amino acid sequence level can recognize the same target, a narrower target set, or a broader target set.

In some embodiments, the multiple sequence reads with the same barcode form at least one contig, and each such contig represents a chain (e.g., T cell receptor α chain, T cell receptor β chain, B cell heavy chain, B cell light chain) of a single cell. In some embodiments, the contig consensus sequence for each of the contigs of a cell are collectively used to determine the clonotype of the cell. Stated differently, sequence reads are grouped by barcode, and contigs are assembled by looking at sequence reads with the same UMI identifier. A set of chain consensus sequences, including a CDR3 region, is created by analyzing the common bases in the contigs. Cells within these consensus sequences are grouped into clonotypes, and bar chart 302 of FIG. 3 shows the number of unique barcodes in each clonotype. That is, FIG. 3 provides a bar chart 302 of the frequency of occurrence of particular clonotypes in the 1955 cells that are in the particular clonotype dataset that is being illustrated by the browser module 120. In this particular dataset, the cells used for sequencing are T cells.

In some embodiments, the clonotype dataset includes the V(D)J clonotype of the T cell receptor of any T cells or B cell immunoglobulins of any B cells that were in the biological sample (population of cells) represented by the clonotype dataset. The clonotypes of T cells and B cells are described below. For more disclosure on clonotype definitions, see Marks and Deane, 2020, "How repertoire data is changing antibody science," The Journal of Biological Chemistry 295, 9823-9837, which is hereby incorporated by reference.

In general, module 120 can be used to analyze clonotyping datasets prepared from T cells or B cells using any of the definitions for clonotypes or any of the algorithms for identifying clonotypes disclosed herein or referenced herein. For example, in the case of T cells, in some embodiments clonotyping identifies the unique nucleotide CDR3 sequences of a T cell receptor chain, which constitute V, D, and J segments. In accordance with the systems and methods of the present disclosure, this generally involves PCR amplification of the mRNA obtained using the above described scRNAseq microfluidics system in which each GEM encapsulates a single cell, employing V-region-specific primers and either constant region (C) specific or J-region-specific primer pairs, followed by nucleotide sequencing of the amplicon, or constant region primers in 5' RACE approach. Various approaches for obtaining clonotype datasets are also disclosed in Rosati, 2017, "Overview of methodologies for T-cell receptor repertoire analysis," BMC Biotechnology 17:61, which is hereby incorporated by reference.

To understand what constitutes members of a clonotype, one can start with the original progenitor cell for a given lineage of B cells, this progenitor cell commonly referred to as the parent clone, which is a single cell to which all daughter cells will be genetically related, though their B cell receptors and exact antigen specificity may differ and diverge over time. Collectively, this parent clone and all its daughter cells constitute a clonotype. Accurate identification of the members of a clonotype is important not just from a biological perspective, but also from the biomedical perspective-correct identification of all of the members of a given clonotype can be useful in the design of vaccines (e.g. what antibody lineages can be expanded by a vaccine or are expanded successfully or unsuccessfully by a vaccine), in the monitoring of B cell mediated immune disease (e.g. myasthenia gravis, lupus, B cell lymphoma), and in other settings. Known approaches that attempt to group immune cell receptor sequences into groups with shared antigen specificity or members of the same clonotype include, but are not limited to: immcantation, Clonify, GLIPH, TCRdist, VDJTools, MiXCR, AbSolve, and the algorithms described in PMID: 23536288, PMID: 23898164, PMID: 25345460, etc.

While some of the above-referenced algorithms can successfully identify groups of T cells with shared antigen specificity using single-cell data (TCRdist, GLIPH), and the other algorithms use solely bulk receptor sequencing data (e.g., without access to heavy and light chain sequences), none of these algorithms attempt to approximate the true clonotypes for B cells while also attempting to mitigate for sources of noise in the data nor while using the additional specificity found in the antibody light chain. Antibody discovery efforts have shown that false-positive antibody candidates are more frequently found in randomly paired antibody libraries than in natively paired antibody libraries, demonstrating the importance of correct clonotype identification from both biological and pharmaceutical perspectives. Both chains of the B cell receptor undergo affinity maturation and somatic hypermutation. Unsurprisingly, both chains of the B cell receptor are known to carry antigen-binding sites that are essential for recognition of a given B cell's (and in some cases, entire B cell lineages') target. The mutations shared by and differing between members of a clonotype can only be accurately identified by considering the full-length sequences from both the heavy and the light chain of each single B cell. Thus, it follows that truly correct identification of the best approximation of a B cell clonotype is performed using paired heavy-light sequences from single B cells and statistical modeling of the genetic processes affecting B cell receptor sequences, including their generation and the processes which lead to the acquisition of mutations in both halves of the B cell receptor. One approach that makes use of this observation in order to construct clonotype datasets is described in U.S. Patent Application No. 61/011,783, entitled "Systems and Methods for Identifying Adaptive Immune Cell Clonotypes," filed Apr. 17, 2020, and on the Internet at Github at 10×Genomics/enclone, last accessed Aug. 31, 2020, each of which is hereby incorporated by reference. Further details of this technique are disclosed in Example 2 below.

In some embodiments, lower resolution definitions of clonotypes are used. For instance, in some embodiments, rather than using the full length VDJ receptor to ascertain clonotypes, only the CDR3 portion of the receptor is used. In fact, the present disclosure can make use of any clonotype definition used in the art.

Sequence reads 134 obtained from mRNA encoding all or portions of a cell receptor chain for an individual cell are used to derive a contig that includes the CDR3 region. Each of the contigs for a given cell will have a common barcode thereby defining the set of contigs for the given cell and, correspondingly, the set of CDR3 sequences for the given cell. The full-length V region and CDR3 region across the set of contig consensus sequences for the given cell thereby determines the clonotype of the cell. Thus, graph 302 represents the frequency of clonotype occurrence across the plurality of cells represented in a clonotype dataset. In the biological sample represented by the clonotype dataset, each clonotype has some number of cells of a particular clonotype. These clonotypes are sorted by frequency of clonotype occurrence. Table 304 lists out the clonotype information that is summarized in graph 304. Each box 306 in table 304 is the clonotype 124 of a particular set of contigs. There may be multiple cells represented by this clonotype in the clonotype dataset 122. For instance, in the biological sample represented by dataset 122, there are 32 T cells that have the clonotype described in box 306-1, 9 T cells that have the clonotype described in box 306-2, 6 T cells that have the clonotype described in box 306-3, 6 T cells that have the clonotype described in box 306-4, and 5 T cells that have the clonotype described in box 306-5.

Clonotype 306-1 includes one contig type for a T cell α chain and another contig type for a T cell β chain. That is, each of the contigs for a T cell α chain for clonotype 306-1 have a same first CDR3 sequence, and each of the contigs for a T cell β chain for clonotype 306-1 have a same second CDR3 sequence. By contrast, clonotype 306-5 includes two contig types for a T cell α chain and another two contig types for a T cell β chain. That is, each of the contigs for a T cell α chain for clonotype 306-1 have either a first or second CDR3 sequence, and each of the contigs for a T cell β chain for clonotype 306-1 have either a third or fourth CDR3 sequence.

Further, toggle 308 can be used to scroll further down in table 304 to reveal the clonotypes and frequency (or number) of additional T cells in the biological sample represented by dataset 122. For each clonotype, table 304 details each chain type 310 represented in the clonotype 124.

Figure 4:
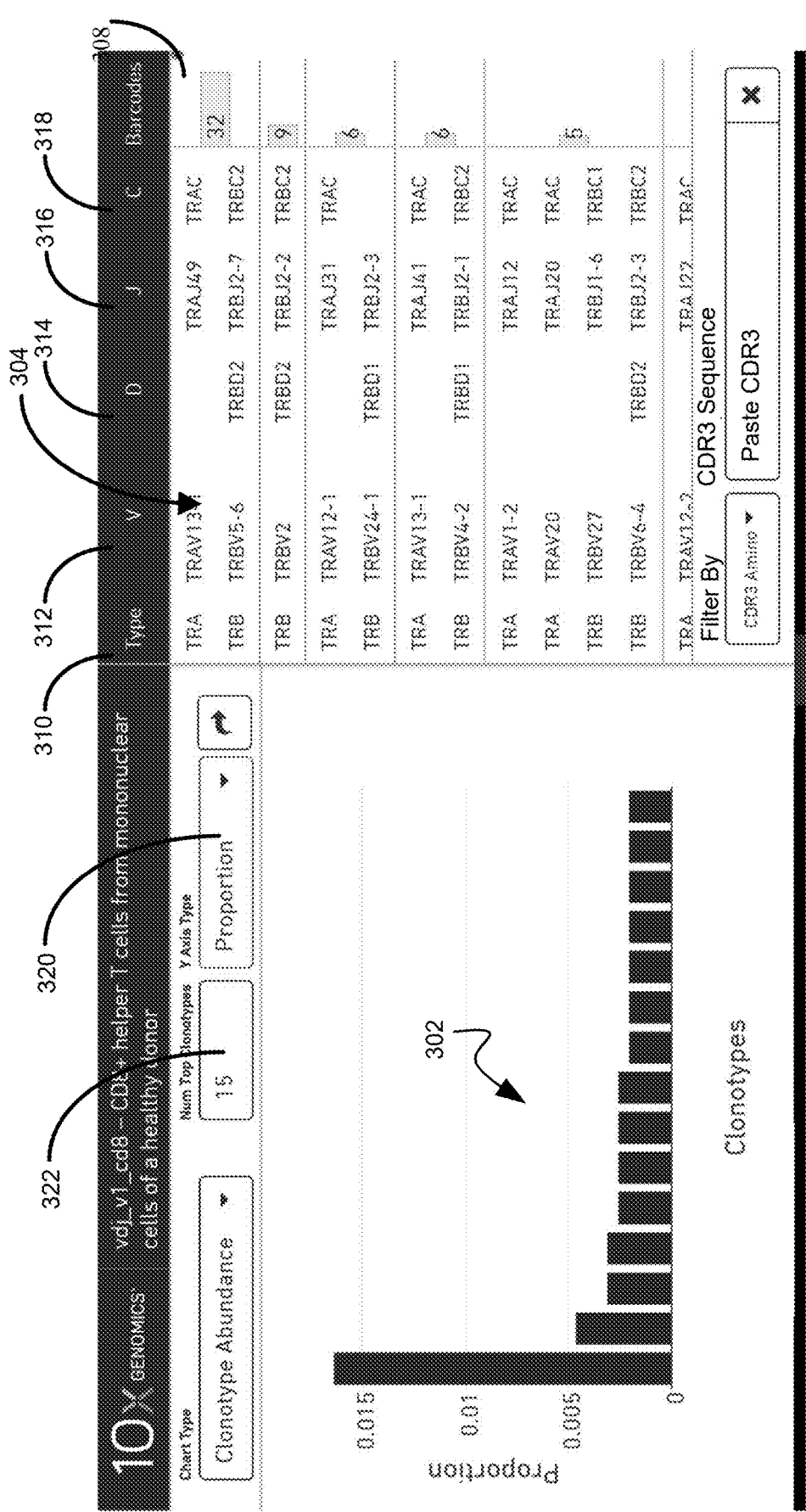
FIG. 4 illustrates an example display for visualizing clonotype abundance as a function of clonotype proportion in a population of cells in accordance with some embodiments.

Advantageously, the clonotype information can be visualized in a variety of different ways. FIG. 3 illustrates a default chart 302 for clonotype dataset 122. Toggle 320 allows for chart 302 to be toggled between displaying (i) frequency in terms of total number of cells per clonotype as illustrated in FIG. 3 and (ii) proportion in terms of total number of cells per clonotype as illustrated in FIG. 4.

Affordance 322 is used to specify the total number of clonotypes, from among all the clonotypes in a clonotype dataset 122 under analysis that are displayed in chart 302 and table 304. Presently, as illustrated in FIG. 3, the top 15 represented clonotypes are under analysis. In some embodiments, the clonotype dataset includes contigs for 50 or more clonotypes, 100 or more clonotypes, 500 or more clonotypes or 1000 or more clonotypes. As such, examination of clonotype frequency of all the clonotypes in the dataset 122 may prove to be too cumbersome in some instances, particularly when considering that most of the least represented clonotypes are present on a unitary basis. Affordance 322 allows the user to optimize the display for various use cases and clonotype datasets 122. The user can use affordance 322 to dial up to the total number of clonotypes in the dataset 122 under analysis or ratchet down the number of clonotypes displayed to a limited number, such as 15, as illustrated in FIG. 3.

Toggle 324 is used to select other chart types that can be applied to the clonotype 124 dataset. For instance, turning to FIG. 5, rather than viewing clonotype abundance in a clonotype dataset 122, V gene usage across the cells of the biological sample used to form the clonotype dataset 122 can be examined. The V gene usage is the annotated V region counted for each of the clonotypes. In other words, V gene usage is an aggregate of all V gene usage of each of the possible different human V genes (e.g., TRAV-1, TRAV4, TRAV8-2, TRAV9-2, etc.) plotted by frequency, regardless of which chain the represented V genes occurs in. Thus, in the case of the V gene TRAV1-1, a count of each instance of this V gene, regardless of occurrence in an α chain or β chain, across the clonotype dataset 122 is provided. Moreover, affordance 322 can now be used to select chain type (e.g., α chain only, β chain only, both α chain and β chain, etc. in the case of T cells, heavy chain only, light chain only, both heavy chain and light chain, etc., in the case of B cells). For instance, if affordance 322 is changed to α chain only, graph 502 only displays the frequency of occurrence of each V gene type across the α chains that occur in the clonotype dataset 122.

In some embodiments, if a cell represented in the clonotype dataset does not have a V region or a J region, it is filtered out of the provided views. This occurs in some instances. The VDJ region is about 700 bases in length whereas, in some embodiments, the sequence reads 134 are about 150 base pairs long. Therefore, situations arise in which some mRNA molecules encoding the VDJ region only get sequence reads on one part of the VDJ region (V only or J only) and not the other part of the VDJ region and so the V region or the J region is not represented for such mRNA molecules. In such instances, it is not possible to determine the clonotype of such cells. In some instances, in order to have an assigned clonotype, some embodiments of the present disclosure impose the condition that there has to be within a single cell a read with a particular UMI code that aligns to a V gene and another read with the particular UMI code that aligns to a J gene. In the alternative, longer sequence reads are employed that align to the entire VDJ region. In the alternative still, sequence reads having the same UMI are employed that collectively align to the entire VDJ region.

Figure 5:
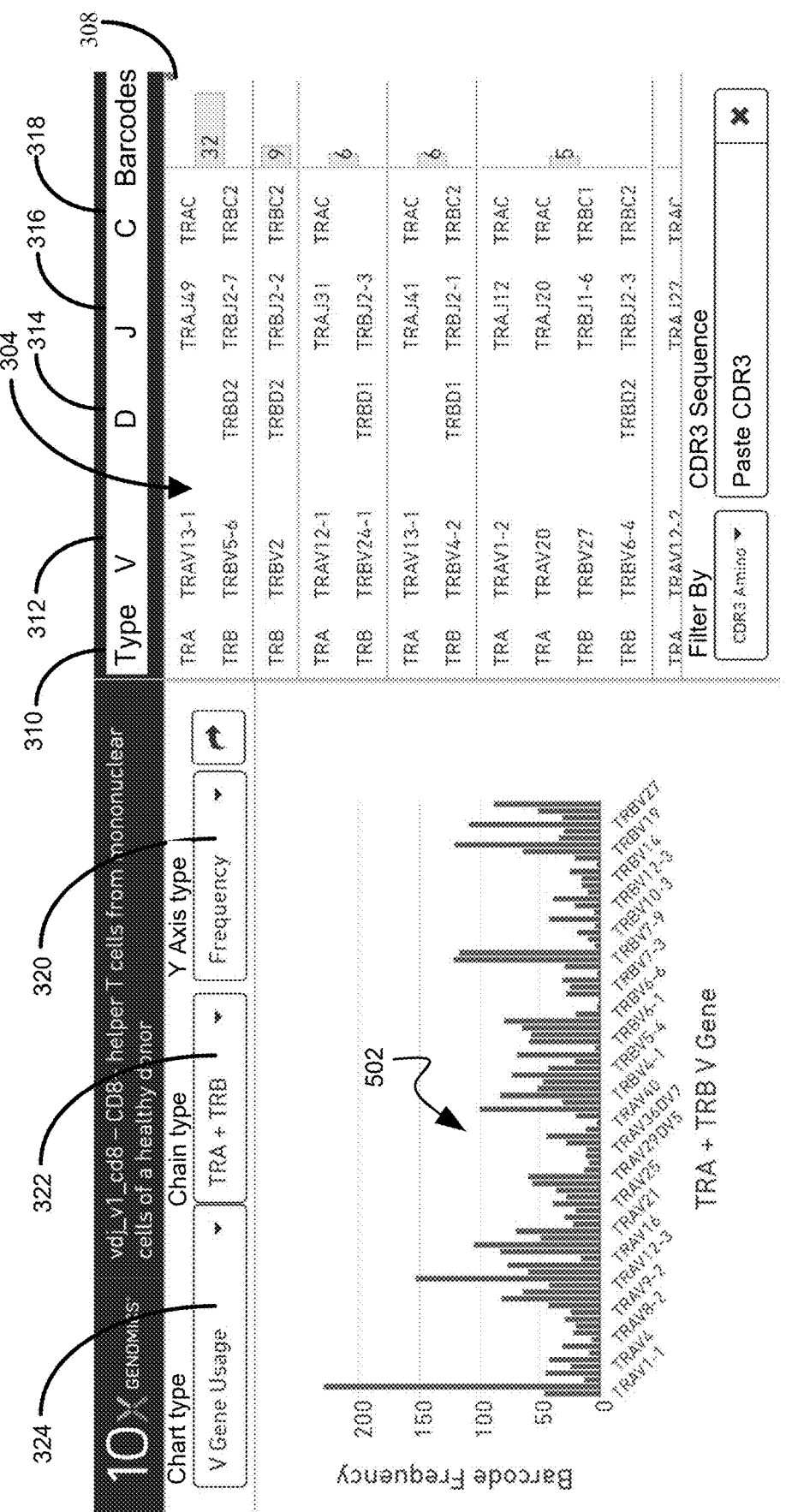
FIG. 5 illustrates an example display for visualizing V region usage across T cell receptor α chains and T cell receptor β chains in a population of cells in accordance with some embodiments.

The advantage of the clonotype data illustrated in FIGS. 3 and 4 is that all the components (V, D, J) contributing to clonotypes have been robustly paired. However, FIG. 5 shows how the VDJ browser can be used to analyze components of a clonotype. FIG. 5 illustrates specific V region usage in a clonotype dataset. This is advantageous because immunologists are used to analyzing data in this manner as traditionally they have not had mechanisms for robustly pairing all the components of a clonotype. Thus, an immunologist can use toggle 324 to examine V region usage across a clonotype dataset 122 or J region usage across a clonotype dataset 122 independently of how such V regions or J regions have been incorporated into clonotypes for suitable legacy purposes. In this way, workers can compare clonotype datasets 122 to older experiments (e.g., for validation or comparative purposes).

Figure 6:
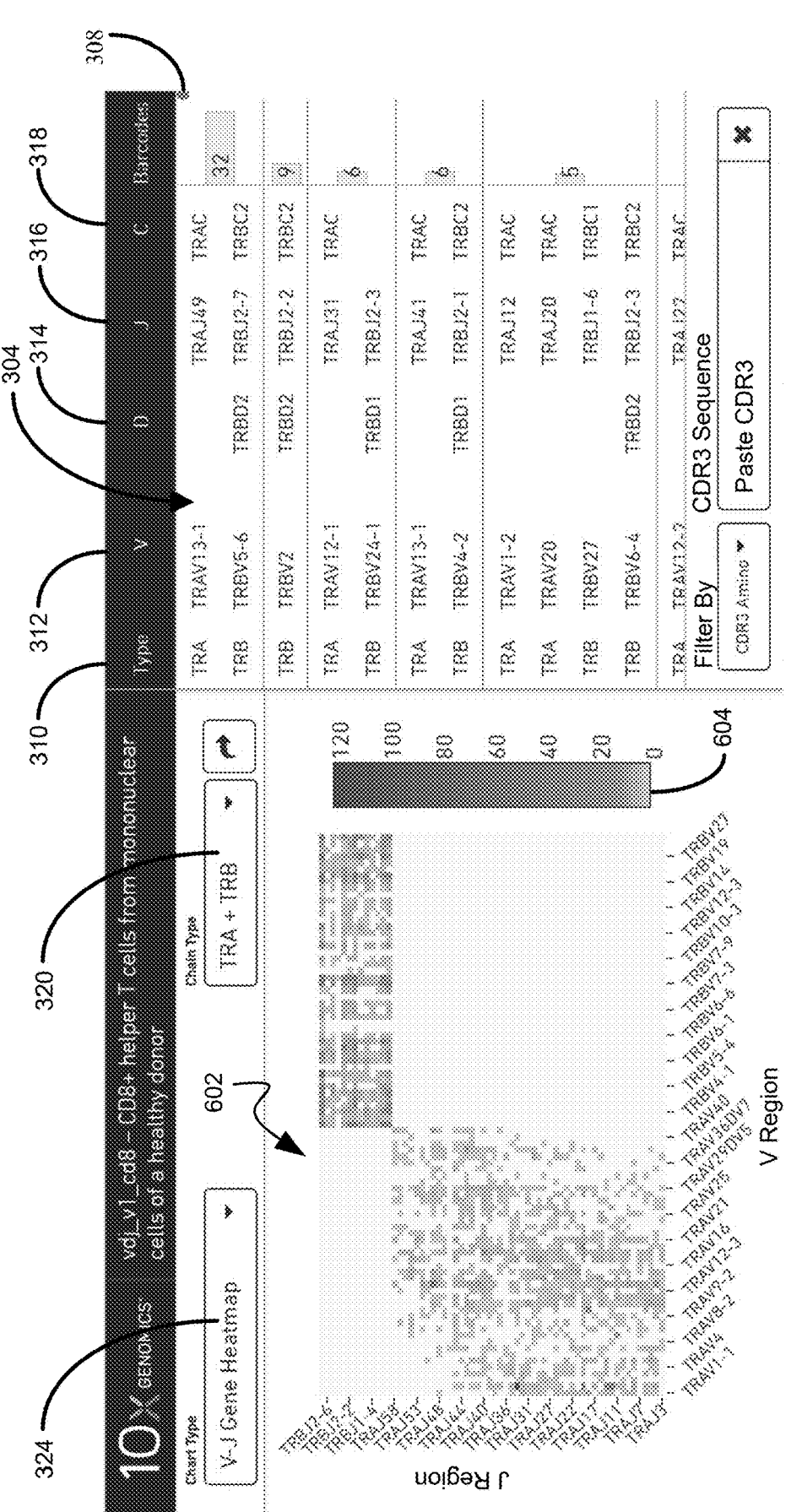
FIG. 6 illustrates an example display for visualizing the number of particular V region/J region pairs of individual T cell receptor a chains and T cell receptor β chains in a population of cells represented by a clonotype dataset in accordance with some embodiments.

Turning to FIG. 6, another chart type 602 that can be used to analyze a clonotype dataset 122 is disclosed. Chart type 602 provides a heat map of V and J region usage across the VDJ sequence of lymphocyte receptor chains in a population of cells represented by the clonotype dataset 122. For instance, in the case of T cells, chart type 602 provides a heat map of V and J region usage across the VDJ sequence of T cell receptor α chains and T cell receptor β chains in a population of cells represented by the clonotype dataset 122. In the case of B cells, chart type 602 provides a heat map of V and J region usage across the V(D)J sequence of B cell immunoglobulin heavy chains and B cell immunoglobulin light chains in a population of cells represented by the clonotype dataset 122.

As noted above, each chain has a V region 312 and a J region 316. Each x-y cell in the heat map of chart 602 provides an indication of the number of contigs present in the clonotype dataset 122 whose CDR3 region contains a receptor chain that contains a corresponding pair of a respective V region and a respective J region from among the V regions and J regions represented. For instance, in the case of B cells, each x-y cell in the heat map of chart 602 provides an indication of the number of contigs present in the clonotype dataset 122 whose CDR3 region contains a heavy chain or a light chain that contains a corresponding pair of a respective V region and a respective J region from among the V regions and J regions represented. In the case of T cells, each x-y cell in the heat map of chart 602 provides an indication of the number of contigs present in the clonotype dataset 122 whose CDR3 region contains an α chain or a β chain that contains a corresponding pair of a respective V region and a respective J region from among the V regions and J regions represented. Turning to FIG. 6 to illustrate, one x-y cell in the chart 602 indicates the number of contigs present in the clonotype dataset 122 that contains a TRAV-1-1 V region and a TRAJ3 J region.

Accordingly some embodiments of the present disclosure provide a second two-dimensional visualization (602) while maintaining the listing of the plurality of clonotypes (304). The second two-dimensional visualization (602) provides a first filter (324) for selection of a pair of genes of a lymphocyte receptor represented by the dataset. The second two-dimensional visualization (602) provides a second filter (320) for one or more chain types. A first axis of the second two-dimensional visualization represents a first individual gene (e.g., J Region axis of visualization 602 of FIG. 6) in the pair of genes, and a second axis (e.g., V Region axis of visualization 602 of FIG. 6) of the second two-dimensional visualization represents a second individual gene in the pair of genes. Each cell (of the two-dimensional visualization) that intersects the first and second axis indicates a number of contigs of the one or more chain types designated by the second filter (320) in the dataset that includes the respective gene on the first axis and the respective gene on the second axis.

Scale 604 provides a basis for interpreting the x-y cells in the chart 602. In some embodiments, the heat map is color coded between a first color that indicates a first number of contigs (e.g., green, representing zero contigs) and a second number of contigs (e.g., blue, representing 120 contigs). Thus, when this color coding is used in the heat map 602, if the x-y cell in the chart 602 indicating the number of contigs present in the clonotype dataset 122 whose clonotype contains a TRAV-1-1 V region and a TRAJ3 J region is colored green, that means that there are no contigs in the clonotype dataset 122 that contain a TRAV-1-1 V region and a TRAJ3 J region. On the other hand, if the x-y cell in the chart 602 indicating the number of contigs present in the clonotype dataset 122 that contains a TRAV-1-1 V region and a TRAJ3 J region is colored blue, that means there are 120 contigs in the clonotype dataset 122 that contain a TRAV-1-1 V region and a TRAJ3 J region. In such embodiments, intermediate values between zero and 120 are represented by intermediate color shades between green and blue. It will be appreciated that scale 604 adjust to the values of the data being represented, with the maximum value representing the maximum possible contigs present in the dataset with a particular V region/J region pair. It will further be appreciated that different color palettes can be used in the heat map or, in fact, the heat map can be grey scaled. As such, referring to FIG. 6, some embodiments of the present disclosure provide a second two-dimensional visualization (602) in the form of a heat map. The heat map provides a scale (604) that provides a numeric indication in a color coded format of the number of contigs of the one or more chain types designated by the second filter (320) in the dataset that includes the respective gene on the first axis and the respective gene on the second axis for each cell in the plurality of cells of the second two-dimensional visualization.

Turning to column 320 of FIG. 3, the summary information provided in FIGS. 3 through 6 indicate how may barcodes 130 are represented by each clonotype in the clonotype dataset. Each box 306 represents a different clonotype 124, which roughly map to the cells that have the clonotype in the clonotype dataset. In some embodiments, there are doublets, meaning that a single GEM included two cells and thus the same barcode 130 for the GEM is associated with two different cells. Doublets may also be caused by multiple chains per clonotype. In the case of T cells, doublets may also cause multiple α chains or β chains per clonotype. In the case of B cells, doublets may also cause multiple heavy chains or light chains per clonotype. In the case of both B cells and T cells, doublets may be biological in origin, from allelic inclusion of both alleles of a given chain (for example, multiple light chains arising from two productive recombinants of the light chain within a given single cell). Such doublets disturb the 1 to 1 correspondence between barcodes and cell count. In some embodiments, the incidence of such doublets in the clonotype data set 122 (doublet rate) is less than 3%. In some embodiments, the incidence of such doublets in the clonotype data set 122 (doublet rate) is less than 2%. In some embodiments, the incidence of such doublets in the clonotype data set 122 (doublet rate) is less than 1%. In some embodiments, the incidence of such doublets in the clonotype data set 122 (doublet rate) is less than 0.5%. In some embodiments, the incidence of such doublets in the clonotype data set 122 (doublet rate) is less than 0.05%.

The number of possible clonotypes in a given clonotype dataset 122 can be quite large. Accordingly, referring to FIG. 7, filters 326 and 328 can be used to filter list 304. Moreover, scroll bar 308 can be used to traverse list 304. For instance, filter 326 permits one to filter by gene name (e.g., individual V or J gene name), specific CDR3 nucleotide sequence, barcode 130, contig identifier 128, or specific CDR3 amino acid sequence.

Figure 7:
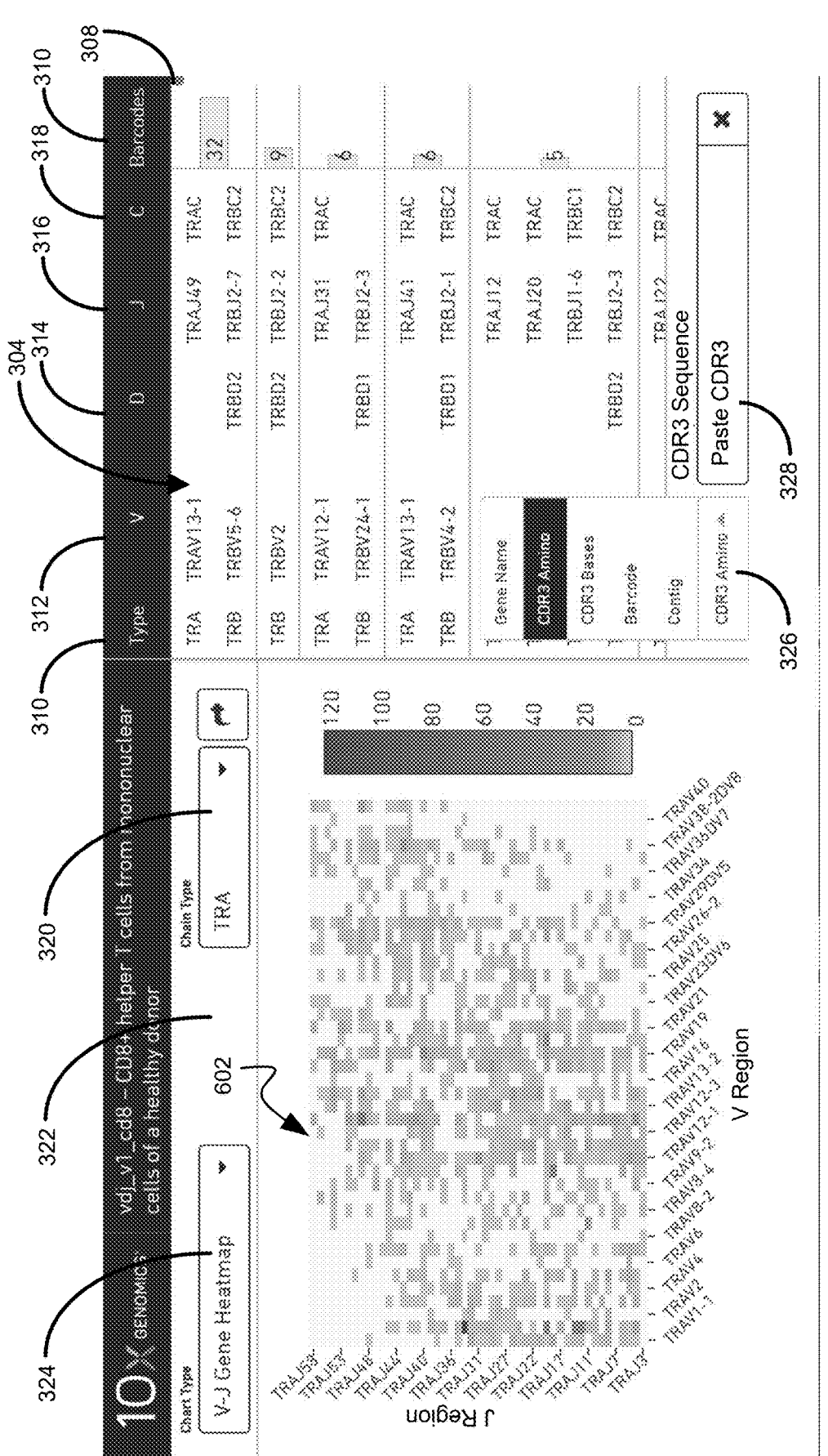
FIG. 7 illustrates an example display for entering search criteria for filtering a dataset in accordance with some embodiments.

FIG. 7 further illustrates how affordance 320 has been set so that heat map 602 now illustrates the matched V/J genes in the CDR3 region of a particular lymphocyte chain type (e.g., T cell receptor α chains). Filters 326 operate on any of the graph types of the present disclosure, such as those illustrated in FIGS. 3 through 7.

In FIG. 7, filter 326 has been set to "CDR3 Amino." In this instance, filter 328 is dynamically adjusted to accept an amino acid sequence. The contigs that contain a consensus sequence 126 having an amino acid sequence that matches the amino acid sequence query of filter 328 are provided in the list 304. The amino acid sequence specified in filter 328 can be short (e.g., less than five amino acids) which will result in more hits than when the amino acid sequence specified in filter 328 is long. Moreover, wild cards (meaning any amino acid or no amino acid whatsoever at a given position) can be specified within the sequence in the search query of filter 328. As such, some embodiments of the present disclosure provide one or more affordances 326/328 on the display that are configured to receive a user specified selection criterion. Responsive to receiving the user specified selection criterion, the listing 304 is limited to those clonotypes in the plurality of clonotypes of the dataset that match the selection criterion. As illustrated in FIG. 7, in some embodiment the selection criterion is a contig, a barcode, an amino acid sequence, or a nucleic acid sequence. Further responsive to receiving the user specified selection criterion, the two-dimensional visualization is also limited to consideration of only those clonotypes in the plurality of clonotypes that match the selection criterion.

Figure 8:
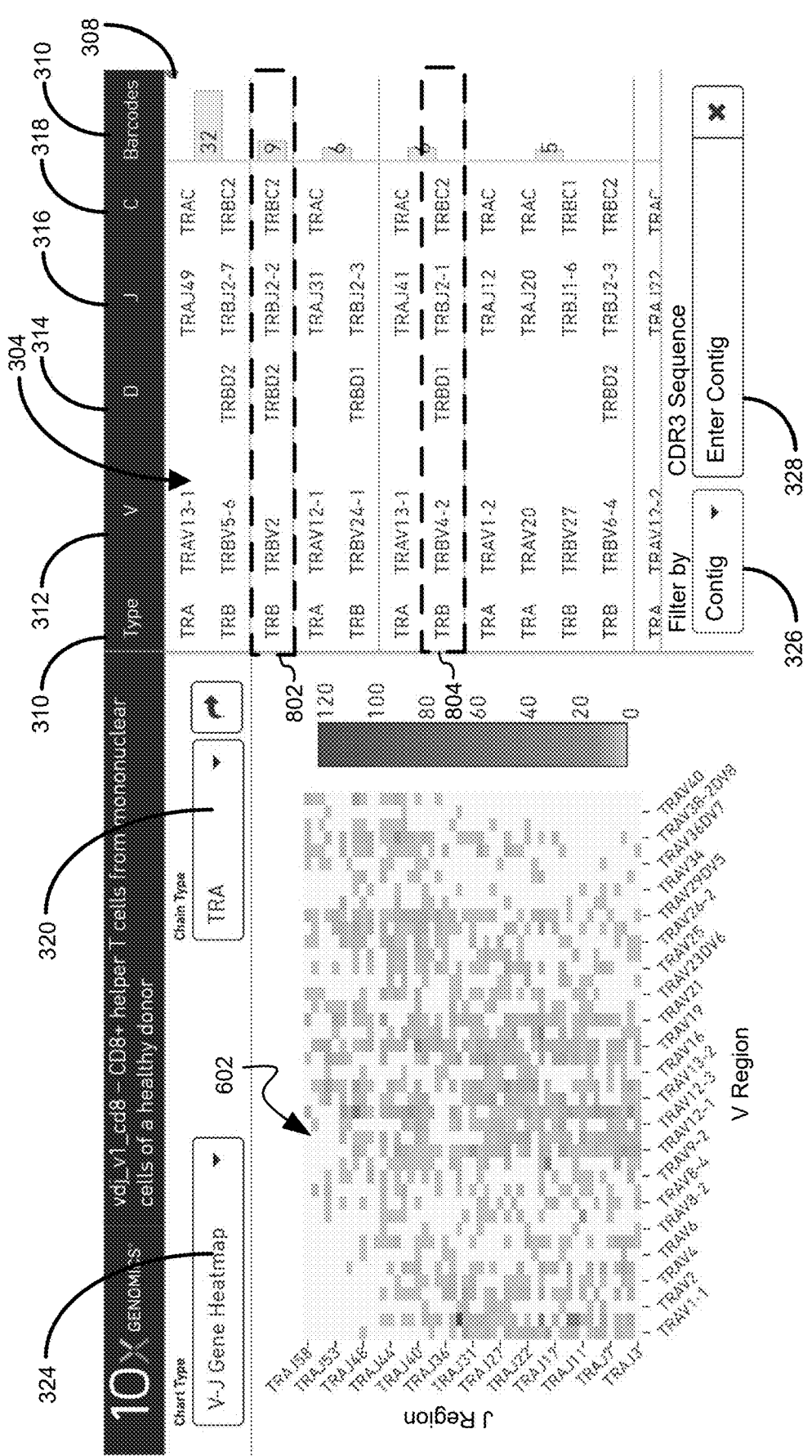
FIG. 8 illustrates an example display for entering search criteria for filtering a dataset in accordance with some embodiments.

Turning to FIG. 8, filter 326 has been set to "contig." In this instance, filter 328 is dynamically adjusted to accept one or more contig identifiers 128. When one contig identifier is entered at filter 328, the contig that matches this contig identifier is provided in the list 304. When multiple contig identifiers are entered at filter 328, any contigs that match one of the entered multiple contig identifiers is provided in the list 304

Accordingly, FIGS. 2 through 8 illustrate how the browser module 120 provides an efficient mechanism for analyzing clonotype data, for instance by providing the chain consensus sequences for any of chains in any of the clonotypes present in a clonotype dataset. In some embodiments, the browser module advantageously provides a visual verification on one side of the display of the browser as well as tabulated information on the other side of the display of the browser. Moreover, the browser module allows users to perform classic immunological tasks more efficiently, such (i) as plotting out the frequencies of clonotypes in a given clonotype dataset 122, (ii) observing the VDJ region for the most abundant clonotype in a given clonotype dataset 122 and determining how abundant the clonotype is in another dataset, (iii) obtaining an overall assessment of the clonotype data, and (iv) deriving a sense of confidence that the clonotypes that were computed for the clonotype dataset 122 (e.g., by upstream applications) are rooted in the actual regions that were sequenced. The graphics, as illustrated in FIGS. 2 through 8 provide this information to a user in a quick efficient manner in a way that cannot be done as easily or efficiently, or reliably if it were done without a computer.

Figure 30:
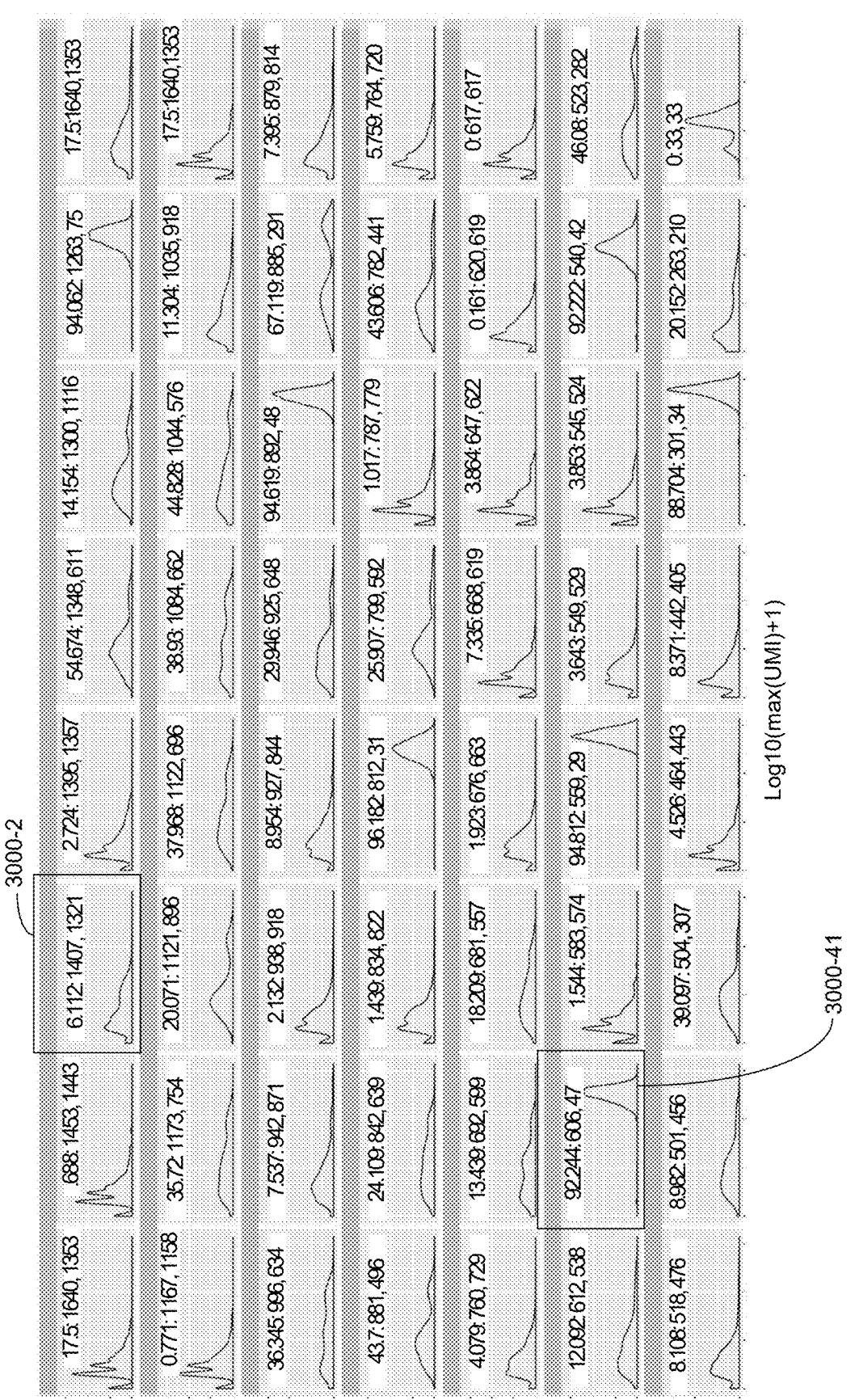
FIG. 30 illustrates a distribution of cells in each cluster in a plurality of clusters that were obtained upon clustering the population of cells of FIG. 26 based on the number and types of markers presented by such cells, where each distribution is a corresponding count (x-axis) of cells $\log_{10}$ (max (UMI)+ 1) (x-axis) and y-axis is density in accordance with an embodiment of the present disclosure and the markers considered for the clustering were a panel of 50 dextramers as well as 20 canonical immune cell markers (CD3, CD4, CD8, CD19, CD20, CD45RA, CD45RO, CD14, CD16, CD25, CD56, CD69, CD80, CD86, CD38, HLA-DR, CCR7, PD-1, SELL, and CD49).

Blocks 3646-3650. Referring to block 3646 of FIG. 36C, in some embodiments, a total number of immune cell receptor clonotypes detected within the different subset of the population of cells represented by the respective cluster is obtained. This is illustrated in FIG. 30, which illustrates a distribution of cells in each cluster in a plurality of clusters that were obtained upon clustering the population of cells of FIG. 26 based on the number and types of markers presented by such cells, where each distribution presented in FIG. 30 is a corresponding count (x-axis) of cells $\log_{10}$ (max (UMI)+1) (x-axis) and y-axis is density in accordance with an embodiment of the present disclosure. For example, distribution 3000-2 shows that the total number clonotypes for this cluster is 1407.

Figure 36C:
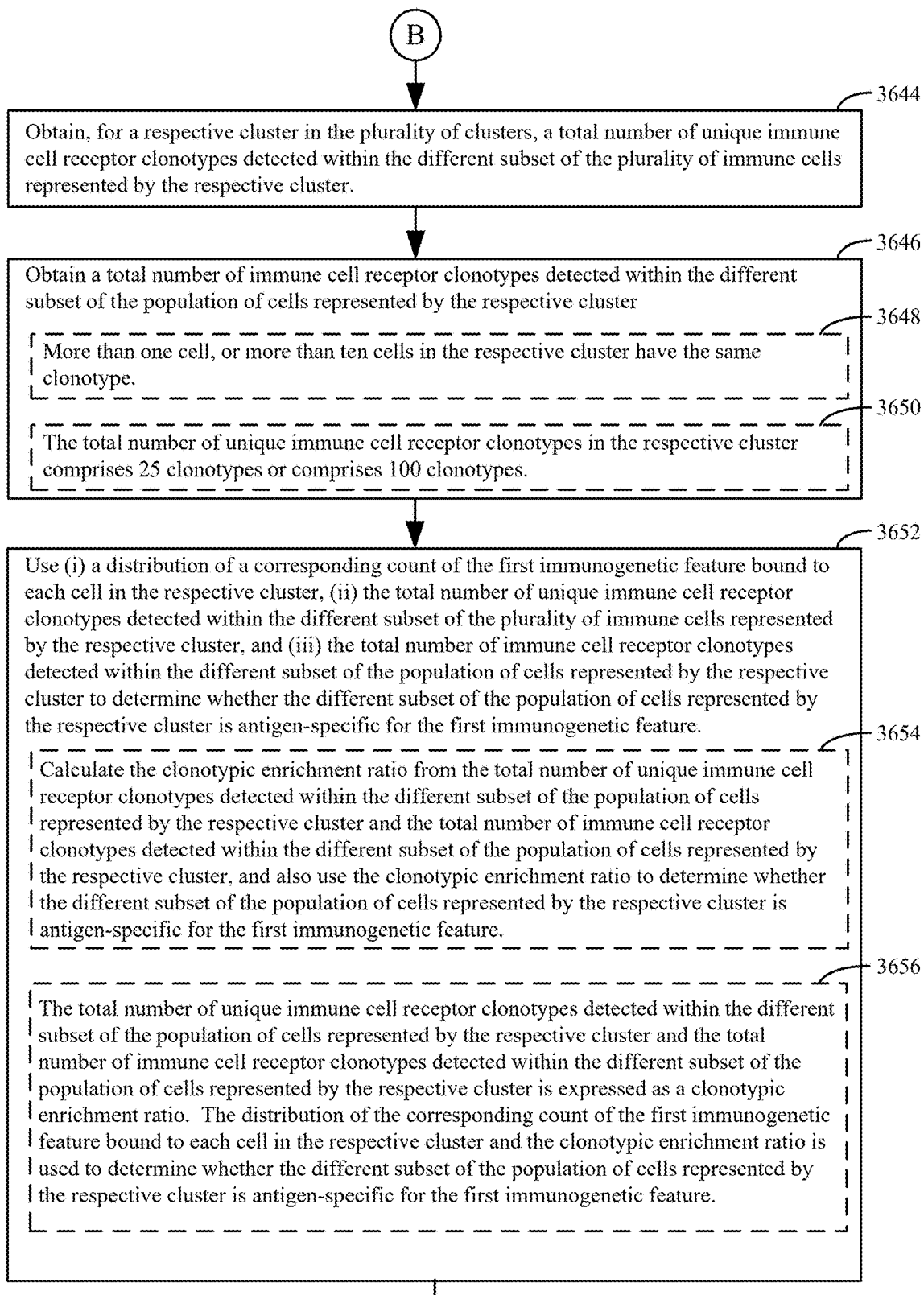

Referring to block 3648 of FIG. 36C, in some embodiments more than one cell, more than two cells, more than ten cells, or more than one hundred cells in any given cluster have the same clonotype. For example, distribution 3000-2 of FIG. 30 shows that while the total number clonotypes for this cluster is 1407, only 1321 of them are unique. Referring to block 3650 of FIG. 36C, in some embodiments the total number of unique immune cell receptor clonotypes in any given cluster comprises 25 clonotypes, comprises 100 clonotypes, comprises 150 clonotypes, comprise 300 clonotypes, comprises 500 clonotypes, comprises 800 clonotypes, or comprises 1000 clonotypes.

Block 3652. Referring to block 3652 of FIG. 36C, the method continues by using a combination of (i) a distribution of a corresponding count of the first immunogenic feature bound to or presented by each cell in the respective cluster, (ii) the total number of unique immune cell receptor clonotypes detected within the different subset of the plurality of immune cells represented by the respective cluster, and (iii) the total number of immune cell receptor clonotypes detected within the different subset of the population of cells represented by the respective cluster to determine whether the different subset of the population of cells represented by the respective cluster is antigen-specific for the first immunogenic feature.

Block 3654. Referring to block 3654 of FIG. 36C, in some embodiments the clonotypic enrichment ratio is calculated from the total number of unique immune cell receptor clonotypes detected within the different subset of the population of cells represented by the respective cluster and the total number of immune cell receptor clonotypes detected within the different subset of the population of cells represented by the respective cluster, and this clonotypic enrichment ratio is also used to determine whether the different subset of the population of cells represented by the respective cluster is antigen-specific for the first immunogenic feature.

In some embodiments, the clonotypic enrichment ratio is calculated as the (the total number of clonotypes–the num-ber of unique clonotypes)/(the total number of clonotypes) *100. For instance, in the case of distribution 3000-2 of FIG. 30, the clonotypic enrichment ratio in such embodiments is (1407–1321)/(1407)*100=6.112.

In some alternative embodiments, the clonotypic enrichment ratio is calculated as the (the total number of clonotypes–the number of unique clonotypes)/(the total number of clonotypes)*100. For instance, in the case of distribution 3000-2 of FIG. 30, the clonotypic enrichment ratio in such embodiments is (1407–1321)/(1321)*100=6.510.

Block 3656. Referring to block 3656 of FIG. 36C, in some embodiments the total number of unique immune cell receptor clonotypes detected within the different subset of the population of cells represented by the respective cluster and the total number of immune cell receptor clonotypes detected within the different subset of the population of cells represented by the respective cluster is expressed as a clonotypic enrichment ratio. Further in such embodiments, the distribution of the corresponding count of the first immunogenic feature bound to or presented by each cell in the respective cluster and the clonotypic enrichment ratio is also used to determine whether the different subset of the population of cells represented by the respective cluster is antigen-specific for the first immunogenic feature.

Figure 18:
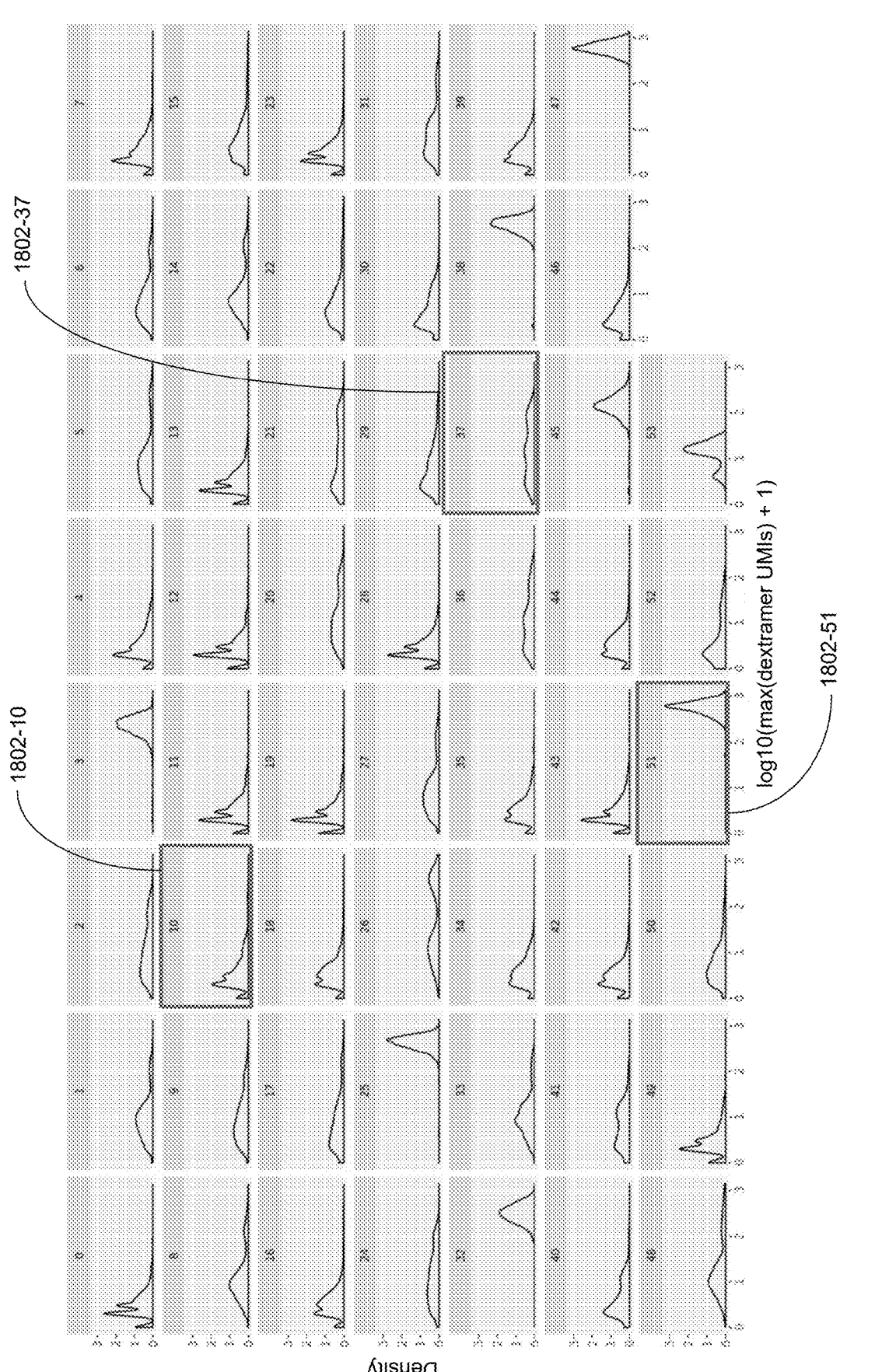
FIG. 18 illustrates a distribution of cells in each cluster in a plurality of clusters that were obtained upon clustering a population of cells based on the number and types of markers presented by such cells, where each distribution is a corresponding count (y-axis) of cells having a given count of dextramer $\log_{10}$ (max (dextramer UMIs)+1) (x-axis) bound to or presented by each cell in the respective cluster in accordance with an embodiment of the present disclosure.

Block 3658. Referring to block 3658 of FIG. 36D, in some embodiments the distribution of the corresponding count of the first immunogenic feature bound to or presented by each respective cell in the respective cluster is a trans-formed or untransformed count (e.g., density) of the first immunogenic feature bound to or presented by the respective cell. For instance, FIG. 18 illustrates a distribution of cells (e.g., distributions 1802-10, 1802-37, and 1802-51) in each cluster in a plurality of clusters that were obtained upon clustering a population of cells based on the number and types of markers presented by such cells, where each distribution is a corresponding density (y-axis) of cells having a given count of dextramer $\log_{10}$ (max (dextramer UMIs)+1) (x-axis) bound to each cell in the respective cluster in accordance with an embodiment of the present disclosure.

In some embodiments, the distribution is a kernel density estimate, histogram, or similar frequency distribution of a corresponding count of the first immunogenic feature bound to or presented by each cell in the respective cluster.

In some embodiments, the distribution is a kernel density estimate, histogram, or similar frequency distribution of a) the transformed (e.g., $\log_{10}$, $\log_2$, square root) maximum of the antigen-specific feature barcode count matrix or b) the transformed or untransformed count distribution of the count matrix for each feature barcode. This is akin to visualizing the distribution of (a) the largest feature barcode detected within a cluster, for each cell, or (b) the same distribution but for a single antigen, or for pairwise comparison of many antigens.

In the case of the histogram, one axis (e.g., the horizontal axis) is divided into sub-intervals or bins which cover the range of observed values for the corresponding count of a first immunogenic feature bound to or presented by each cell in the respective cluster (e.g., dextramer $\log_{10}$ (max (dextramer UMIs)+1)). In some embodiments, between five and 10,000, between five and 1000, or more than 20 such bins are defined. In the case where the observed values are dextramer $\log_{10}$ (max (dextramer UMIs)+1), each such bin represents a sub-range of the observed values for dextramer $\log_{10}$(max (dextramer UMIs)+1). Then, each observed cell is placed into a corresponding bin based on its dextramer $\log_{10}$ (max (dextramer UMIs)+1) count. Whenever a cell falls inside an interval (e.g., based on its dextramer count in this example), a box of defined height is added to the interval. If more than one cell has a dextramer $\log_{10}$ (max (dextramer UMIs)+1) falling inside the same bin, the boxes of defined height stack for each such cell are stacked on top of each other. In this way, a histogram of the distribution of the corresponding count of the first immunogenic feature bound to or presented by each respective cell is drawn.

Figure 40:
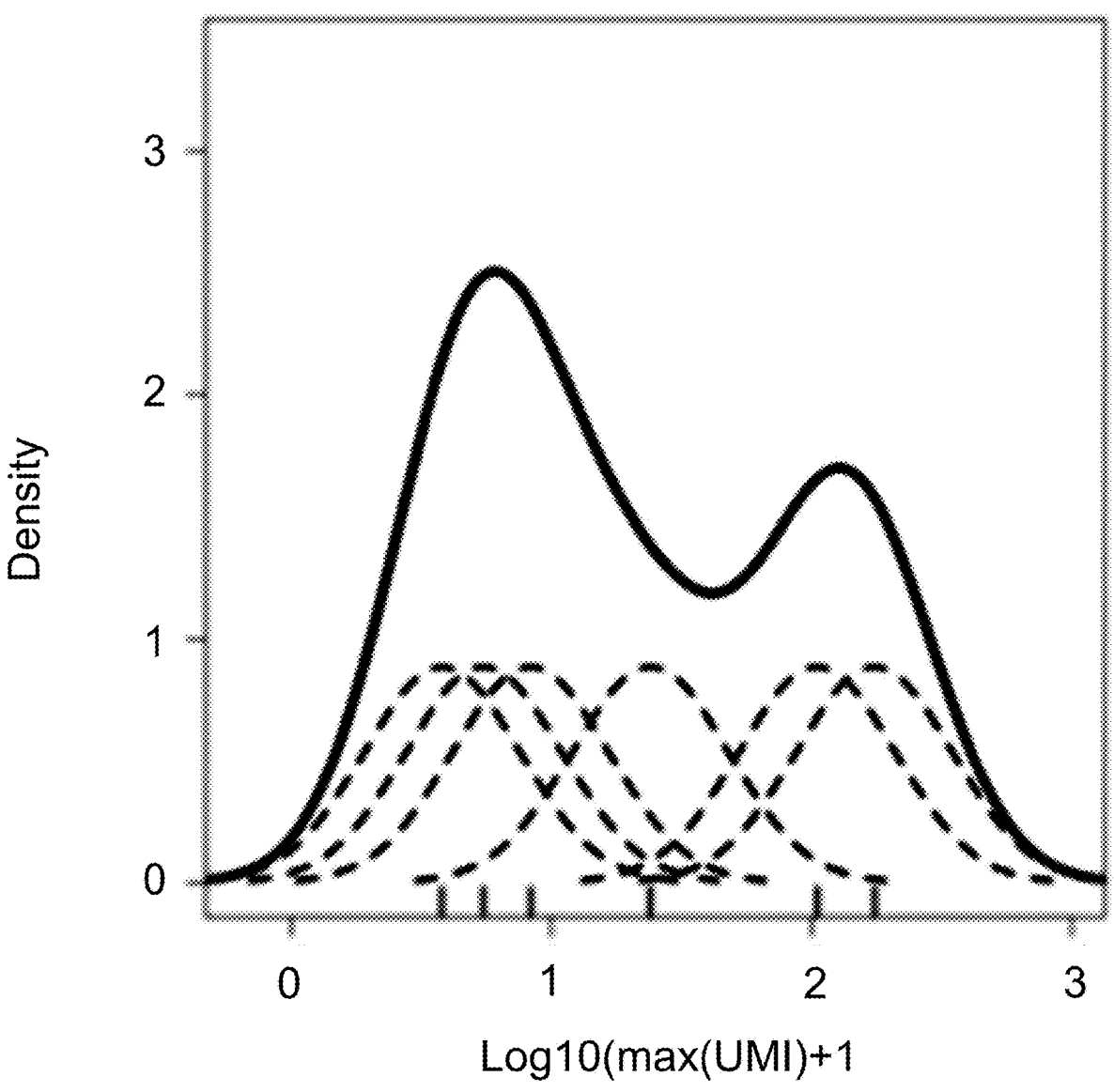
FIG. 40 illustrates a distribution of a corresponding count of the first immunogenic feature bound to or presented by each cell in the respective cluster in the form of a kernel density estimate.

With reference to FIG. 40, in the case where the distribution of a corresponding count of the first immunogenic feature bound to or presented by each cell in the respective cluster is a kernel density estimate, each respective cell in a given cluster of cells is positioned on an axis (x-axis of FIG. 40) as a datapoint $x_i$ based on its corresponding count of the first immunogenic feature bound to or presented by the respective cell. A normal kernel with a given standard deviation is placed on each of the data points $X_i$. Such kernels are represented in FIG. 40 by dashed lines. The kernels are summed to make the kernel density estimate (solid curve in FIG. 40). Kernel density estimates are further described in Hastie et al., 2001, *The Elements of Statistical Learning: Data Mining, Inference, and Prediction*, Springer Verlag, New York, pp. 182-184, which is hereby incorporated by reference.

Block 3660. Referring to block 3660 of FIG. 36D, in some embodiments the distribution of the corresponding count of the first immunogenic feature bound to or presented by each respective cell in the respective cluster is a transformed count of the first immunogenic feature bound to or presented by the respective cell, where the transformation is $\log_{10}$, $\log_2$, or square root. This is illustrated by the distribution illustrated in FIG. 40, where the transformation is $\log_{10}$ on the x-axis.

Block 3662. Referring to block 3660 of FIG. 36D, in some embodiments the at least 1,000 immune cells are B cells. Further, the population of cells also comprises non-immune cells. In such embodiments, the distribution is a pairwise distribution of the first immunogenic feature against a second immunogenic feature and the second immunogenic feature is associated with B cells (e.g., CD19, CD20, CD79a, or PAX5).

Figure 31:
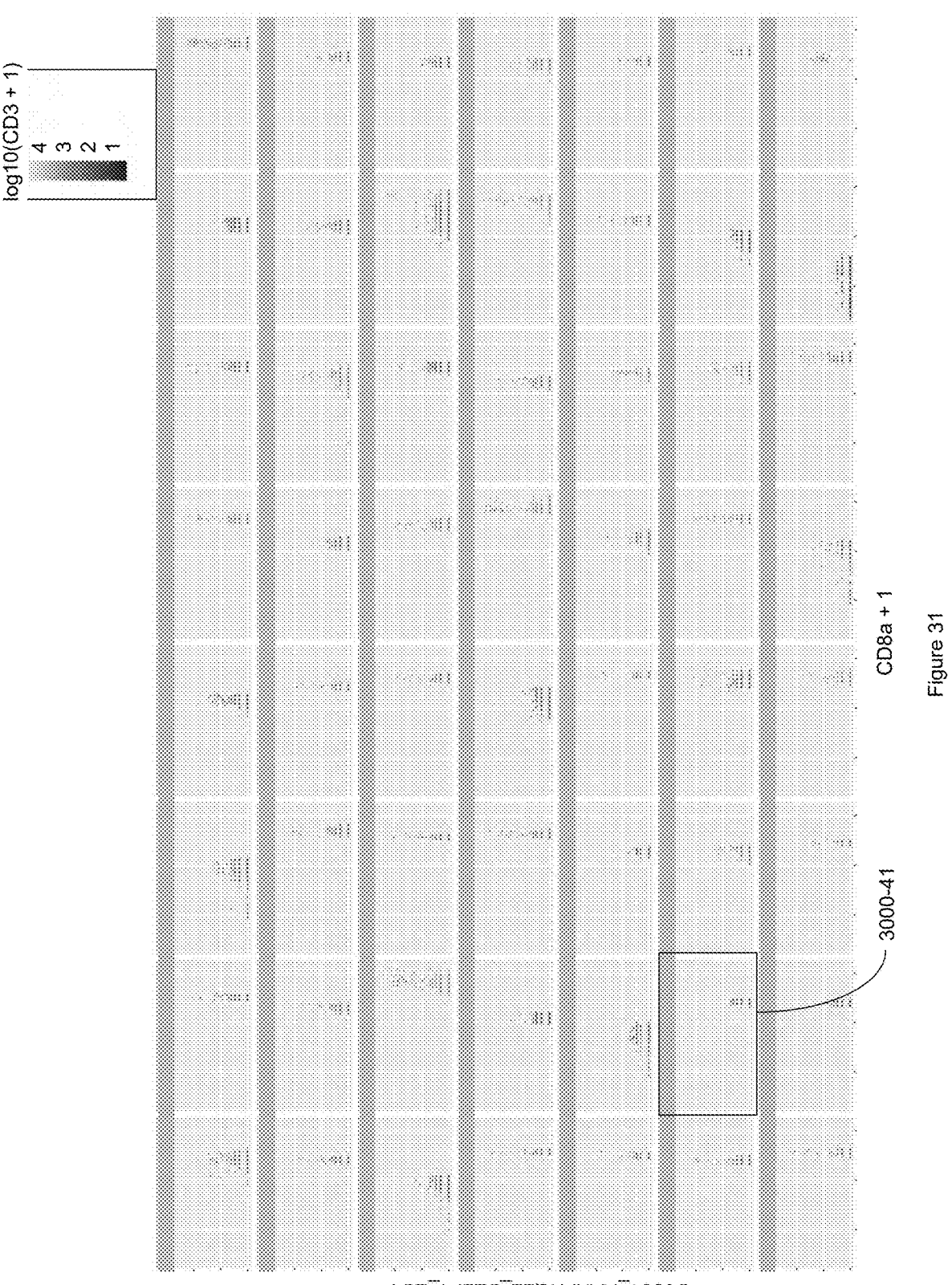
FIG. 31 illustrates a two-way density distribution of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of BOB01_RAKFKQLL_BZLF1 EBV antigen bound by an individual cell, and each point in the Figure is a different cell in the population of cells that is colored by its $\log_{10}$ (CD3+1) count, where CD3 is the number of CD3 markers presented by a respective cell.

Block 3664. Referring to block 3662 of FIG. 36D, in some embodiments the at least 1,000 immune cells are T cells. Further, the population of cells also comprises non-immune cells. In such embodiments, the distribution is a pairwise distribution of the first immunogenic feature against a second immunogenic feature and the second immunogenic feature is associated with B cells (e.g., MHC tetramer, peptide-MHC tetramer, MHC dextramer, a peptide-MHC dextramer, CD3, or CD8a). FIG. 31 illustrates a pairwise distribution (two-way density distribution) of a first immunogenic feature against a second immunogenic feature of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of B0B01_RAKFKQLL_BZLF1 EBV antigen bound by an individual cell, and each point in the Figure is a count of cells in the population of cells that is colored by its $\log_{10}$ (CD3+1) count, where CD3 is the number of CD3 markers presented by a respective cell.

Blocks 3666-3668. Referring to block 3666 of FIG. 36D, in some embodiments, the corresponding count of the respective immunogenic feature bound to or presented by each immune cell in the population of cells is acquired through single-cell sequencing in which the first immunogenic feature is assigned a unique barcode. Such barcodes may be attached to each immunogenic feature bound to immune cells as discussed above in conjunction with block 3602.

Referring to block 3668 of FIG. 36D, upon determining that respective cluster includes a mixture of cells that that are antigen-specific for the first immunogenic feature and cells that are not antigen-specific for the first immunogenic feature, the distribution of the corresponding count of the first immunogenic feature bound to or presented by each cell in the respective cluster is used to remove from the respective cluster those cells that are not antigen-specific for the first immunogenic feature. This is illustrated by the distribution of cluster 1802-37 in FIG. 18, which is illustrated in greater detail in FIG. 21. FIG. 22 illustrates a two-way density distribution of the cells in cluster 1802-37 of FIG. 18 in which the x-axis represents the number of instances of the IVTDFSVIK/EBV antigen bound by an individual cell, the y-axis is a count of the number of instances of the AVFDRKSDAK/EBV antigen bound by an individual cell, and each point in the two-way density distribution is a different cell in cluster 1802-37 that is colored by A*0301 KLG/CMV count, as well as the clonotypes of cells in specific regions of the distribution that indicate that cluster 37 contains EBV-specific T cells, in accordance with an embodiment of the present disclosure. The clonotypes observed for region 2102 of the two-way density distribution indicated that these cells contain EBV-specific T cells, whereas the clonotypes observed for region 2104 of the two-way density distribution contain influenza-specific T cells. Thus the barcodes of the cells in regions 2102 and 2104 of the two-way density distribution can be used to remove the noisy cells in region 2104 from cluster 1802-37 to enrich for the cells in region 2102 (e.g., to enrich for the EBV-specific T cells.

Blocks 3670-3674. Referring to block 3670 of FIG. 36D, in some embodiments, the first immunogenic feature is an epitope associated with cancer, and the at least 1,000 immune cells are cytotoxic T-lymphocytes. In some embodiments, and referring to block 3672 of FIG. 36D, a subject afflicted with cancer is exposed to the different subset of the plurality of immune cells represented by the respective cluster. In alternative embodiments, and referring to block 3674 of FIG. 36, a subject afflicted with cancer is exposed to cells cloned from the different subset of the plurality of immune cells represented by the respective cluster.

Exemplary structure of a clonotype dataset. In some embodiments clonotype dataset 122 is organized as a series of data blocks with a master JSON table of contents at the beginning of the file and a JSON table of contents describing the addresses and structure of each block at the end of the file.

In some embodiments there are a plurality of blocks in the clonotype dataset 122.

In some embodiments, one such block constitutes a database (e.g., a sqlite3 database) containing one table each for clonotypes, lymphocyte (e.g. T cells, B cells) receptor chain reference sequences, lymphocyte (e.g. T cells, B cells) receptor chain consensus sequences 126, contigs 128, and a secondary table mapping cell barcodes 130 to clonotypes 124. This database is queried to create the clonotype list, sorted by frequency, and again queried to populate the chain visualization with data when clicking on the chain in the user interface disclosed herein. Each row in the reference, consensus and contig tables also include file offsets and lengths that encode the location of more detailed and hierarchical information about that entity within a set of JSON files, stored within other blocks in the plurality of block. Finally, alignment and sequence information for each reference and consensus are stored in the database for future debugging and troubleshooting.

In some embodiments, one or more blocks contain a reference annotation JSON file, which is a complete set of information about each reference per lymphocyte (e.g. T cell, B cell) receptor chain. This block is equivalent to VDJ chain reference sequence table 140. Accordingly, in some embodiments, VDJ chain reference sequence table 140 is a component of the clonotype dataset 122.

In some embodiments, one or more blocks contain a consensus annotation, e.g., as JSON file, which is a complete set of information about each consensus sequence 126 per lymphocyte (e.g. T cell, B cell) receptor chain.

In some embodiments, one or more blocks contains a contig annotation, e.g. as a JSON file, which is a complete set of information about each contig 128. A contig 128 is the assembled sequence of a transcript that encodes α chain (e.g. T cell α chain, T cell β chain, B cell heavy chain, B cell light chain) of a lymphocyte receptor (e.g., T cell receptor, B cell immunoglobulin). Thus, in the example case of a single T cell it is expected that there would be at least one contig 128 for the α chain and at least one contig 128 for the β chain.

In some embodiments, one or more blocks contain a reference sequence, e.g., in FASTA format, that is used during clonotype dataset 122 file creation, not during VDJ browser 120 operation, for debugging purposes.

In some embodiments, one or more blocks contain a reference alignment, e.g. as a BAM file, which stores how chain consensus sequence/contigs 128 differ from the reference sequence. This is typically used during clonotype dataset 122 creation as opposed to during VDJ browser 120 operation, for instance, for debugging purposes. In some embodiments, one or more blocks contain a reference alignment BAM index for the above identified BAM file to accelerates sequence alignment queries.

In some embodiments, one or more blocks contain a consensus sequence, e.g., in FASTA format, that is typically used during clonotype dataset 122 creation as opposed to during browser module 120 operation.

In some embodiments, one or more blocks contain consensus alignments BAM file that stores how contig sequences differ from the consensus, which are typically used during clonotype dataset 122 creation as opposed to during browser module 120 operation.

In some embodiments, one or more blocks contain a contig BAM index which stores where to find read information for individual contigs.

In some embodiments, one or more blocks contain a contig BED file that stores gene annotations for each contig. In some embodiments, one or more blocks contain a contig FASTA file that stores sequences of each contig.

EXAMPLES

Example 1

Figure 9:
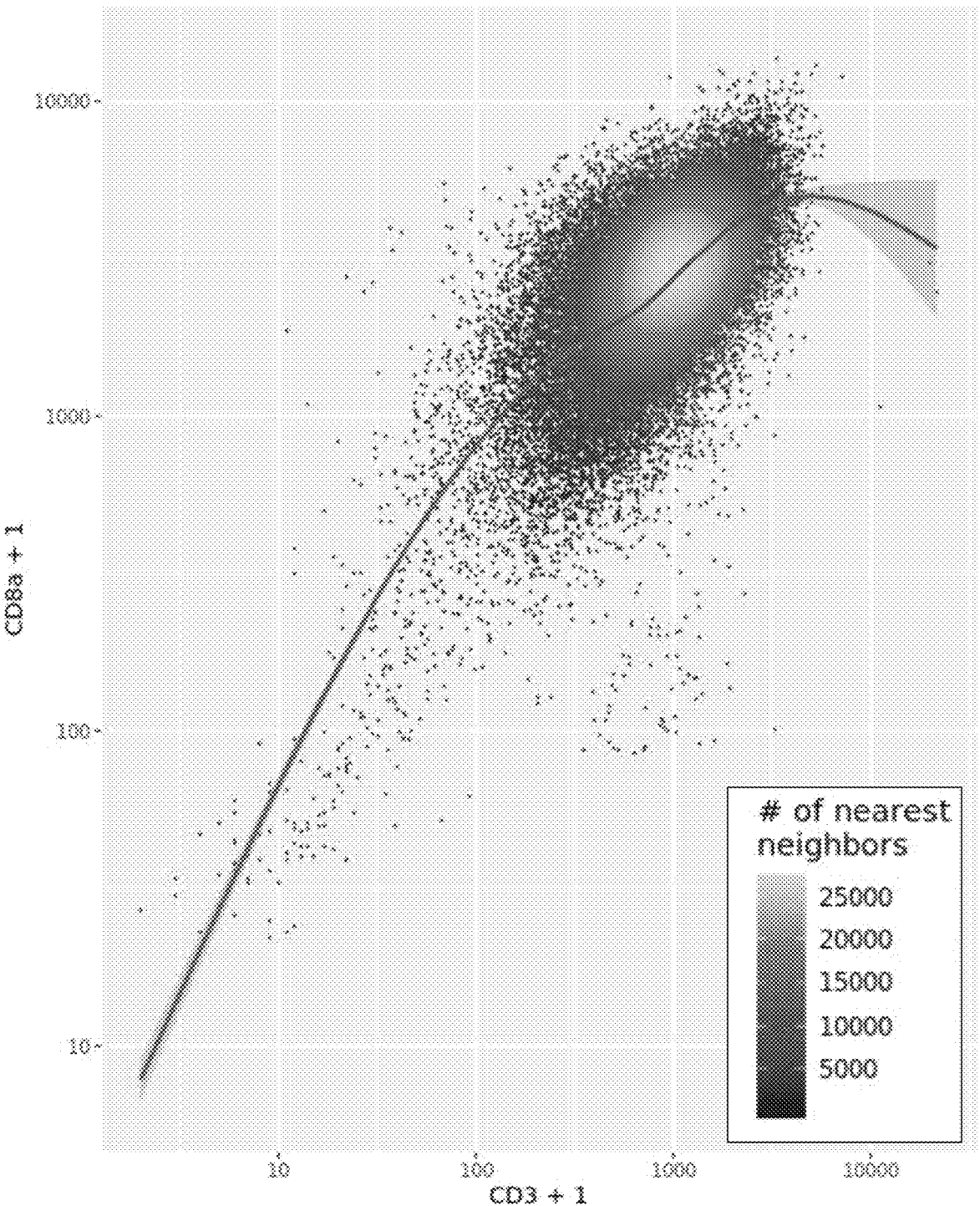
FIG. 9 illustrates a density distribution for a population of cells in which each point in the scatterplot represents a respective cell in the population of cells, the x-coordinate is a count of the CD3 marker presented by the respective cell, the y-coordinate is a count of the CD8a marker presented by the respective cell, and the color of each point indicates the number of nearest neighbors the corresponding respective cell has in the density distribution in accordance with an embodiment of the present disclosure.

FIG. 9 illustrates a two-way density distribution for 45,000 T cells, prior to any form of clustering, in which each point in the distribution represents a respective cell in the population of cells, the x-coordinate is a count of the CD3 antigen bound to the respective cell, the y-coordinate is a count of the CD8a (T cell surface glycoprotein CD8 alpha chain) marker presented by the respective cell, and the color of each point indicates the number of nearest neighbors (cells) the corresponding respective cell has in the density distribution in accordance with an embodiment of the present disclosure. The CD3 antigen is a surface structure associated with the T cell receptor (TCR) to form a complex involved in antigen recognition and signal transduction. CD8A is an integral membrane glycoprotein that plays an important role in the immune response and serves multiple functions in responses against both external and internal offenses. In T cells, CD8A functions primarily as a coreceptor for MHC class I molecule: peptide complex. As such, it is to be expected that CD3 and CD8a would be associated with the same cells. The two-way density distribution of FIG. 9 confirms this is the case with a large cluster of cells in the region of the distribution that indicates cells having both CD3 and CD8a.

Figure 10:
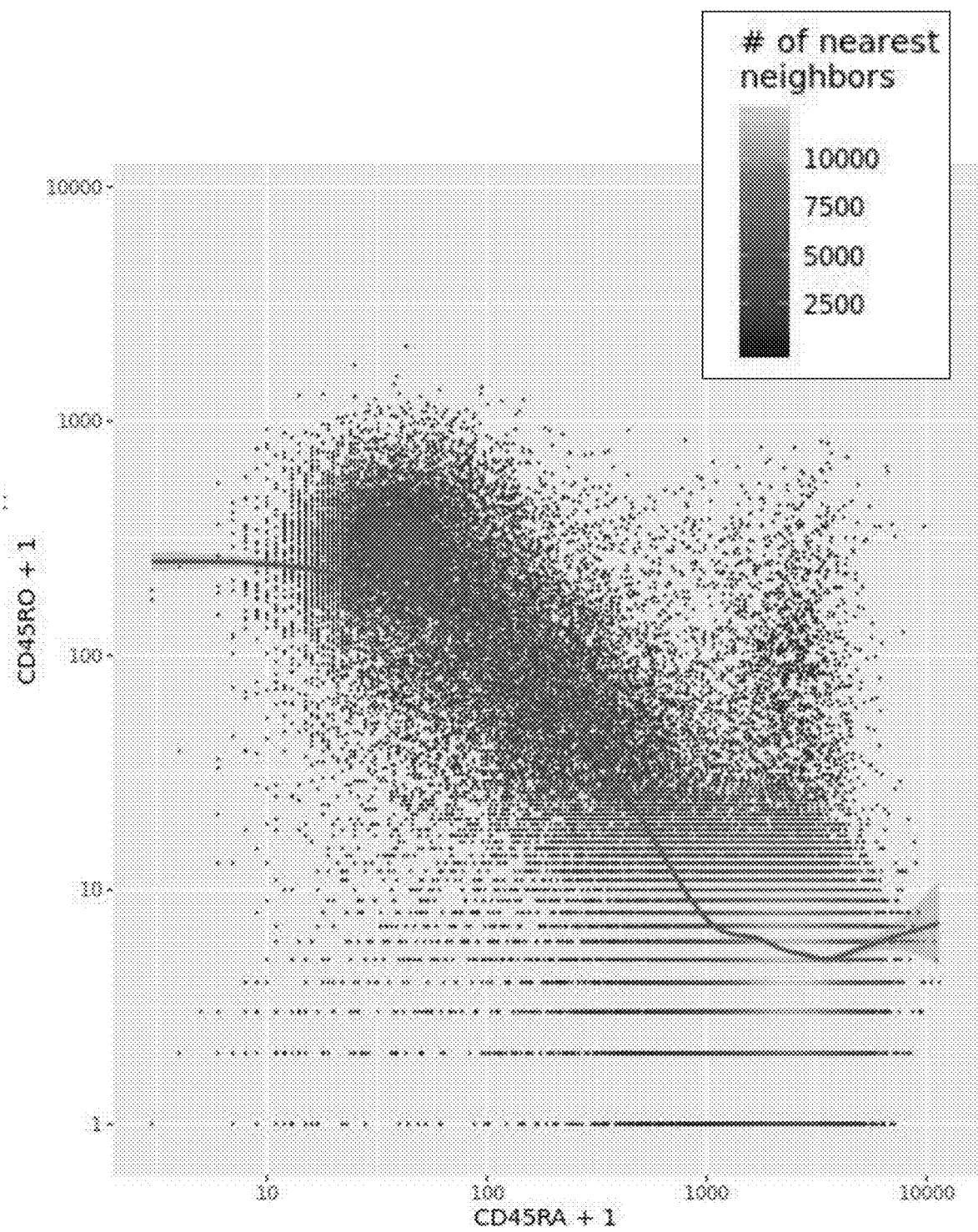
FIG. 10 illustrates a density distribution for a population of cells in which each point in the scatterplot represents a respective cell in the population of cells, the x-coordinate is a count of the CD45RA marker presented by the respective cell, the y-coordinate is a count of the CD45RO marker presented by the respective cell, and the color of each point indicates the number of nearest neighbors the corresponding respective cell has in the density distribution in accordance with an embodiment of the present disclosure.

FIG. 10 illustrates a density distribution for 45,000 T cells, prior to any form of clustering, in which each point in the distribution represents a respective cell in the population of cells, the x-coordinate is a count of the CD45RA marker presented by the respective cell, the y-coordinate is a count of the CD45RO marker presented by the respective cell, and the color of each point indicates the number of nearest neighbors the corresponding respective cell has in the density distribution in accordance with an embodiment of the present disclosure. Immune cells typically express CD45RO or CD45RA, but not both, and this phenomenon is reflected in the density distribution of FIG. 10. In FIG. 10 further shows that there are some cells that are in transition between presenting CD45RO and presenting CD45RA. Thus, FIG. 10 makes it clear that density distributions are a useful tool for exploring the biology of immune cells.

Figure 11:
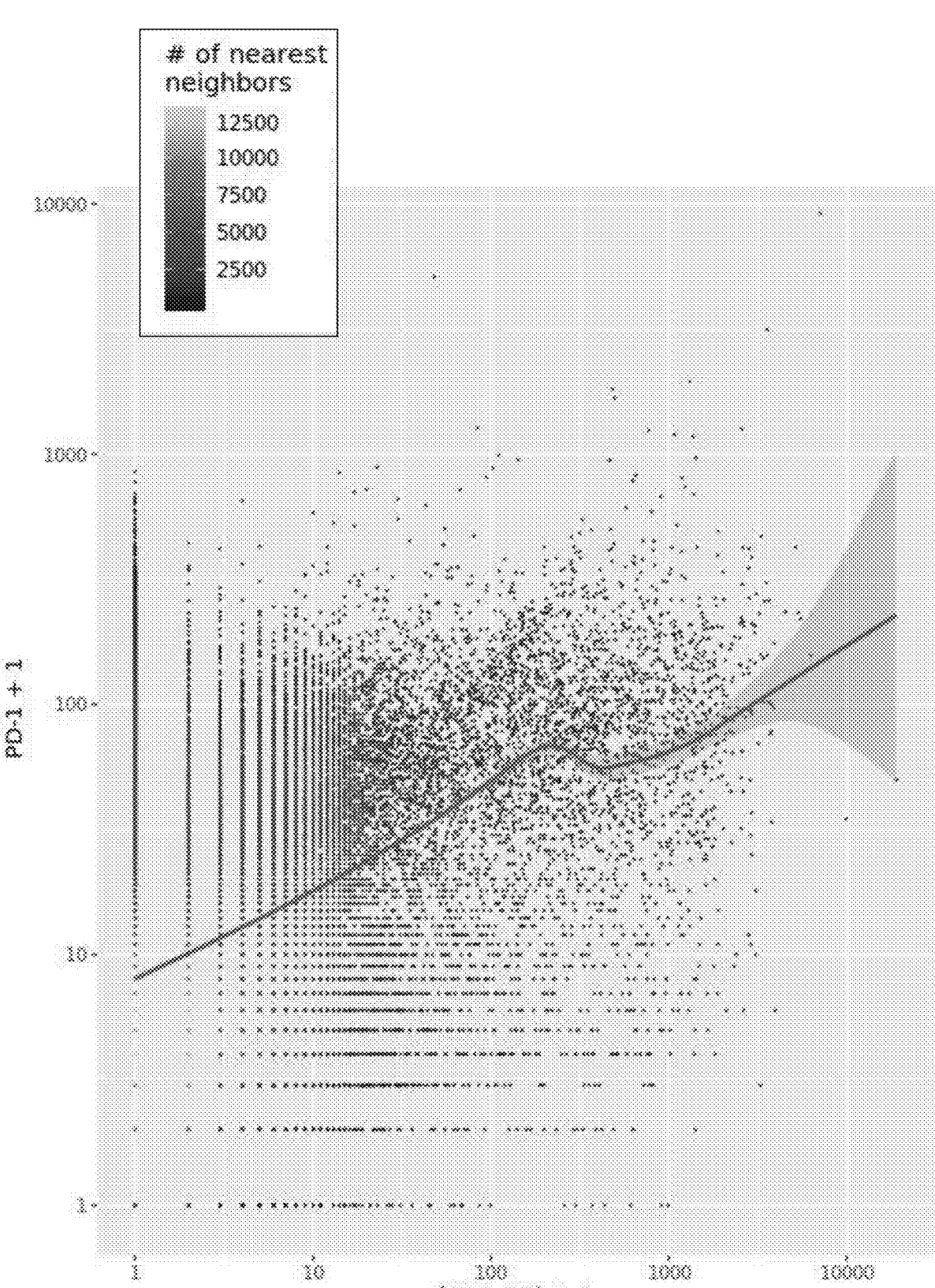
FIG. 11 illustrates a density distribution for a population of cells in which each point in the scatterplot represents a respective cell in the population of cells, the x-coordinate is a count of the HLA-DR marker presented by the respective cell, the y-coordinate is a count of the PD-1 marker presented by the respective cell, and the color of each point indicates the number of nearest neighbors the corresponding respective cell has in the density distribution in accordance with an embodiment of the present disclosure.

FIG. 11, illustrates another density distribution for 45,000 T cells, prior to any form of clustering, in which each point in the distribution represents a respective cell in the population of cells, the x-coordinate is a count of the HLA-DR marker presented by the respective cell, the y-coordinate is a count of the PD-1 protein bound to the respective cell, and the color of each point indicates the number of nearest neighbors the corresponding respective cell has in the density distribution in accordance with an embodiment of the present disclosure. The HLA-DR receptor is typically presented by macrophages, B cells, or dendritic cells, whereas the PD-1 protein is found on T cells that help keep the body's immune responses in check. When PD-1 is bound to another protein called PD-L1, it helps keep T cells from killing other cells, including cancer cells. Some anticancer drugs, called immune checkpoint inhibitors, are used to block PD-1. As such, HLA-DR and PD-1 would not be expected to be presented by the same cells, which is consistent with the density distribution of FIG. 11 which has a very low density throughout the distribution.

Figure 12:
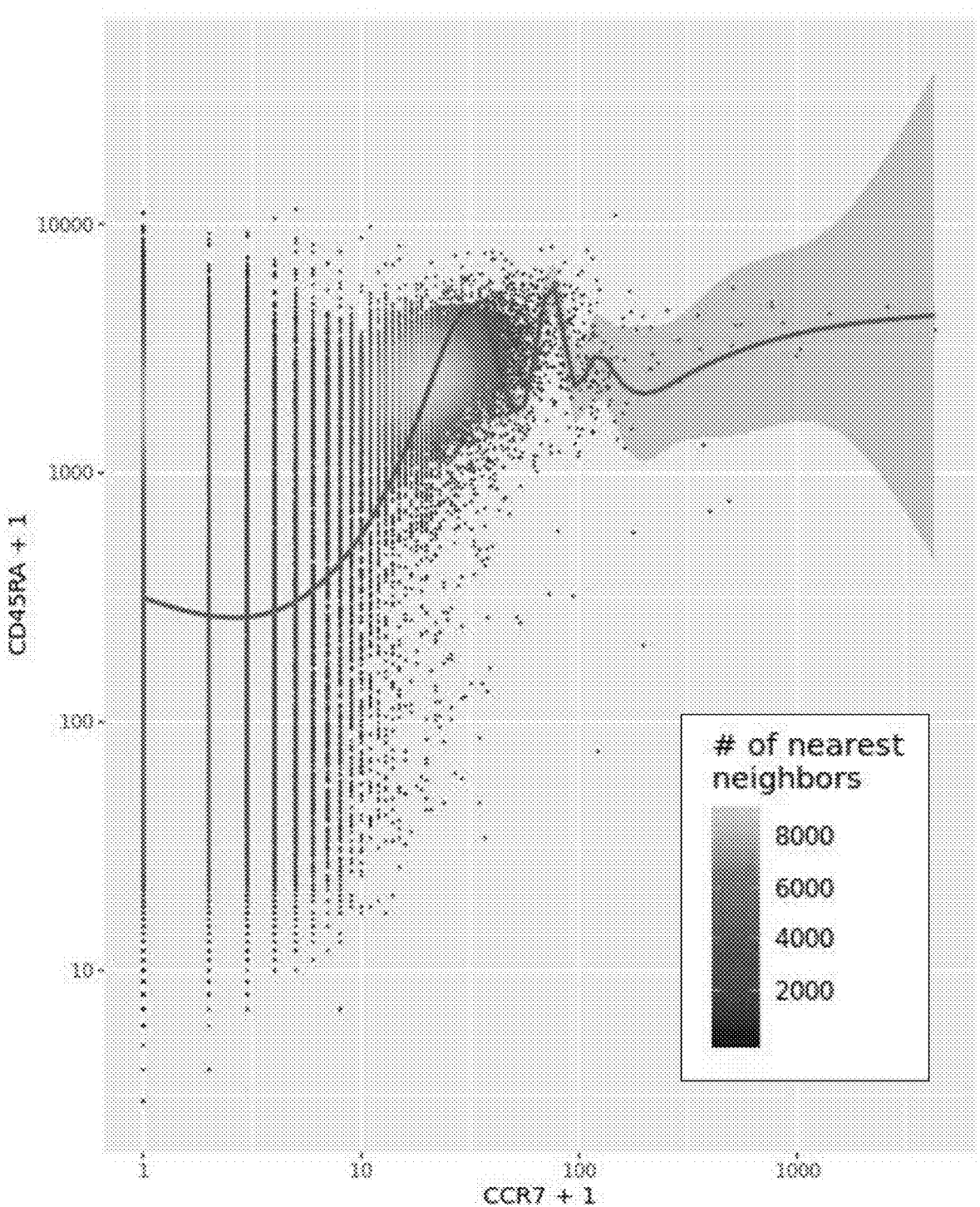
FIG. 12 illustrates a density distribution for a population of cells in which each point in the scatterplot represents a respective cell in the population of cells, the x-coordinate is a count of the CCR7 marker presented by the respective cell, the y-coordinate is a count of the CD45RA marker presented by the respective cell, and the color of each point indicates the number of nearest neighbors the corresponding respective cell has in the density distribution in accordance with an embodiment of the present disclosure.

FIG. 12 illustrates a density distribution for 45,000 T cells in which each point in the scatterplot represents a respective cell in the population of cells, the x-coordinate is a count of the CCR7 marker presented by the respective cell, the y-coordinate is a count of the CD45RA marker presented by the respective cell, and the color of each point indicates the number of nearest neighbors the corresponding respective cell has in the density distribution in accordance with an embodiment of the present disclosure. CCR7 is expressed by B cells, mature dendritic cells (DCs) and by several T cell sub-populations including naive, regulatory and central memory T cells. CD45RA, also called protein tyrosine phosphatase receptor type C, is a marker of naive T cells. As such, CCR7 and CD45RA would not be expected to be presented by the same cells, which is consistent with the density distribution of FIG. 12 which has a very low density throughout the distribution.

FIG. 13 illustrates the number of cells in each cluster in a plurality of clusters that were obtained upon clustering a population of 45,000 cells using PARC (See, Stassen et al., "PARC: ultrafast and accurate clustering of phenotypic data of millions of single cells," BioRxiv preprint doi.org/ 10.1101/765628, which is hereby incorporated by reference), based on the number and types of markers presented by such cells in accordance with an embodiment of the present disclosure. The markers used for this clustering were a panel of 50 dextramers as well as 20 canonical immune cell markers (CD3, CD4, CD8, CD19, CD20, CD45RA, CD45RO, CD14, CD16, CD25, CD56, CD69, CD80, CD86, CD38, HLA-DR, CCR7, PD-1, SELL, and CD49). Advantageously, by performing such clustering in accordance with the present disclosure it is possible to identify sub-populations of cells that are enriched for a specific type of immune cell. For instance, each cluster in FIG. 13 constitutes possible sub-population of such cells. The methods of the present disclosure provide tools for ascertaining which, if any of the clusters of FIG. 13 are enriched for a specific type of immune cell (e.g., an immune cell that specific for a particular immunogenic feature such an antigen and/or an immune cell that presents a specific immunogenic feature such as a particular cell surface protein).

Figure 14:
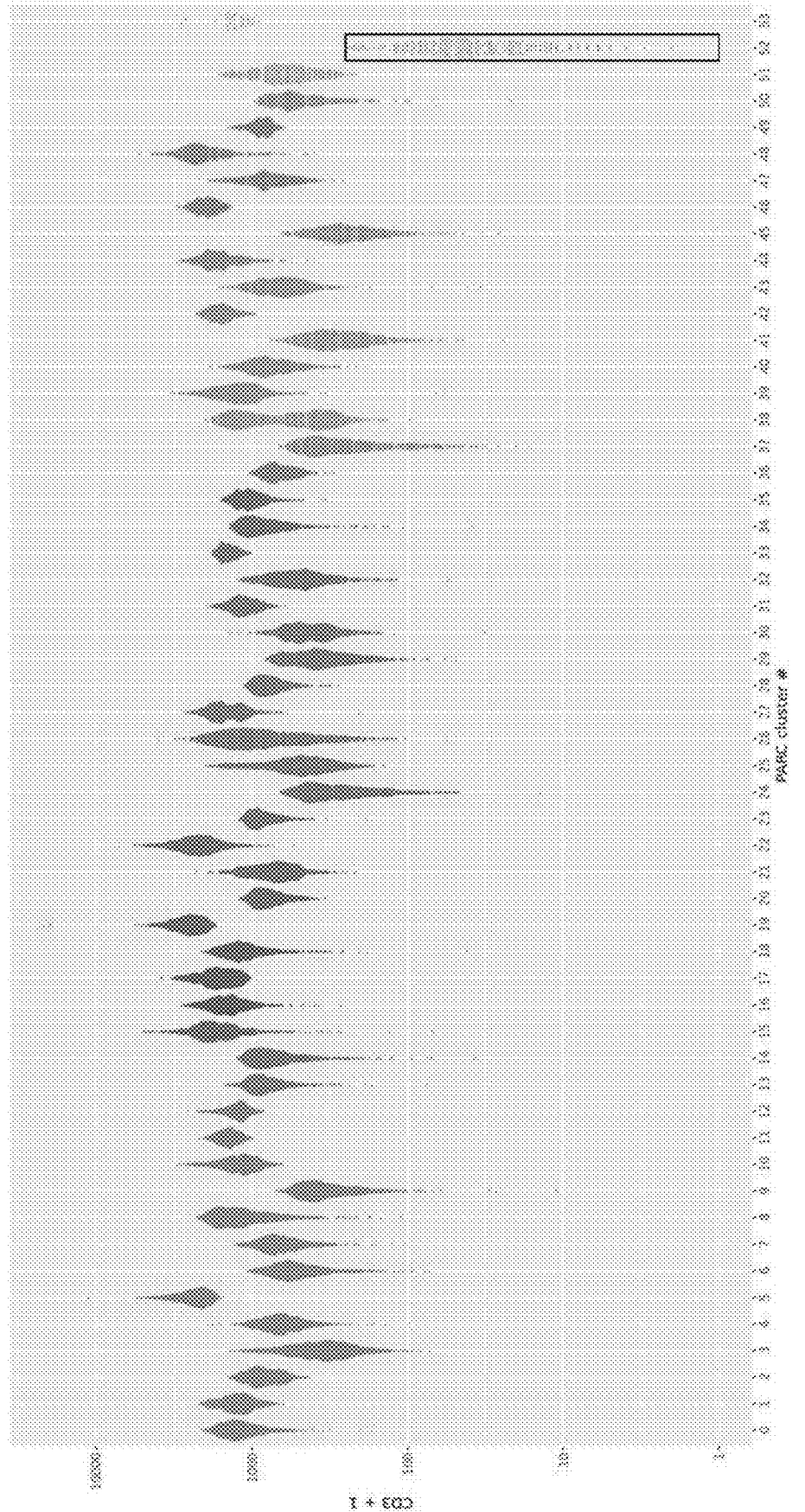
FIG. 14 illustrates a distribution of cells in each cluster in a plurality of clusters that were obtained upon clustering a population of cells based on the number and types of markers presented by such cells, in which the x-axis is a count of the number of instances of the CD3 marker presented by individual cells and each point in the Figure is a different cell in the population of cells in accordance with an embodiment of the present disclosure.

FIG. 14 illustrates a distribution of the cells in each of the cluster of FIG. 13, in which the x-axis is a count of the number of instances of the CD3 marker presented by individual cells in individual clusters and each point in the Figure is a different cell in the population of cells clustered for FIG. 13.

Figure 15:
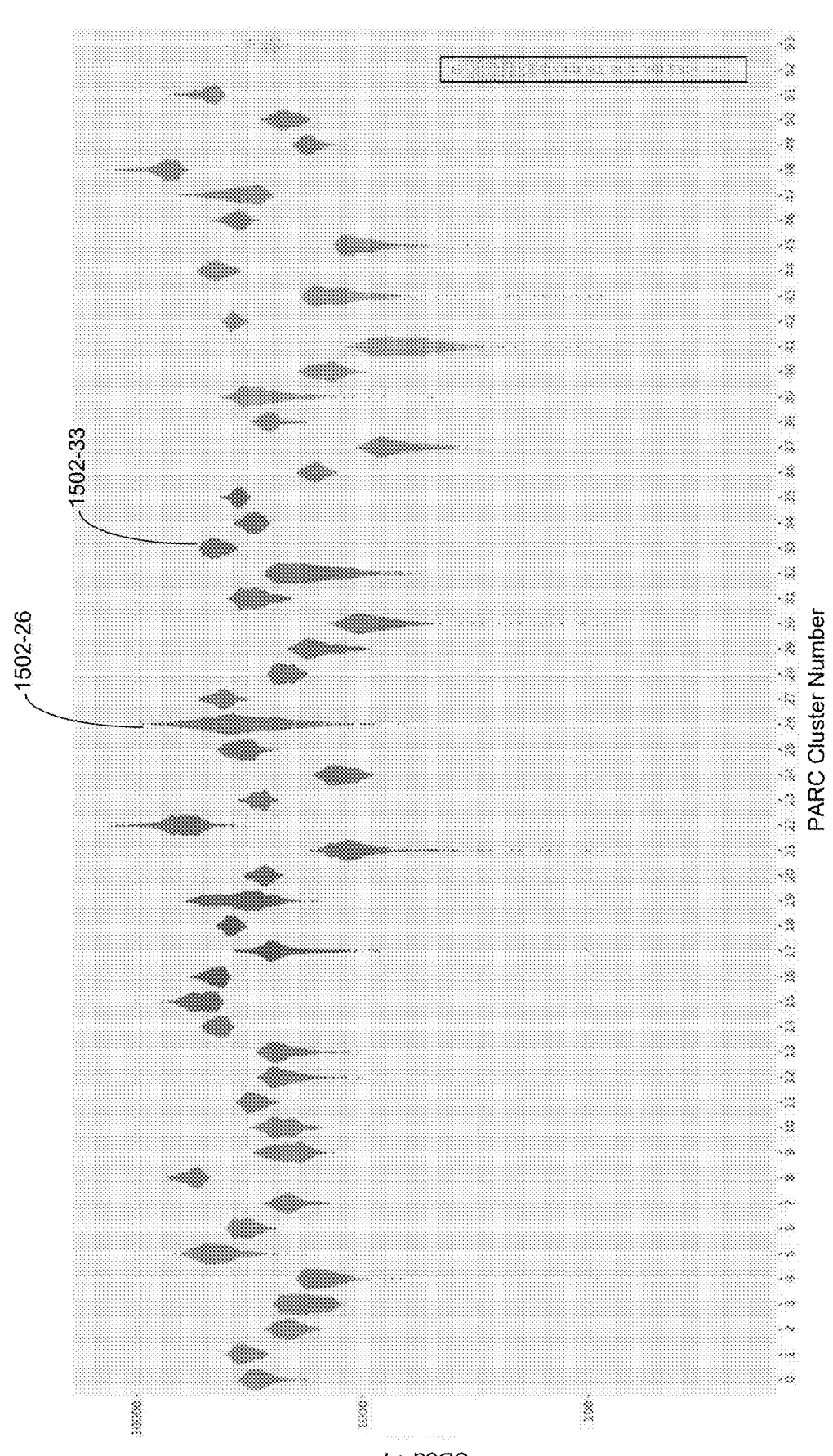
FIG. 15 illustrates a distribution of cells in each cluster in a plurality of clusters that were obtained upon clustering a population of cells based on the number and types of markers presented by such cells, in which the x-axis is a count of the number of instances of the CD8a marker presented by individual cells and each point in the Figure is a different cell in the population of cells in accordance with an embodiment of the present disclosure.

FIG. 15 illustrates a distribution of cells in each cluster in a plurality of clusters that were obtained upon clustering a population of cells based on the number and types of markers presented by such cells, in which the x-axis is a count of the number of instances of the CD8a marker (associated with T cells) presented by individual cells and each point in the Figure is a different cell in the population of cells in accordance with an embodiment of the present disclosure. The various distributions for each cluster indicate that in some clusters with long tails, such as cluster 1502-26, a very heterogeneous population of cells within the cluster whereas for cluster 1502-33, a potentially homogenous population of cells within the cluster.

Figure 16:
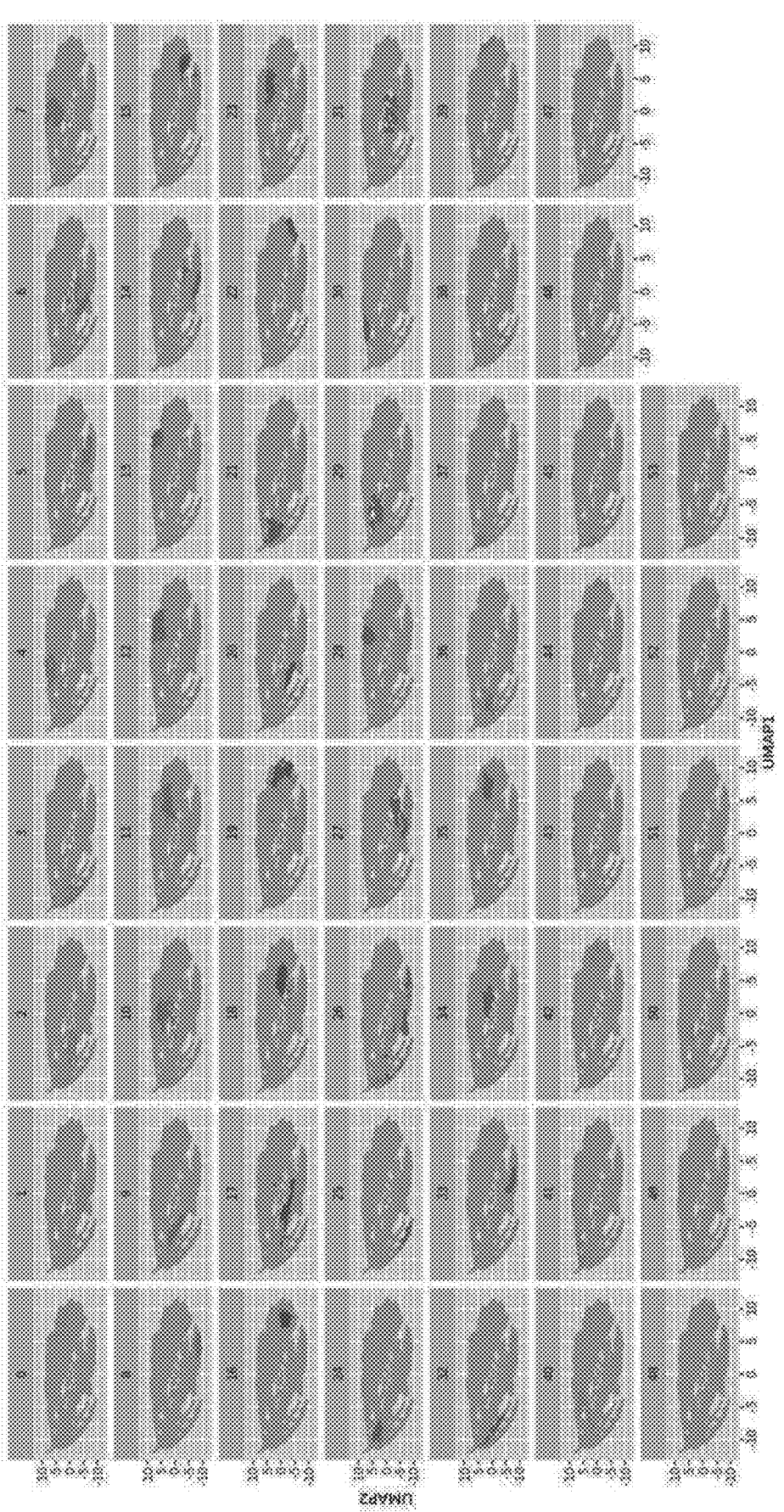
FIG. 16 illustrates a representation of a uniform manifold approximation and projection (UMAP) of a population of cells based on the number and types of markers presented by such cells and, for each respective cluster in a plurality of clusters that were obtained upon clustering the population of cells based on the number and types of markers presented by such cells, an indication of where the cells of the respective cluster lie within the UMAP in accordance with an embodiment of the present disclosure.

FIG. 16 illustrates a representation of a uniform manifold approximation and projection (UMAP) of the population of cells clustered in FIG. 13 based on the number and types of markers presented by such cells and, for each respective cluster identified in FIG. 13, an indication of where the cells of the respective cluster lie within the UMAP in accordance with an embodiment of the present disclosure. FIG. 16 illustrates that each of the clusters of cells have a unique biology as exhibited by the fact that each cluster occupies a different portion of the UMAP.

Figure 17:
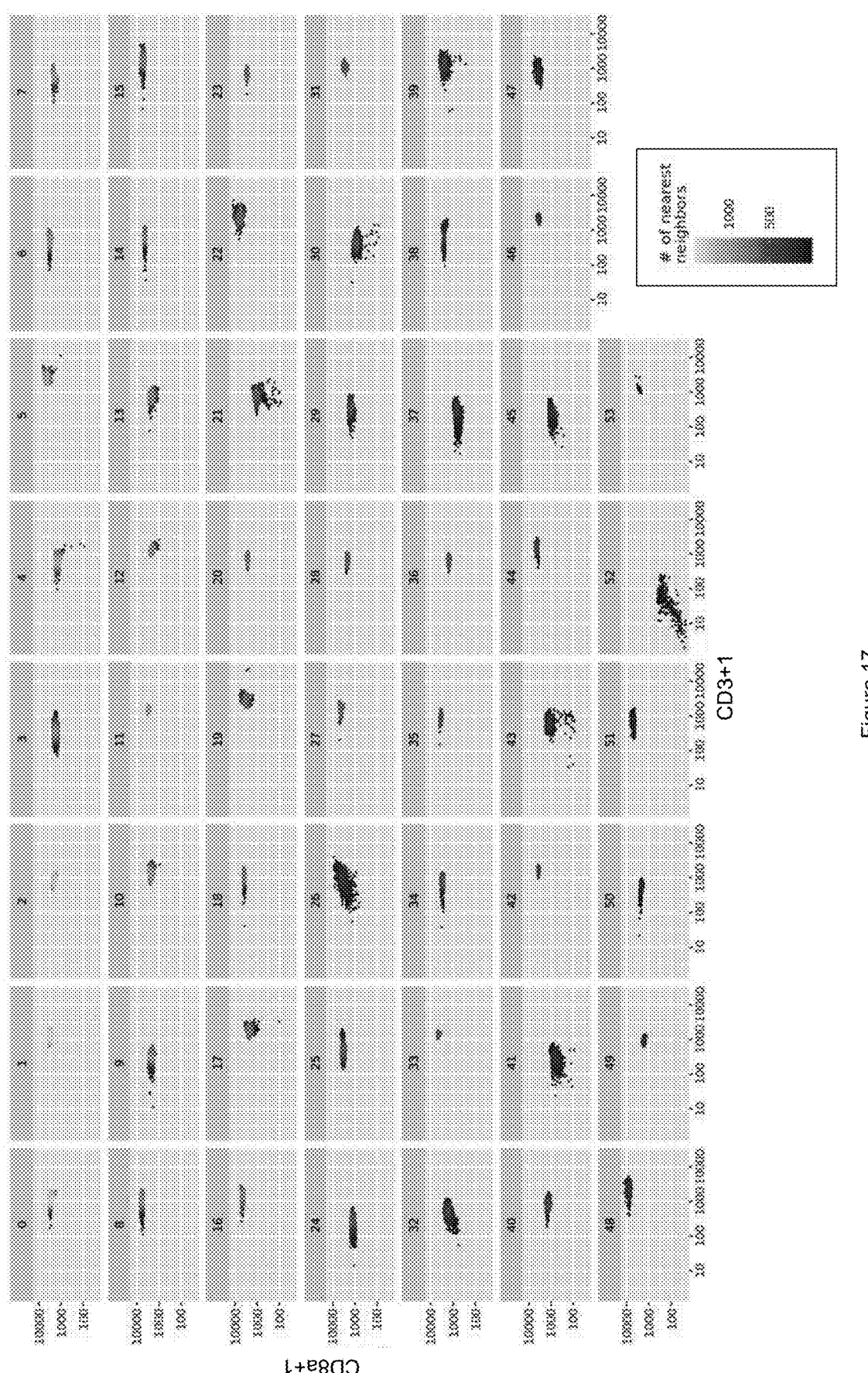
FIG. 17 illustrates a two-way density distribution of cells in each cluster in a plurality of clusters that were obtained upon clustering a population of cells based on the number and types of markers presented by such cells, in which the x-axis represents the number of instances of the CD3 marker presented by an individual cell, the y-axis is a count of the number of instances of the CD8a marker presented by an individual cell, and each point in the Figure is a different cell in the population of cells that is colored by the number of cells in the vicinity of the cell in the two-way density distribution in accordance with an embodiment of the present disclosure.

FIG. 17 illustrates a two-way density distribution of cells in each of the clusters of FIG. 13, in which the x-axis represents the number of instances of the CD3 marker presented by an individual cell, the y-axis is a count of the number of instances of the CD8a marker presented by an individual cell, and each point in the Figure is a different cell in the population of cells that is colored by the number of cells in the vicinity of the cell in the two-way density distribution in accordance with an embodiment of the present disclosure. In this regard, FIG. 17 compares directly with FIG. 9 with the exception that FIG. 9 is a distribution of an entire population of cells before PARC clustering whereas FIG. 17 is an distribution of cells in each respective cluster of the entire population of cells after PARC clustering. FIG.

17 demonstrates that, at least with respect to the T cell markers CD3 and CD8a, some clusters are more homogenous than other clusters.

FIG. 18 illustrates a distribution of cells in each of the clusters of FIG. 13. Here, the distribution is a kernel density distribution of the counts of dextramer $\log_{10}$ (max (dextramer UMIs)+1) bound to each cell (counts of antigen specific molecule bound to cells within each cluster). Dextramer reagents (Immudex, Copenhagen, DK) have been developed, consisting of a dextran polymer backbone to which multiple MHC complexes and fluorochrome molecules are covalently bound. See, Tario et al., 2015, "Dextramer Reagents are Effective Tools for Quantifying CMV Antigen-Specific T Cells from Peripheral Blood Samples," Cytometry Part B (Clinical Cytometry) 888:6-20, which is hereby incorporated by reference. Thus, a high dextramer count, here $\log_2$ (max (dextramer UMIs)+1), indicative of a population of T cells.

Various different kinds of distributions are exhibited in FIG. 18.

One example is the distribution 1802-37 for cluster 37, which is characterized as being a zero-inflated left-handed tail distribution. In statistics, a zero-inflated model is a statistical model based on a zero-inflated probability distribution, e.g. a distribution that allows for frequent zero-valued observations. As seen in distribution 1802-37, the dextramer count has very little density indicating an absence of cells that recognize and bind the dextramer antigen in cluster 1802-37.

Figure 21:
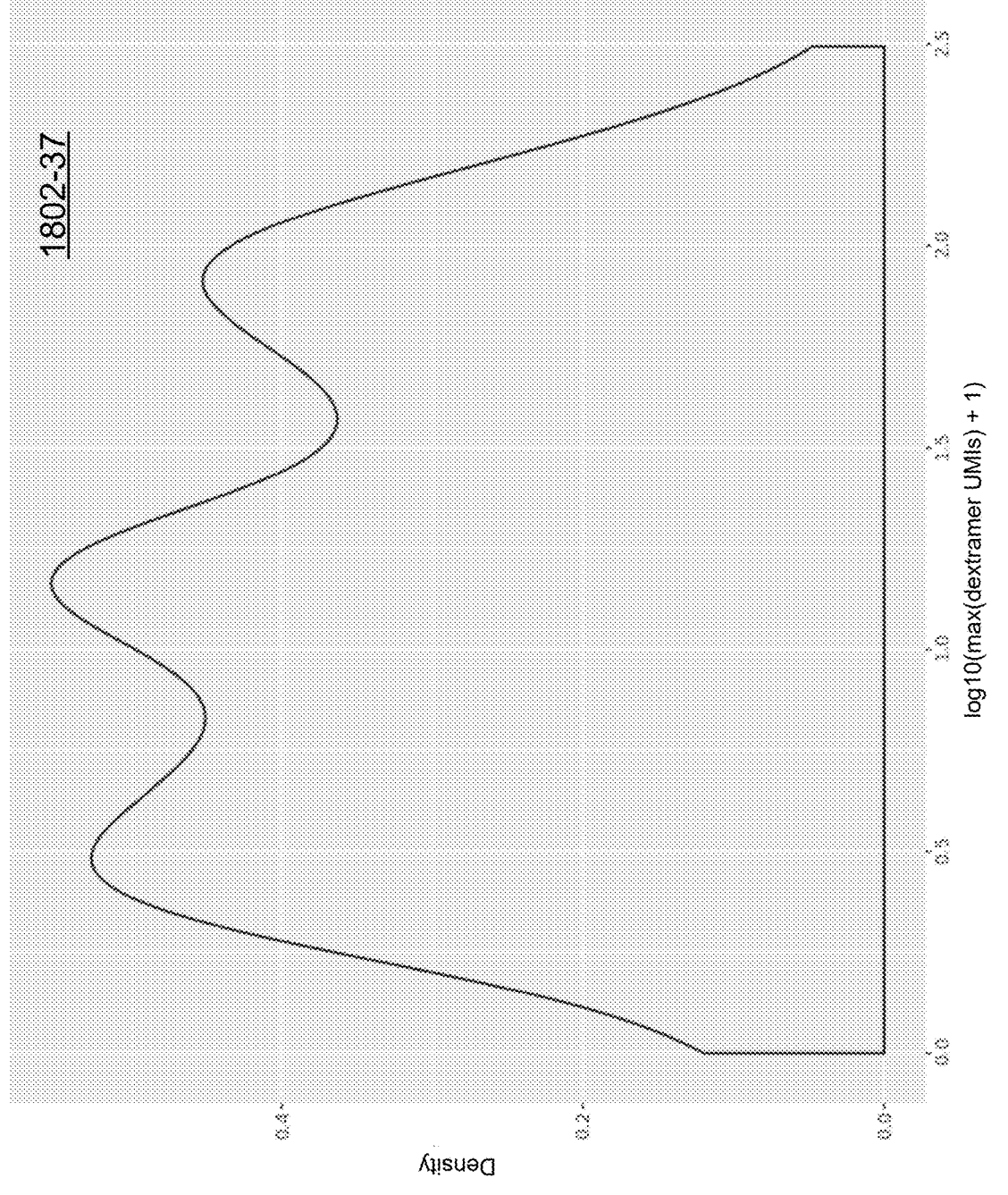
FIG. 21 illustrates the distribution of cells in cluster 37 of FIG. 18, where the distribution is a corresponding count (y-axis) of cells having a given count of dextramer $\log_{10}$ (max (dextramer UMIs)+1) (x-axis) bound to or presented by each cell in cluster 37 in accordance with an embodiment of the present disclosure.
Figure 22:
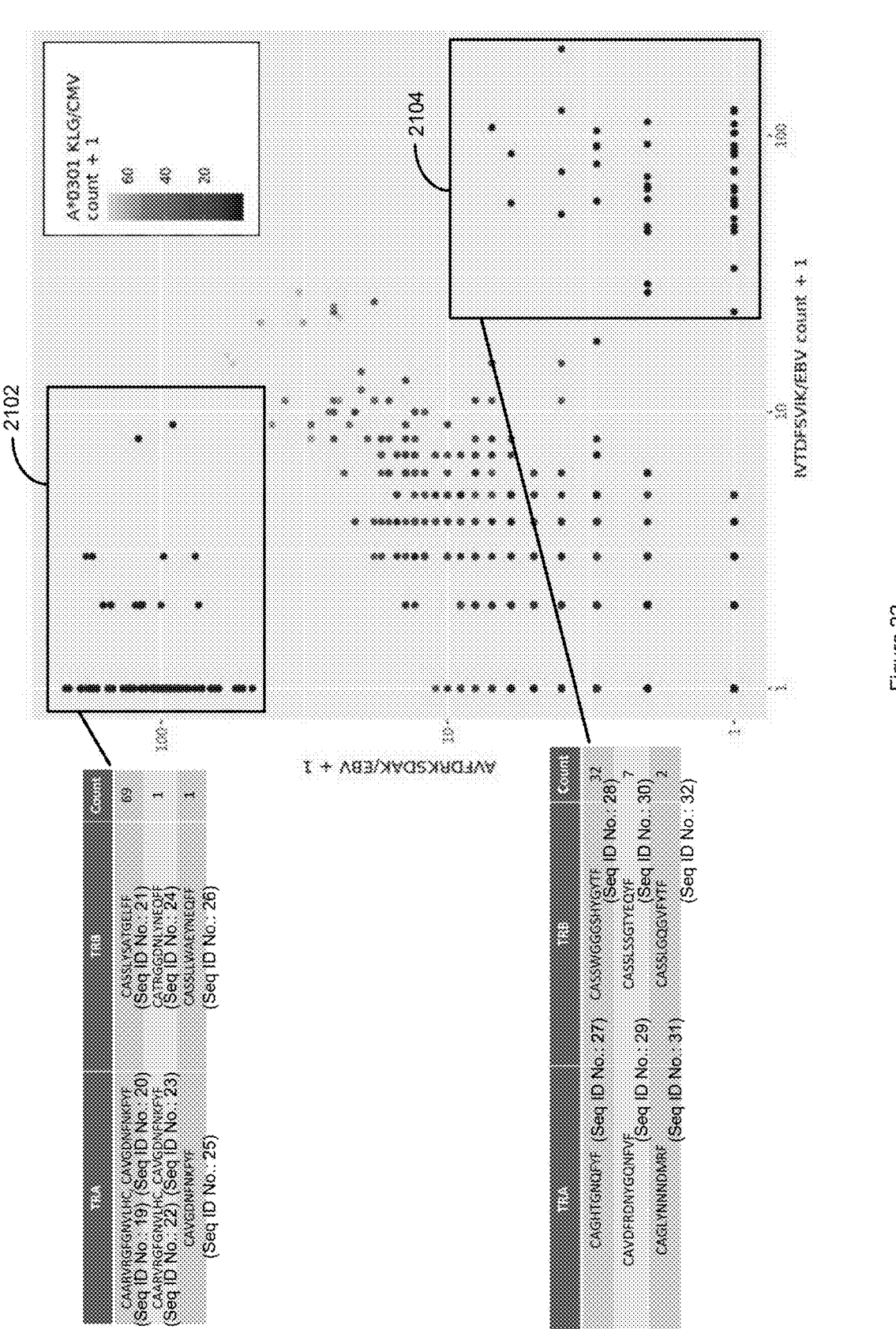
FIG. 22 illustrates a two-way density distribution of the cells in cluster 37 of FIG. 18 in which the x-axis represents the number of instances of the IVTDFSVIK/EBV antigen bound by an individual cell, the y-axis is a count of the number of instances of the AVFDRKSDAK/EBV antigen bound by an individual cell, and each point in the two-way density distribution is a different cell in cluster 37 that is colored by A*0301 KLG/CMV count, as well as the clonotypes of cells in specific regions of the distribution that indicate that cluster 37 contains EBV-specific T cells, in accordance with an embodiment of the present disclosure.
Figure 23:
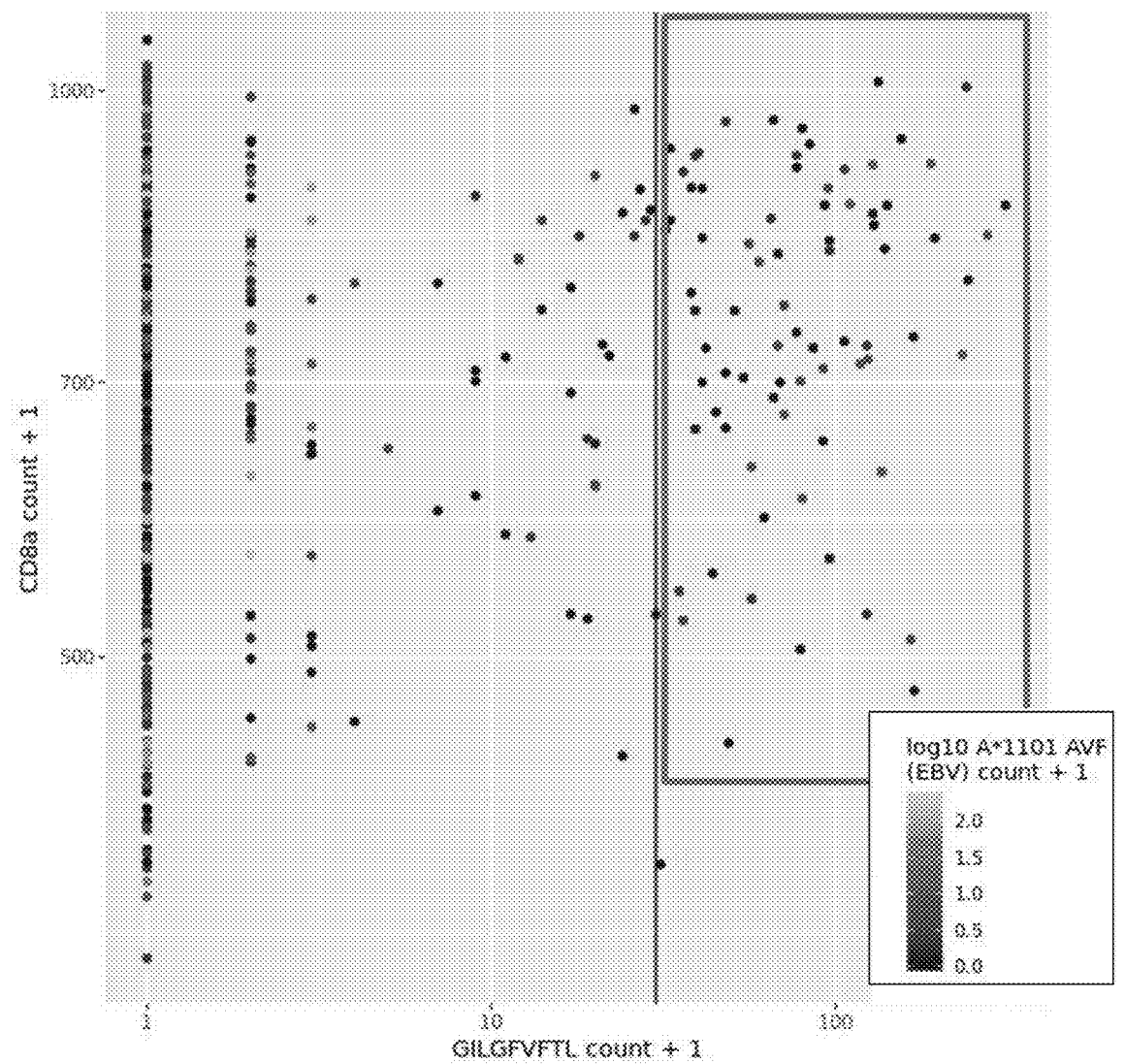
FIG. 23 illustrates a two-way density distribution of the cells in cluster 37 of FIG. 18 in which the x-axis represents the number of instances of the GILGFVFTL antigen bound by an individual cell, the y-axis is a count of the number of instances of the CD8a marker presented by an individual cell, and each point in the two-way density distribution is a different cell in cluster 37 that is colored by log 10 A*1101 AVG (EBV), as well as the clonotypes of cells in a specific region of the distribution that indicate that cluster 37 contains noisy influenza-specific T cells, in accordance with an embodiment of the present disclosure.

FIG. 21 is an expanded view of distribution 1802-37 for cluster 37 of FIG. 18. FIG. 22 illustrates a two-way density distribution of the cells in cluster 37 of FIG. 18 in which the x-axis represents the number of instances of the IVTDFS-VIK/EBV antigen bound by an individual cell, the y-axis is a count of the number of instances of the AVFDRKSDAK/ EBV antigen bound by an individual cell, and each point in the two-way density distribution is a different cell in cluster 37 that is colored by A*0301 KLG/CMV count, as well as the clonotypes of cells in regions 2102 and 2104 of the distribution that indicate that cluster 37 contains EBV-specific T cells. FIG. 23 illustrates a two-way density distribution of the cells in cluster 37 of FIG. 18 in which the x-axis represents the number of instances of the GILGFVFTL antigen bound by an individual cell, the y-axis is a count of the number of instances of the CD8a marker presented by an individual cell, and each point in the two-way density distribution is a different cell in cluster 37 that is colored by log 10 A*1101 AVG (EBV), as well as the clonotypes of cells in a specific region of the distribution that indicate that cluster 37 also contains noisy influenza-specific T cells.

Another distribution shape form in FIG. 18 is exhibited by distribution 1802-10 for cluster 10. Rather than having a left-handed zero inflated tail as in distribution 1802-37 for cluster 37, distribution 1802-10 is a bimodal or even tri-model distribution indicating that some cells in cluster 10 don't bind dextramer and other cells in cluster 10 bind dextramer. However, the cluster itself is not purely antigen-specific. Cluster 10 could therefore be used to iteratively refine the clustering and just allows the cells that are antigen-(here dextramer) specific to fall within refined cluster 10. Alternatively distribution 1802-10 suggests that the cells in cluster 10 are specific to some other antigen and that such cells should be eliminated from the dataset.

Figure 19A:
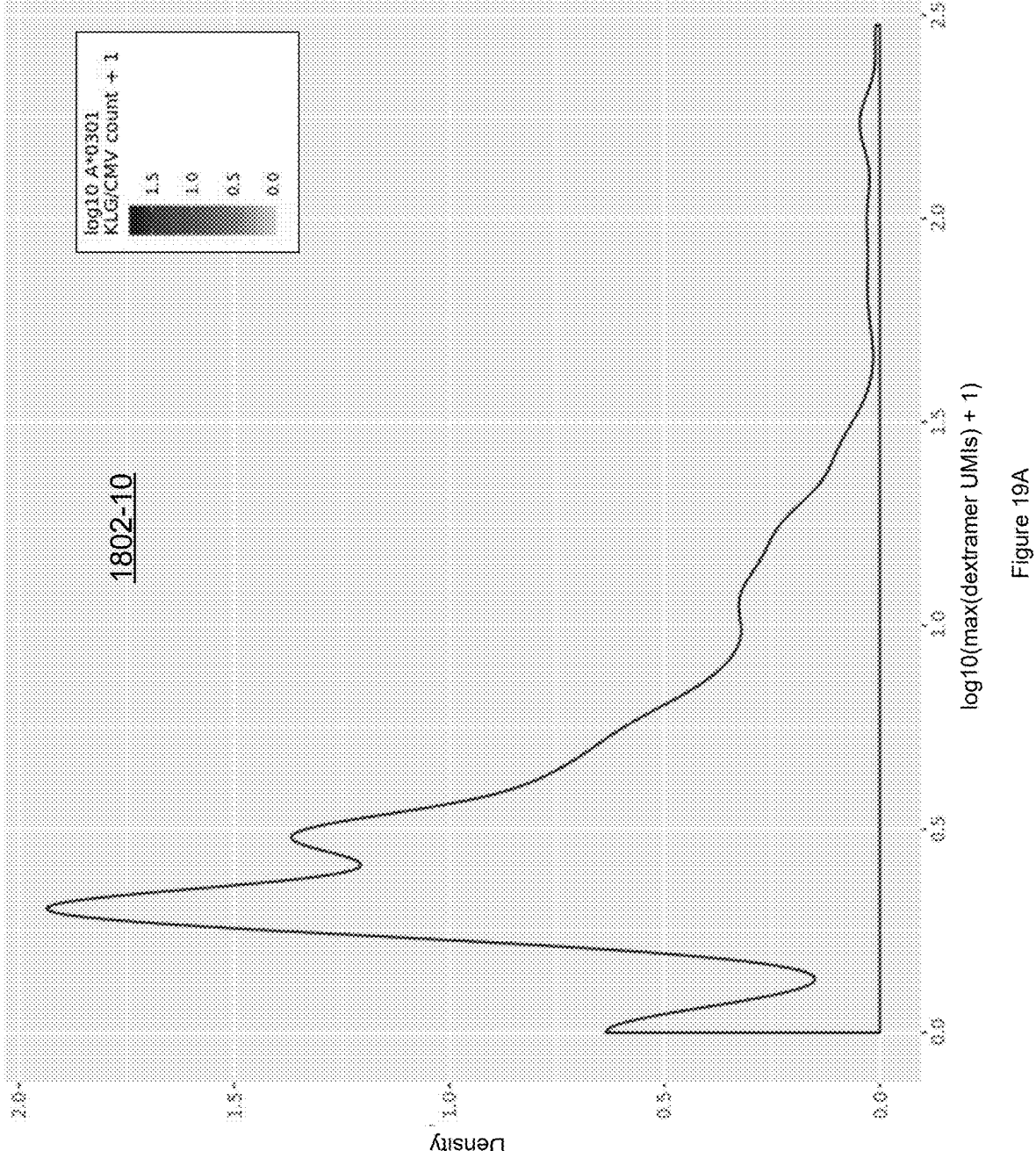
FIG. 19A illustrates the distribution of cells in cluster 10 of FIG. 18, where the distribution is a corresponding count (y-axis) of cells having a given count of dextramer $\log_{10}$ (max (dextramer UMIs)+1) (x-axis) bound to or presented by each cell in cluster 10, in accordance with an embodiment of the present disclosure.
Figure 19B:
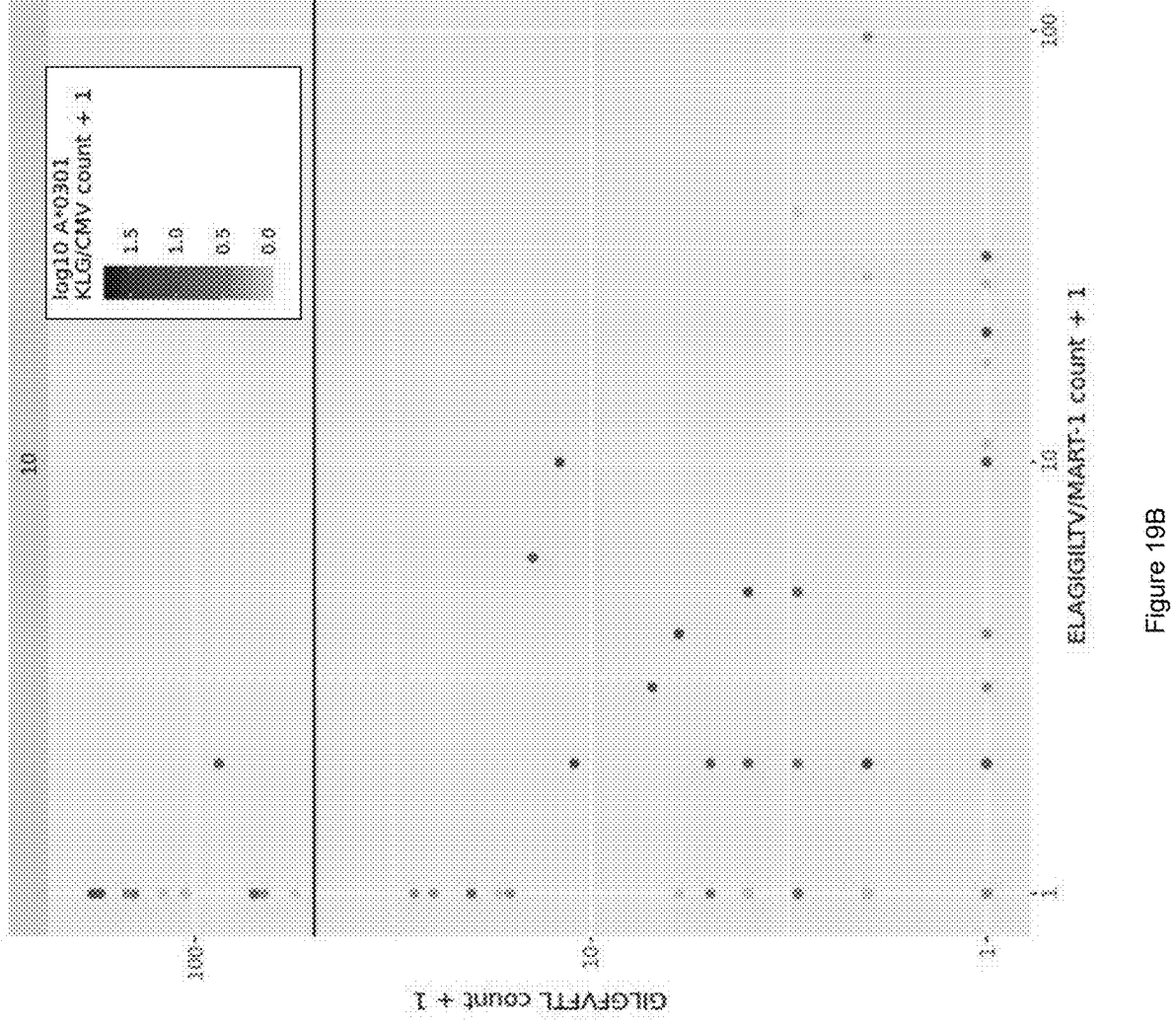
FIG. 19B illustrates a two-way density distribution of the cells in cluster 10 of FIG. 18 in which the x-axis represents the number of instances of the ELAGIGILTV/MART-1 antigen bound by an individual cell, the y-axis is a count of the number of instances of the GILGFVFTL antigen bound by an individual cell, and each point in the two-way density distribution is a different cell in cluster 10 that is colored by $\log_{10}$ A*0301 KLG/CMV count in accordance with an embodiment of the present disclosure.

FIG. 19A is an expanded view of distribution 1802-10 for cluster 10 of FIG. 18. FIG. 19B illustrates a two-way density distribution of the cells in cluster 10 of FIG. 18 in which the x-axis represents the number of instances of the ELA-GIGILTV/MART-1 antigen bound by an individual cell, the y-axis is a count of the number of instances of the GILGFVFTL antigen bound by an individual cell, and each point in the two-way density distribution is a different cell in cluster 10 that is colored by log 10 A*0301 KLG/CMV count. FIG. 20 illustrates the clonotypes represented in the cells of cluster 10 of FIG. 18, which indicate that the cluster contains influenza-specific T cells in accordance with an embodiment of the present disclosure.

Another shape form in FIG. 18 is exhibited by distribution 1802-51 for cluster 51. Rather than having a left-handed zero inflated tail as in distribution 1802-37 for cluster 37, distribution 1802-51 is right shifted indicating that the cells in cluster 51 are binding dextramer and that they are binding the antigen specifically. Cluster 51 therefore represents a high-quality antigen-specific, clean cluster of cells. Thus, all the T cell receptors of the T cells in cluster 51 have specificity to the indicated molecule (here, dextramer) and just the indicated molecule.

Figure 24:
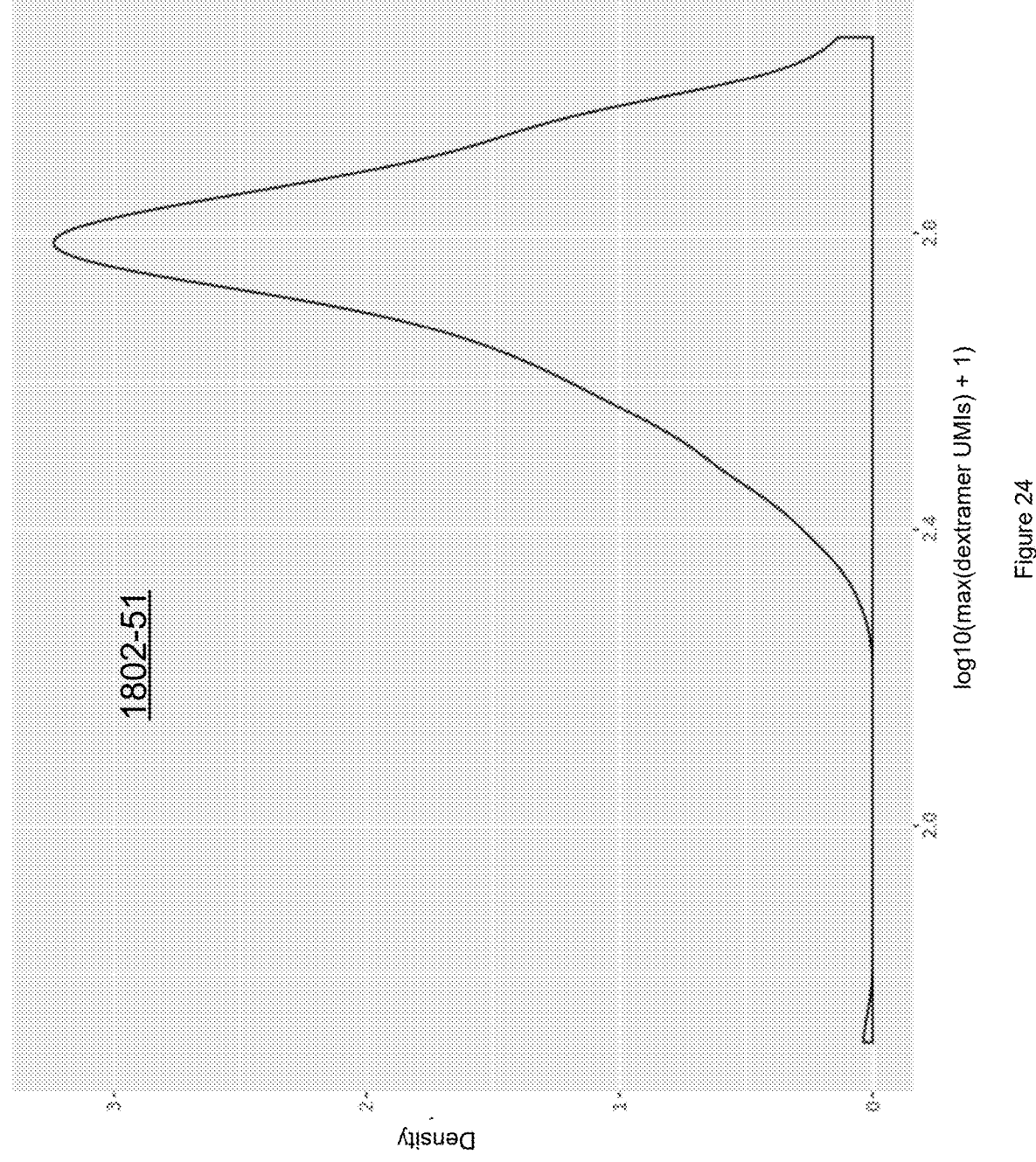
FIG. 24 illustrates the distribution of cells in cluster 51 of FIG. 18, where the distribution is a corresponding count (y-axis) of cells having a given count of dextramer log 10 (max (dextramer UMIs)+1) (x-axis) bound to or presented by each cell in cluster 51 in accordance with an embodiment of the present disclosure.
Figure 25:
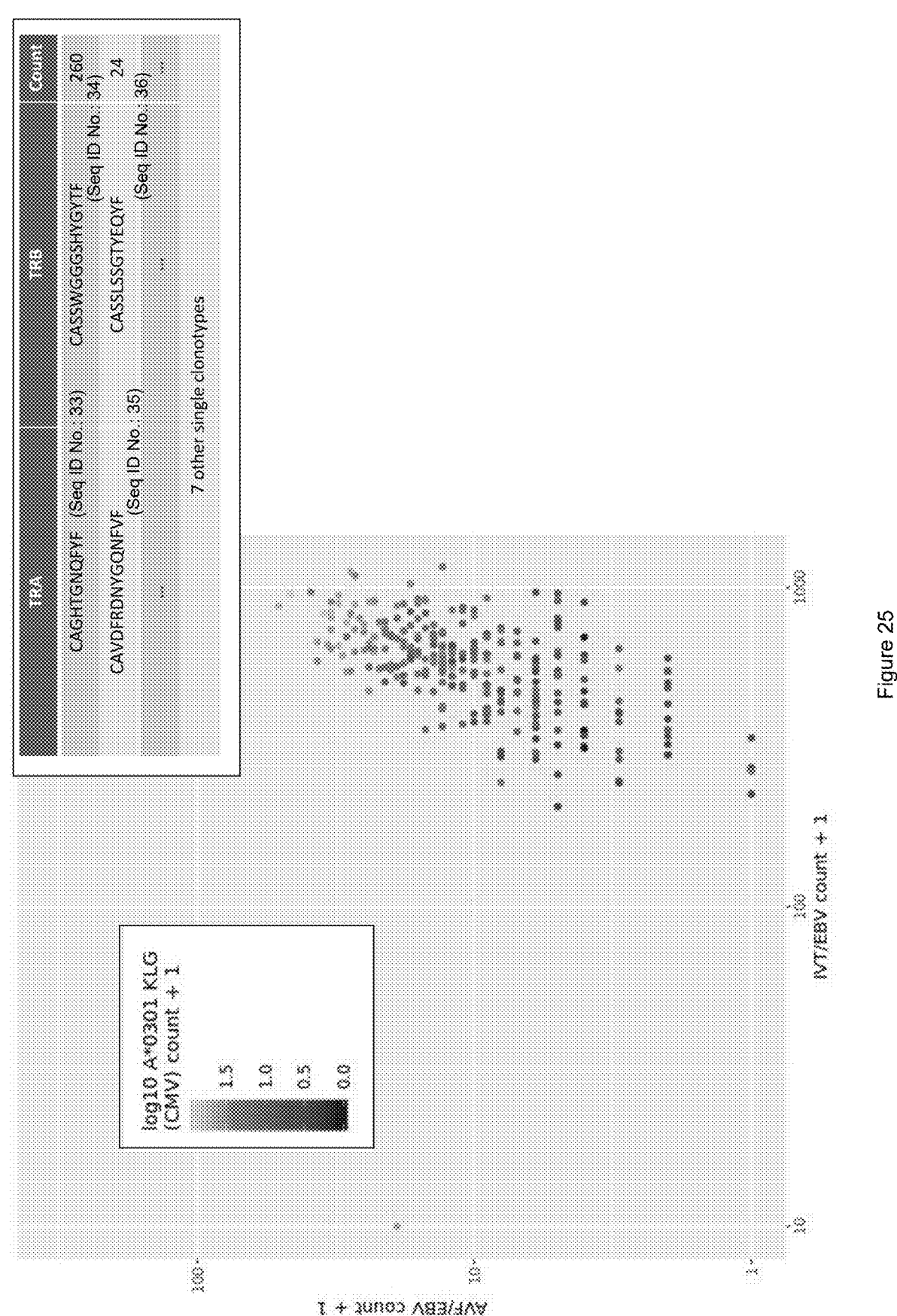
FIG. 25 illustrates a two-way density distribution of the cells in cluster 51 of FIG. 18 in which the x-axis represents the number of instances of the IVT/EBV antigen bound by an individual cell, the y-axis is a count of the number of instances of the AVF/EBV antigen bound by an individual cell, and each point in the two-way density distribution is a different cell in cluster 51 that is colored by A*0301 KLG (CMV) count, as well as the clonotypes of cells in cluster 51 that indicate that cluster 51 is highly enriched for two EBV-specific clonotypes, in accordance with an embodiment of the present disclosure.

FIG. 24 is an expanded view of distribution 1802-51 for cluster 51 of FIG. 18. FIG. 25 illustrates a two-way density distribution of the cells in cluster 51 of FIG. 18 in which the x-axis represents the number of instances of the IVT/EBV antigen bound by an individual cell, the y-axis is a count of the number of instances of the AVF/EBV antigen bound by an individual cell, and each point in the two-way density distribution is a different cell in cluster 51 that is colored by A*0301 KLG (CMV) count, as well as the clonotypes of cells in cluster 51 that indicate that cluster 51 is highly enriched for two EBV-specific clonotypes.

FIGS. 18 through 25 illustrate how distributions of clustered cells can be used to determine the antigen specificity of cells in a particular cluster of cells. In the present disclosure such information is reinforced with a measure of clonal expansion in such clusters. In some embodiments, the measure of clonal expansion is determined from the total number of unique immune cell receptor clonotypes detected within the cells of the cluster and the total number of immune cell receptor clonotypes detected within the cells of the cluster. In some embodiments, for instance using barcoding as described above, the total number of unique immune cell receptor clonotypes detected within the cells serves to represent the number of immune cells detected in the respective cluster. The phrase "clonal expansion" refers to the proliferation of B cells and T cells activated by clonal selection in order to produce a clonal population of daughter cells with the same antigen specificity and functional capacity. In the case of T cells, this antigen specificity is exact at the nucleotide and protein level and in the case of B cells this antigen specificity can be exact at the nucleotide and protein level or mutated relative to the parent population by mutations at the nucleotide level (and by extension the protein level). This enables the body to have sufficient numbers of antigen-specific lymphocytes to mount an effective immune response. The phrase "clonal selection" refers to the selection and activation of specific B cells and T cells by the binding of epitopes to B cell receptors or T cell receptors with a corresponding fit and the subsequent elimination (negative selection) or licensing for clonal expansion (positive selection) of a B or T cell after binding of an antigenic determinant.

As an example, FIG. 30 illustrates for cluster 3000-2: (i) a distribution of a corresponding count of a first immunogenic feature bound to or presented by each cell in the respective cluster (density of Log 10 (max (UMI)+1), (ii) the total number of unique immune cell receptor clonotypes detected within the different subset of the plurality of immune cells represented by the respective cluster, and (iii) the total number of immune cell receptor clonotypes detected within the different subset of the population of cells represented by the respective cluster (e.g., which serves to represent the number of immune cells in the cluster) to determine whether the different subset of the population of cells represented by the respective cluster is antigen-specific for the first immunogenic feature.

In some embodiments, the total number of unique immune cell receptor clonotypes detected within the different subset of the plurality of immune cells represented by the respective cluster and the total number of immune cell receptor clonotypes detected within the different subset of the population of cells represented by the respective cluster are used to calculate the degree of clonal expansion within the cluster as discussed above in conjunction with block 3654. The degree of clonal expansion is indicative of a potential therapeutic and/or diagnostic application. Moreover, in a commercial setting where a particular T cell or B cell receptor is being developed, the degree of clonal expansion provides a selective capacity for such development. Thus the present disclosure combines the novel measure of determining antigen specificity through analysis of the distribution of a corresponding count of the first immunogenic feature bound to or presented by each cell in the respective cluster (as discussed above and exemplified in FIGS. 18 through 25) and the clonal expansion overlayed in the same space (e.g., as illustrated for cluster 3000-2 of FIG. 30) to inform where the strongly expanded antigen specific populations of immune cells are in a population of immune cells (e.g., which cluster they are in).

Figure 32:
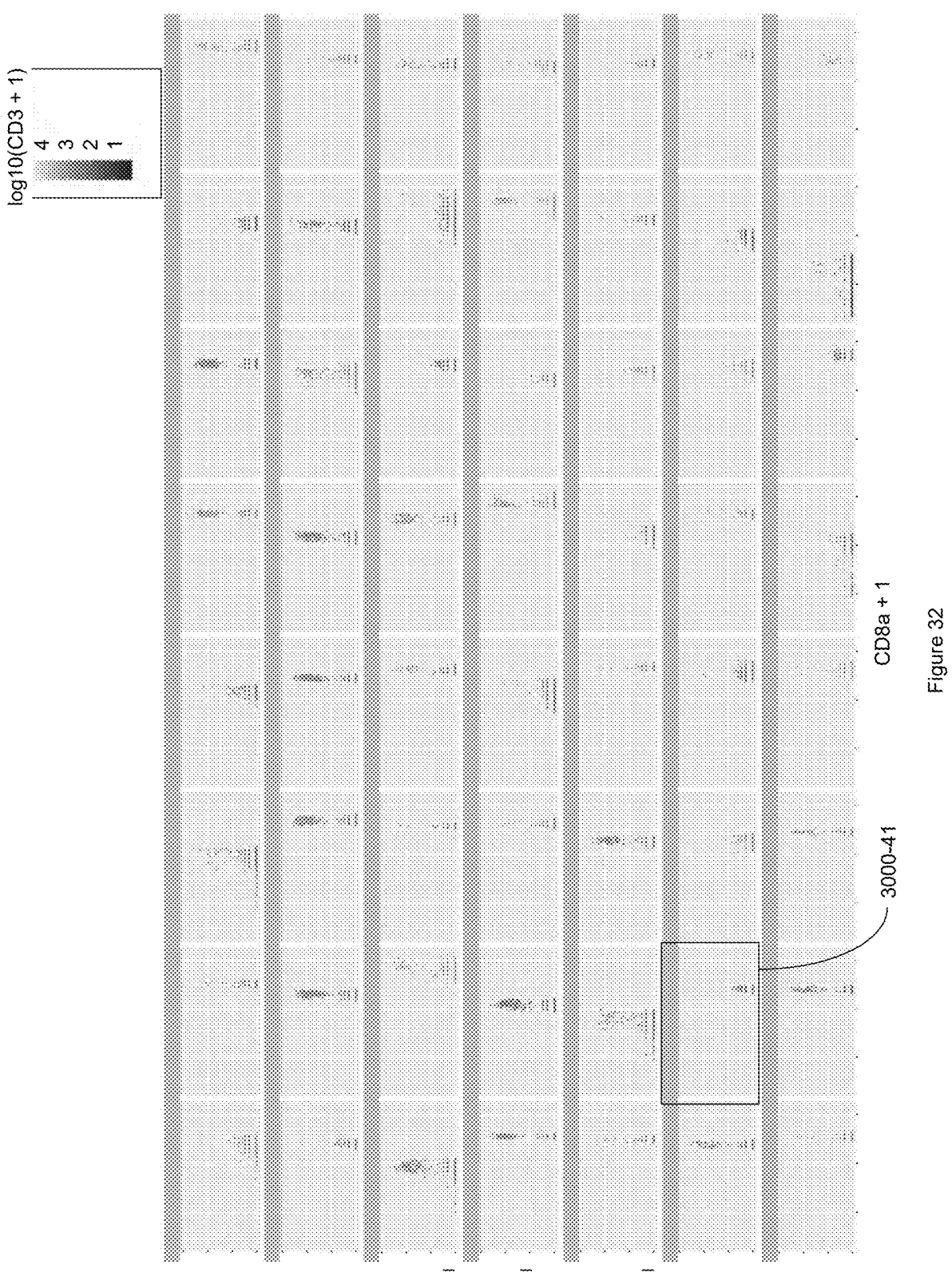
FIG. 32 illustrates a two-way density distribution of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of A0201_GILGFVFTL_Flu-MP-influenza antigen bound by an individual cell, and each point in the Figure is a different cell in the population of cells that is colored by its $\log_{10}$ (CD3+1) count, where CD3 is the number of CD3 markers presented by a respective cell.
Figure 33:
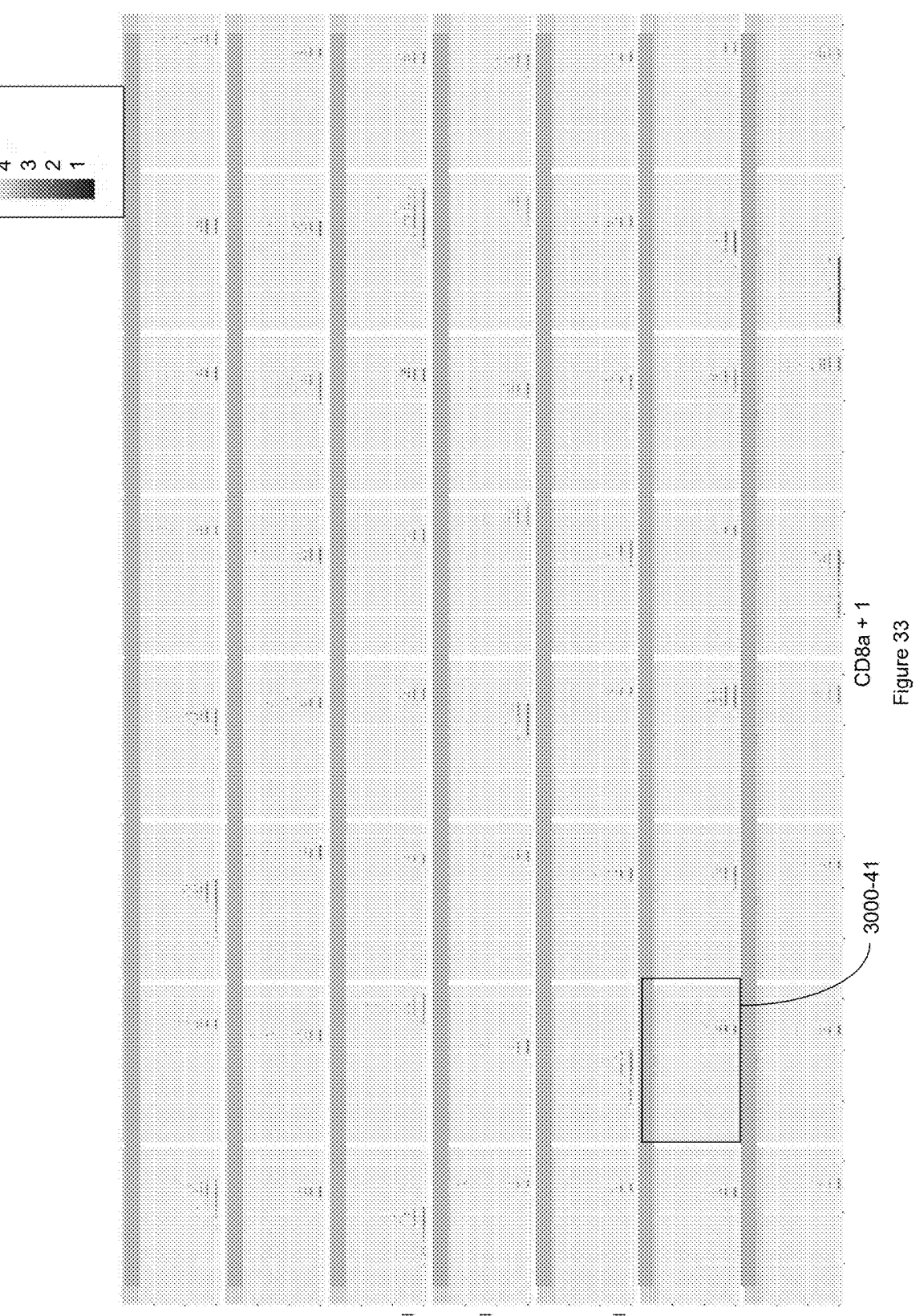
FIG. 33 illustrates a two-way density distribution of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of A0201_GLCTLVAML_BMLF1 EBV antigen bound by an individual cell, and each point in the Figure is a different cell in the population of cells that is colored by its $\log_{10}$ (CD3+1) count, where CD3 is the number of CD3 markers presented by a respective cell.
Figure 34:
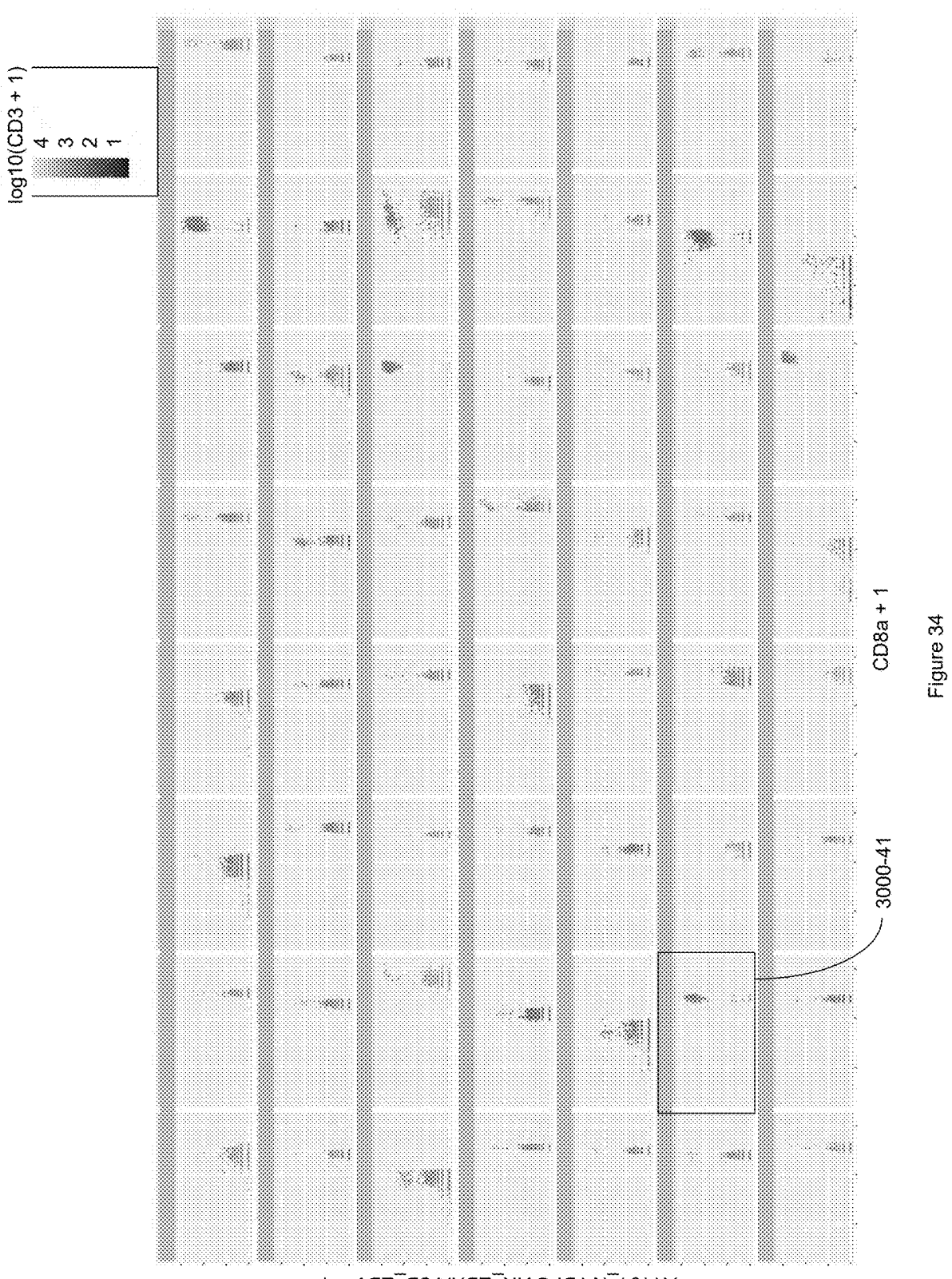
FIG. 34 illustrates a two-way density distribution of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of A1101_IVTDFSVIK_EBNA-3B EBV antigen bound by an individual cell, and each point in the Figure is a different cell in the population of cells that is colored by its $\log_{10}$(CD3+1) count, where CD3 is the number of CD3 markers presented by a respective cell.

Cluster 3000-41 of FIG. 30 illustrates the method. The distribution illustrates a strong-right shifted population indicating antigen specificity. FIG. 30 illustrates a distribution of cells in each cluster in a plurality of clusters that were obtained upon clustering the population of cells of FIG. 26 based on the number and types of markers presented by such cells, where each distribution is a corresponding count (x-axis) of cells $\log_{10}(\max (UMI)+1)$ (x-axis) and y-axis is density. There are 606 cells in cluster 3000-41, and there are 47 different clonotypes across of those cells giving a clonal expansion of 92.244. FIG. 31 illustrates a two-way density distribution of cells in each cluster in the plurality of clusters of FIG. 30, in which the x-axis represents the number of instances the CD8a marker presented by an individual cell, the y-axis is a count of the number of B0B01_RAKFKQLL_BZLF1 EBV antigen bound by an individual cell, and each point in the Figure is a different cell in the population of cells that is colored by its $\log_{10} (CD3+1)$ count, where CD3 is the number of CD3 markers presented by a respective cell. FIG. 31 illustrates that for cluster 3000-41 there is little to no signal for B0B01_RAKFKQLL_BZLF1 EBV antigen. FIG. 32 illustrates a two-way density distribution of cells in each cluster in the plurality of clusters of FIG. 30, in which the x-axis represents the number of instances the CD8a marker presented by an individual cell, the y-axis is a count of the number of A0201_GILGFVFTL_Flu-MP-influenza antigen bound by an individual cell, and each point in the Figure is a different cell in the population of cells that is colored by its $\log_{10} (CD3+1)$ count, where CD3 is the number of CD3 markers presented by a respective cell. FIG. 32 illustrates that for cluster 3000-41 there is little to no signal for the A0201_GILGFVFTL_Flu-MP-influenza antigen. FIG. 33 illustrates a two-way density distribution of cells in each cluster in the plurality of clusters of FIG. 30, in which the x-axis represents the number of instances the CD8a marker presented by an individual cell, the y-axis is a count of the number of A0201_GLCTLVAML_BMLF1 EBV antigen bound by an individual cell, and each point in the Figure is a different cell in the population of cells that is colored by its $\log_{10}$ (CD3+1) count, where CD3 is the number of CD3 markers presented by a respective cell. FIG. 33 illustrates that for cluster 3000-41 there is little to no signal for the A0201_GLCTLVAML_BMLF1 EBV antigen. FIG. 34 illustrates a two-way density distribution of cells in each cluster in the plurality of clusters of FIG. 30, in which the x-axis represents the number of instances the CD8a marker presented by an individual cell, the y-axis is a count of the number of A1101_IVTDFSVIK_EBNA-3B EBV antigen bound by an individual cell, and each point in the Figure is a different cell in the population of cells that is colored by its $\log_{10}$ (CD3+1) count, where CD3 is the number of CD3 markers presented by a respective cell. FIG. 34 illustrates that for cluster 3000-41 there is a boosted signal, well-above background for the antigen A1101_IVTDFSVIK_EBNA-3B EBV. The data for cluster 3000-41 in FIGS. 30 and 34, together with the negative data of FIGS. 31-33, establish that the population of cells of cluster 3000-41 recognized the A0201_GLCTLVAML_BMLF1 EBV antigen. In FIG. 34, an average score of 100 across the cells of the cluster is considered to be a clonally pure population.

Figure 26:
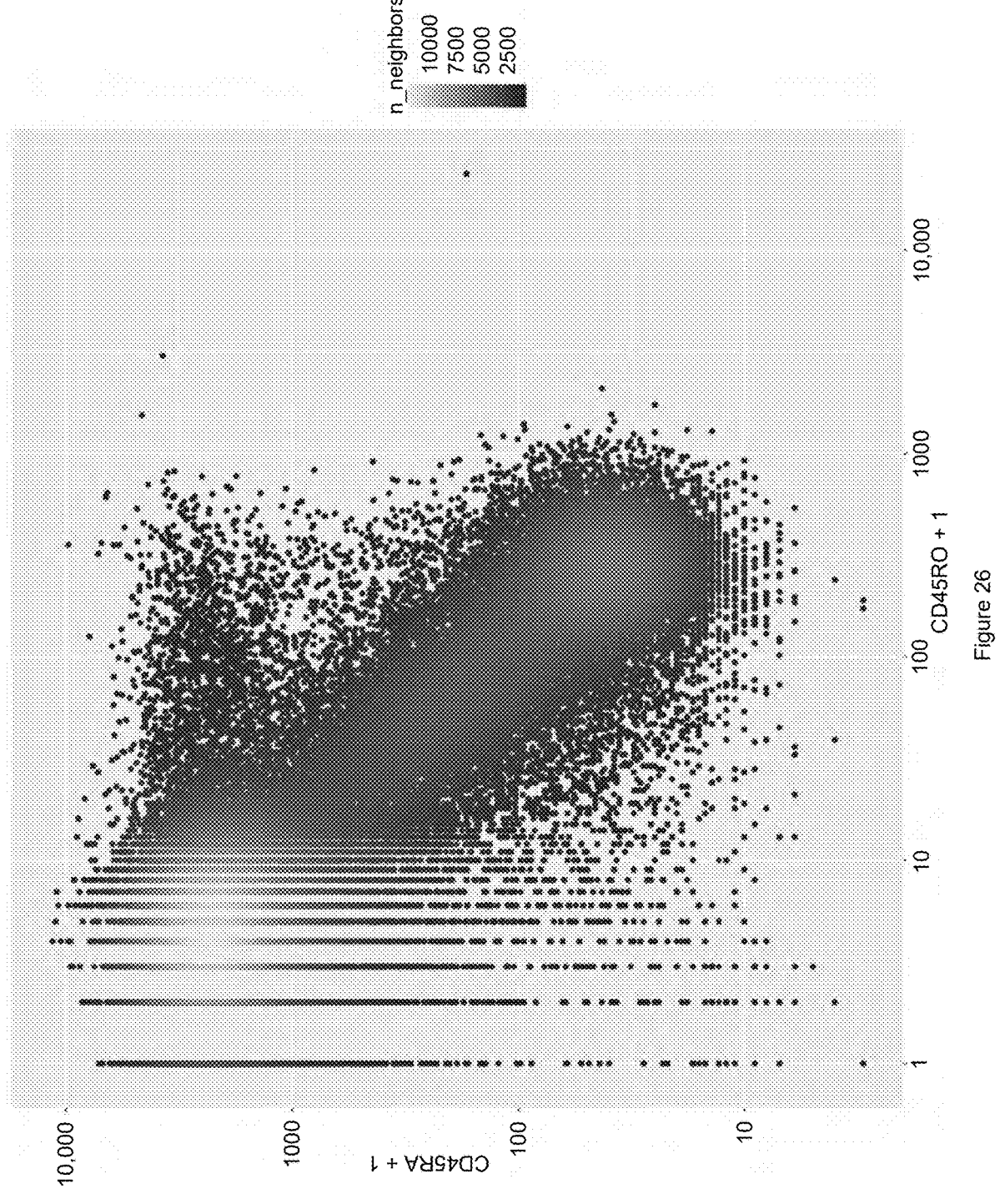
FIG. 26 illustrates a two-way density distribution for a population of cells: —naïve cells (CD45RA+CCR7+), central memory cells (CD45RO+CCR7+), effector cells (CD45RO+CCR7−), and TemRA cells (CD45RA+CCR7−), in which each point in the scatterplot represents a respective cell in the population of cells, the x-coordinate is a count of the CD45RO marker presented by the respective cell, the y-coordinate is a count of the CD45RA marker presented by the respective cell, and the color of each point indicates the number of nearest neighbors the corresponding respective cell has in the density distribution in accordance with an embodiment of the present disclosure.
Figure 27:
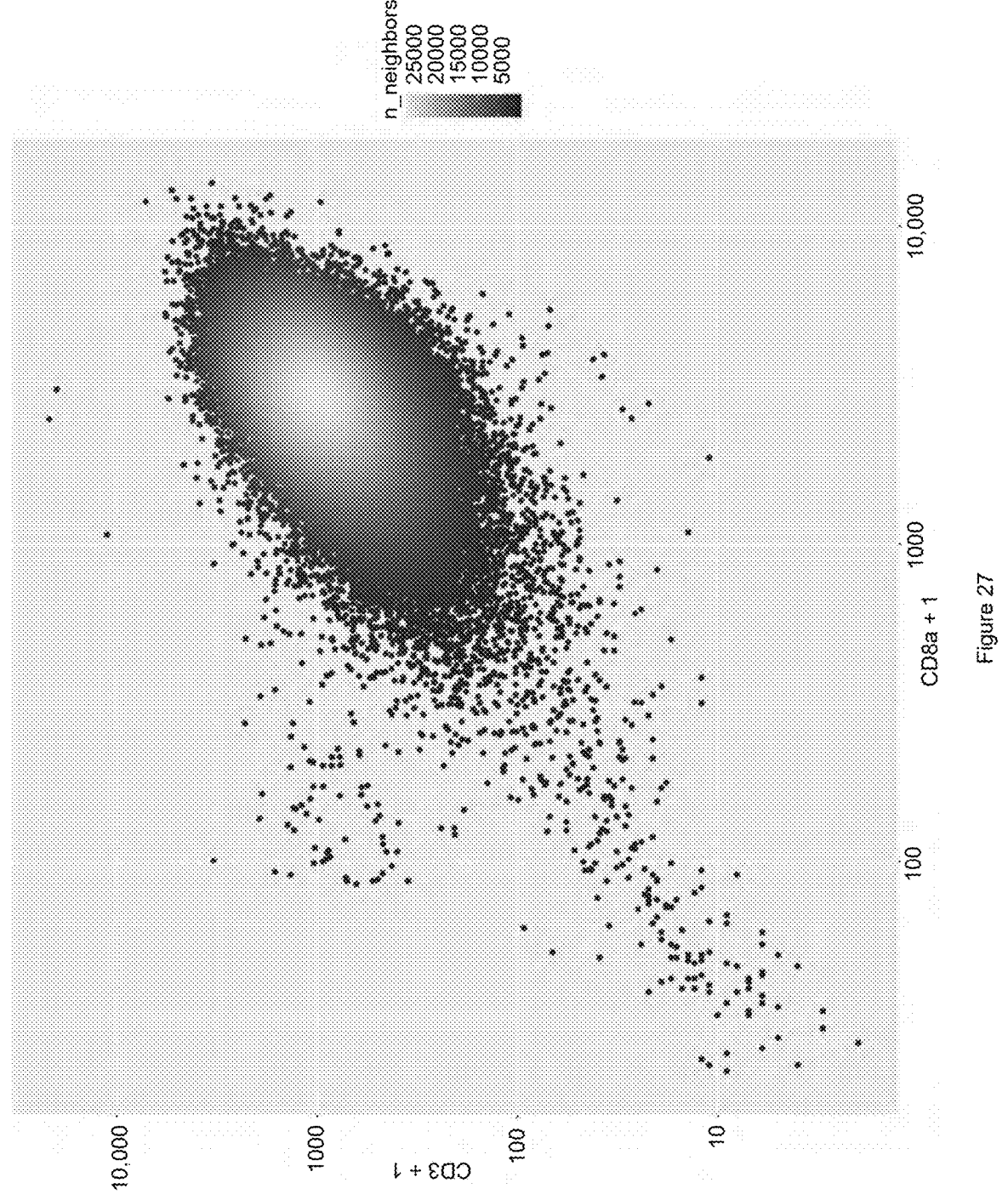
FIG. 27 illustrates another two-way density distribution for the population of cells of FIG. 26 in which each point in the scatterplot represents a respective cell in the population of cells, the x-coordinate is a count of the CD8a marker presented by the respective cell, the y-coordinate is a count of the CD3 marker presented by the respective cell, and the color of each point indicates the number of nearest neighbors the corresponding respective cell has in the density distribution in accordance with an embodiment of the present disclosure.
Figure 28:
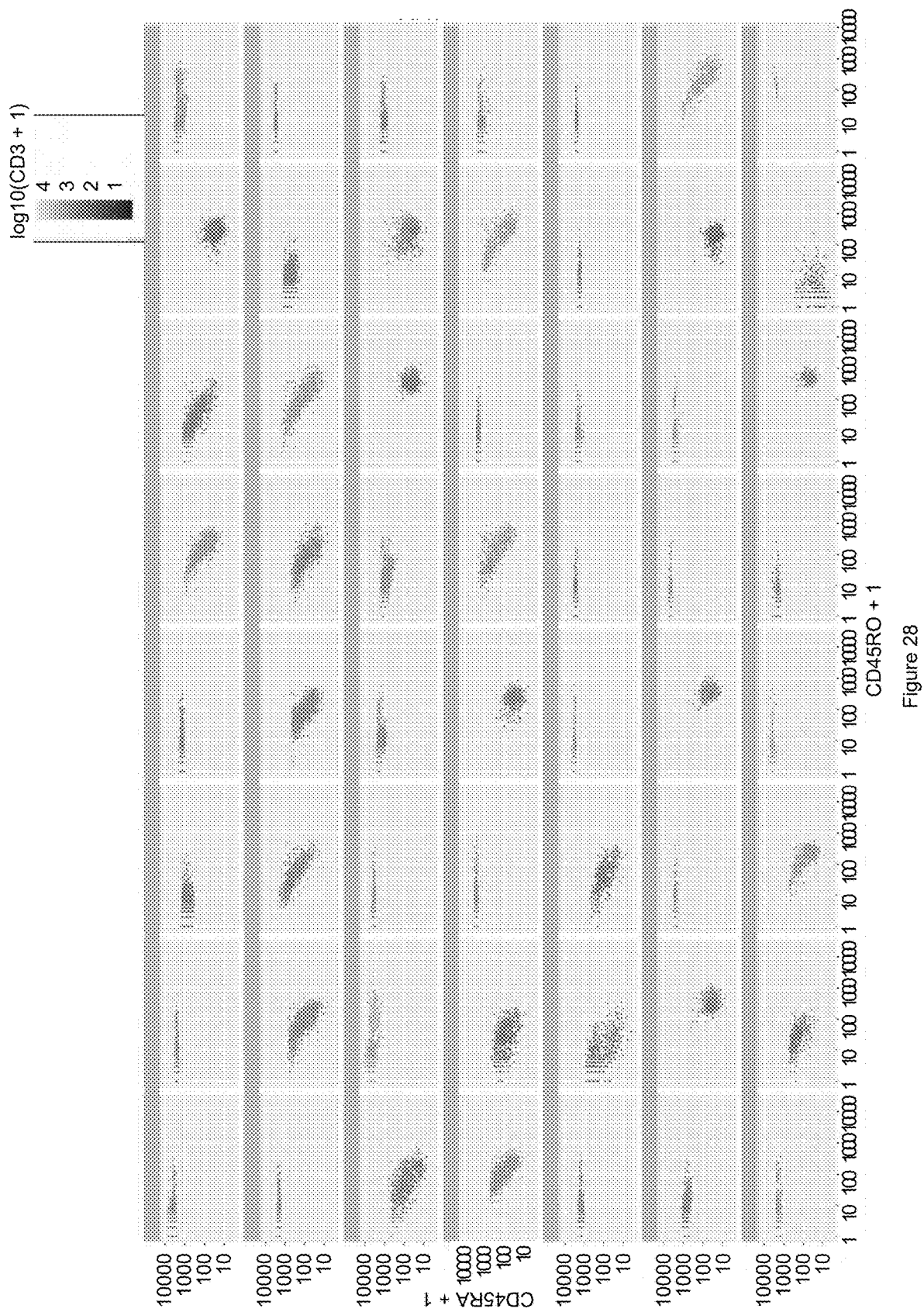
FIG. 28 illustrates a two-way density distribution of cells in each cluster in a plurality of clusters that were obtained upon clustering the population of cells of FIG. 26 based on the number and types of markers presented by such cells, in which the x-axis represents the number of instances of the CD45RO marker presented by an individual cell, the y-axis is a count of the number of instances of the CD45RA marker presented by an individual cell, and each point in the Figure is a different cell in the population of cells that is colored by list log 10 (CD3+1) count, where CD3 is the number of CD3 markers presented by a respective cell.
Figure 29:
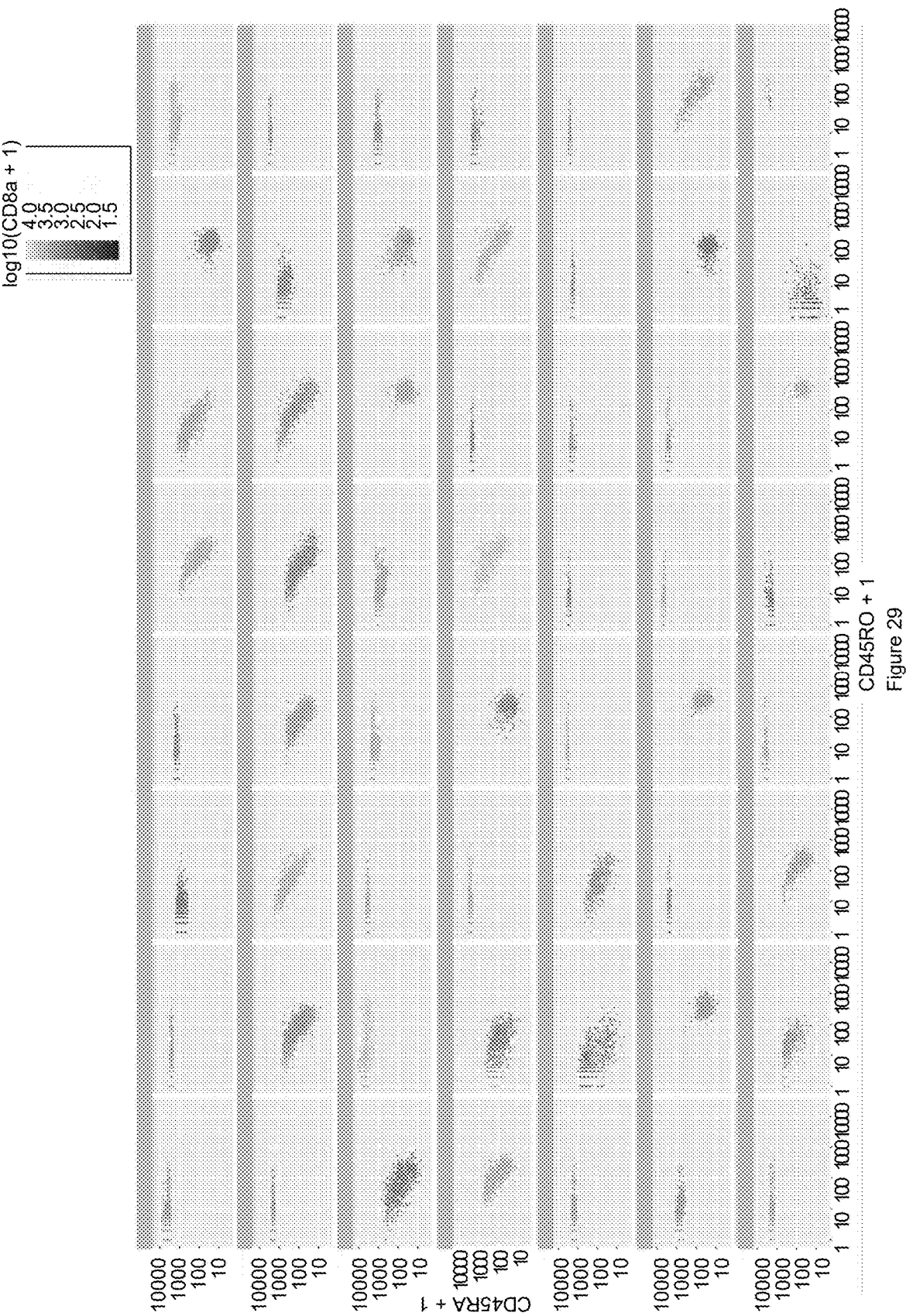
FIG. 29 illustrates a two-way density distribution of cells in each cluster in a plurality of clusters that were obtained upon clustering the population of cells of FIG. 26 based on the number and types of markers presented by such cells, in which the x-axis represents the number of instances of the CD45RO marker presented by an individual cell, the y-axis is a count of the number of instances of the CD45RA marker presented by an individual cell, and each point in the Figure is a different cell in the population of cells that is colored by its $\log_{10}$ (CD8a+1) count, where CD8a is the number of CD8a markers presented by a respective cell.
Figure 35:
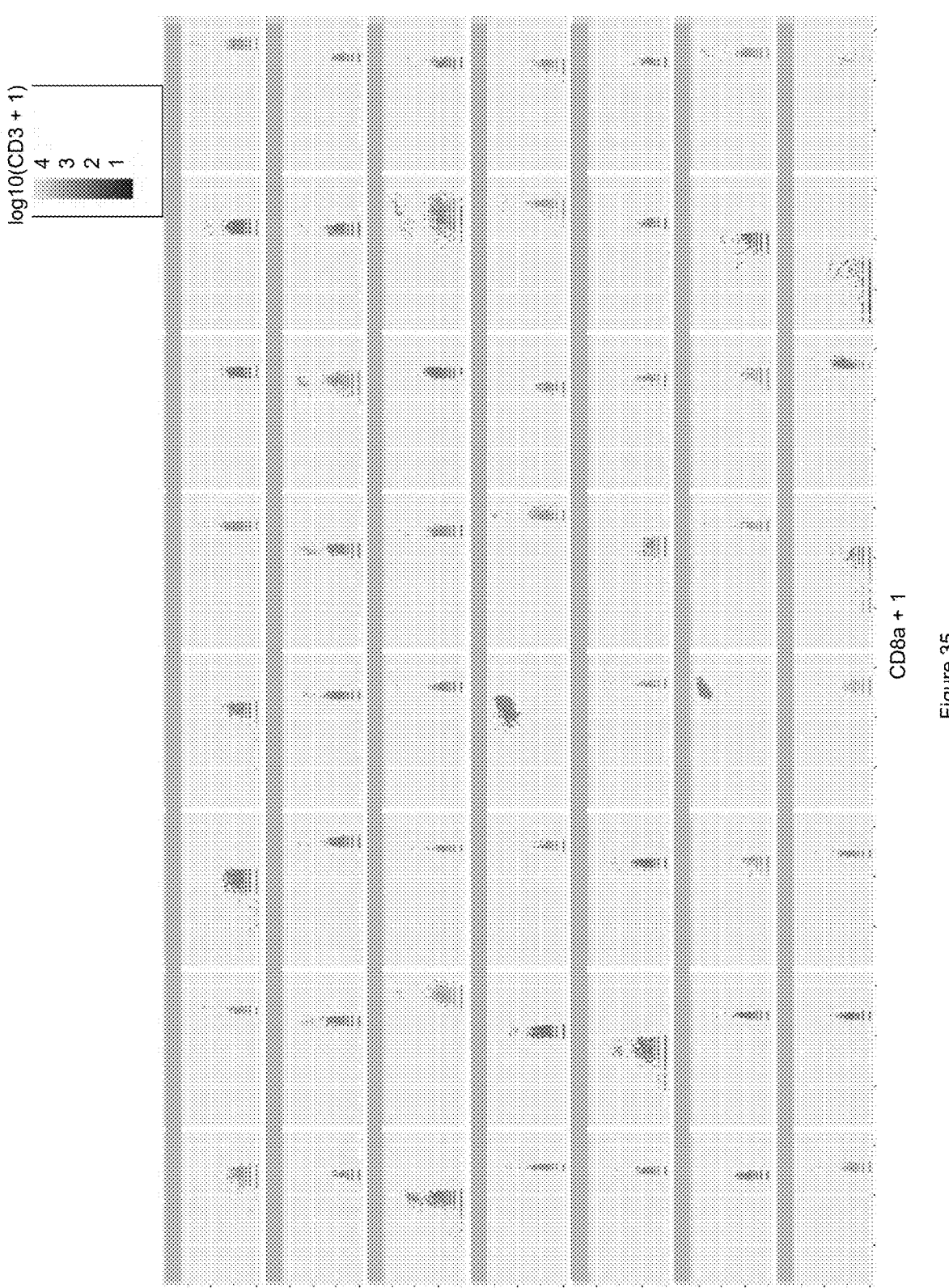
FIG. 35 illustrates a two-way density distribution of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of A1101_AVFDRKSDAK_EBNA_EBNA-3B EBV antigen bound by an individual cell, and each point in the Figure is a different cell in the population of cells that is colored by its log 10 (CD3+1) count, where CD3 is the number of CD3 markers presented by a respective cell.

FIG. 35 illustrates a two-way density distribution of cells in each cluster in a plurality of clusters that were obtained upon clustering the population of cells of FIG. 26 based on the number and types of markers presented by such cells, in which the x-axis represents the number of instances the CD8a marker presented by an individual cell, the y-axis is a count of the number of A1101_AVFDRKSDAK_EBNA_EBNA-3B EBV antigen bound by an individual cell, and each point in the Figure is a different cell in the population of cells that is colored by its log 10 (CD3+1) count, where CD3 is the number of CD3 markers presented by a respective cell.

Example 2. This example provides an algorithm for clonotyping that is disclosed in U.S. Patent Application No. 61/011,783, entitled "Systems and Methods for Identifying Adaptive Immune Cell Clonotypes," filed Apr. 17, 2020, and on the Internet at Github at 10×Genomics/enclone, last accessed Aug. 31, 2020, each of which is hereby incorporated by reference.

The algorithm uses single-cell data to identify single B cells that are highly likely to have originated from the same original progenitor. The algorithm attempts to identify donor-specific mutations in V genes that are shared across multiple clonotypes and multiple single cells. Exclusion of such germline mutations allows for the accurate approximation of mutations in a given set of B cells that arose through somatic hypermutation, and could also be used to haplotype and genotype donors as described in tools that have been developed for this purpose using bulk data. The algorithm also identifies and removes noise from background VDJ rearrangements that are detected at low levels (e.g. there is low confidence that a given VDJ rearrangement is genuine) or a result of technical noise (a VDJ RNA rearrangement from one cell floats into another cell's partition). Removal of the latter noise is important because clonotypes act as noise amplifiers: with many cells, there are many opportunities to introduce spurious chains. A priori, a clonotype is described by a matrix having over a thousand columns and one row per cell assayed (often over a hundred). As such, the matrix cannot be viewed at once. In some embodiments, the algorithm compresses the matrix in both directions. (a1) Only columns having a difference from the reference sequence are shown (plus particularly interesting regions, notably CDR3). (a2) Columns are shown in amino acid space to reduce space and expose biological meaning; these amino acids are colored by codon so that no information is lost. Colors are chosen from a colorblind-friendly palette. (b) Rows corresponding to identical transcripts are merged. In the vast majority of cases these compressions reduce the clonotype display to a single viewable region. Such displays and visualization is further disclosed in U.S. Provisional Patent Application No. 63/011,779, entitled "Systems and Methods for Visualizing Adaptive Immune Cell Clonotyping Data," filed Apr. 17, 2020, which is hereby incorporated by reference.

In the algorithm, the donor's germline sequences for V segments are identified using the same single-cell V(D)J data. These can be found so long as there are enough cells (and depending on the particular V segment), and exclusive of the last ~15 bases of the V segment, which are involved in recombination. Then, an exact subclonotype is defined to be a set of cells having identical transcripts. For each such pair of exact subclonotypes for which the CDR3 sequences have the same length and the full V through J sequences have the same length (both applied to each chain), the number of shared differences from the reference sequence, and the number of independent differences from the reference sequence, is determined. The probability p that, given the total number of differences, at least that many shared differences occur by chance, is computed. A low probability is a sign that the two exact subclonotypes belong in the same clonotype. The number of differences between the two exact subclonotypes' CDR3 sequences is computed. The total number N of hypothetical CDR3 sequences that could be obtained my making that many arbitrary changes to one of the sequences is then determined. A low value of N is a sign that the two exact subclonotypes belong in the same clonotype. To 'join' two subclonotypes (e.g. assert that they lie in the same clonotype), requires that p*N is less than an arbitrary threshold (e.g., 1,000,000). For hypothetical clonotypes that would be created, having just two cells, a higher thresholds is used, because the expectation is that an expanded clonotype is relatively large so these tiny clonotypes are enriched for errors.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A method of identifying cells that are antigen-specific for a first immunogenic feature, the method comprising:

at a computer system comprising one or more processors and a memory:

A) obtaining, in electronic form, an immunogenic feature-by-cell data structure, at a browser module for the computer system, that comprises, for each respective immune cell in a population of cells, and for each respective immunogenic feature in a set comprising at least 20 immunogenic features, a corresponding count that represents an extent to which the respective immune cell binds to or presents the respective immunogenic feature, wherein:

the set of immunogenic features includes the first immunogenic feature, and for each respective immunogenic feature in the set of immunogenic features, the population of immune cells includes at least one immune cell that is bound to or presents the respective immunogenic feature;

B) clustering the population of immune cells based on similarity of their corresponding sets of counts across the set of immunogenic features, thereby generating a plurality of clusters, wherein each cluster in the plurality of clusters is a unique subset of the population of immune cells;

C) for each respective cluster in the plurality of clusters:

obtaining a total number of unique immune cell receptor clonotypes detected within the cluster, based on per-cell experimental measurements from the immunogenic feature-by-cell data structure;

obtaining a total number of immune cell receptor clonotypes detected within the cluster, based on per-cell experimental measurements from the immunogenic feature-by-cell data structure;

determining a quantitative measure of clonal expansion within the cluster, from (i) the total number of unique immune cell receptor clonotypes and (ii) the total number of immune cell receptor clonotypes; and computing a distribution of the counts of the first immunogenic feature bound to or presented by each cell in the respective cluster, based on per-cell experimental measurements of binding or presentation from the immunogenic feature-by-cell data structure; and (D) selecting a first cluster, in the plurality of clusters, as antigen-specific for the first immunogenic feature, based on (i) the measure of clonal expansion, displayed by the at a browser module for the computer system module, for the first cluster being higher than the measure of clonal expansion of other clusters in the plurality of clusters, and (ii) the distribution, displayed by the browser module, of the corresponding count of the first immunogenic feature for the first cluster indicating that the per cell count of the first immunogenic feature bound to or presented by cells in the first cluster is higher than in cells of other clusters in the plurality of clusters.

2. The method of claim 1, wherein the population of cells is from a single subject.

3. The method of claim 1, wherein more than ten cells in a respective cluster have the same clonotype.

4. The method of claim 1, wherein the total number of unique immune cell receptor clonotypes in a respective cluster comprises 100 clonotypes.

5. The method of claim 1, wherein the population of cells consists of B cells or consists of T cells.

6. The method of claim 1, wherein

The immunogenic feature-by-cell data structure is in the form of a two-dimensional l×m features matrix, l is a positive integer of 1000 or greater that represents the number of cells in the population of cells, m is a positive integer of 20 or greater that represents the number of immunogenic features, and each element in the two-dimensional l×m features matrix uniquely represents a different immunogenic feature in the plurality of immunogenic features and a different cell in the population of cells and provides a count of the number of the different immunogenic feature that has been detected as bound to or presented by the different cell.

7. The method of claim 1, wherein the clustering has a time complexity of at least $O(n)$ or $O(\log n)$, and n is a product of (i) a number of cells in the population of cells and (ii) a number of immunogenic features in the plurality of immunogenic features.

8. The method of claim 1, wherein the population of cells comprises at least 3,000 cells.

9. The method of claim 1, wherein the plurality of immunogenic features comprises at least 40 immunogenic features.

10. The method of claim 1, wherein each immunogenic feature in the plurality of immunogenic features is a cell surface feature.

11. The method of claim 10, wherein each cell surface feature is a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T cell receptor, a T cell receptor, a B cell receptor, a chimeric antigen receptor, a fusion protein, a gap junction, or an adherens junction.

12. The method of claim 1, wherein the distribution of the counts of the first immunogenic feature bound to or presented by each respective cell in the respective cluster is a transformed or untransformed count of the first immunogenic feature bound to or presented by the respective cell.

13. The method of claim 1, wherein the distribution of the counts of the first immunogenic feature bound to or presented by each respective cell in the respective cluster is a transformed count of the first immunogenic feature bound to or presented by the respective cell, wherein the transformation is $\log_{10}$, $\log_2$, or square root.

14. The method of claim 1, wherein
the at least 1,000 immune cells are B cells,
the population of cells further comprises non-immune cells,
the distribution is a pairwise distribution of the first immunogenic feature against a second immunogenic feature, and
the second immunogenic feature is associated with B cells.

15. The method of claim 1, wherein
the at least 1,000 immune cells are T cells,
the population of cells further comprises non-immune cells,
the distribution is a pairwise distribution of the first immunogenic feature against a second immunogenic feature, and
the second immunogenic feature is associated with T cells.

16. The method of claim 1, wherein
the at least 1,000 immune cells are B cells, and
the first immunogenic feature is associated with B cells.

17. The method of claim 1, wherein
the at least 1,000 immune cells are T cells, and
the first immunogenic feature is associated with T cells.

18. The method of claim 1, the method further comprising:
acquiring the corresponding count of the respective immunogenic feature bound to or presented by each immune cell in the population of cells through single-cell sequencing in which the first immunogenic feature is assigned a unique barcode.

19. The method of claim 18, the method further comprising:
determining that the respective cluster includes a mixture of cells that that are antigen-specific for the first immunogenic feature and cells that are not antigen-specific for the first immunogenic feature, and
using the distribution of the corresponding count of the first immunogenic feature bound to or presented by each cell in the respective cluster to remove from the respective cluster those cells that are not antigen-specific for the first immunogenic feature.

20. The method of claim 1, the method further comprising acquiring the corresponding count of the respective immunogenic feature bound to or presented by each immune cell in the population of cells through flow cytometry, active droplet-sorting microfluidics, mass cytometry, or high-content imaging cytometry.

21. The method of claim 1, wherein
the first immunogenic feature is an epitope associated with cancer, and
the at least 1,000 immune cells are cytotoxic T lymphocytes.

22. The method of claim 21, the method further comprising exposing a subject afflicted with cancer to the unique subset of the population of immune cells that are represented by the first cluster or that are cloned from the unique subset of the population of immune cells represented by the first cluster.

23. The method of claim 1, wherein the population of cells is from a plurality of subjects.

24. A computer system comprising:
one or more processors;
memory; and
one or more programs, wherein the one or more programs are stored in the memory and are configured to be executed by the one or more processors, the one or more programs for identifying cells that are antigen-specific for a first immunogenic feature, the one or more programs comprising instructions for:
A) obtaining, in electronic form, an immunogenic feature-by-cell data structure, at a browser module for the computer system, that comprises, for each respective immune cell in a population of cells, and for each respective immunogenic feature in a set comprising at least 20 immunogenic features, a corresponding count that represents an extent to which the respective immune cell binds to or presents the respective immunogenic feature, wherein:
the set of immunogenic features includes the first immunogenic feature, and
for each respective immunogenic feature in the set of immunogenic features, the population of immune cells includes at least one immune cell that is bound to or presents the respective immunogenic feature;
B) clustering the population of immune cells based on similarity of their corresponding sets of counts across the set of immunogenic features, thereby generating a plurality of clusters, wherein each cluster in the plurality of clusters is a unique subset of the population of immune cells; and
C) for each respective cluster in the plurality of clusters:
obtaining a total number of unique immune cell receptor clonotypes detected within the cluster, based on per-cell experimental measurements from the immunogenic feature-by-cell data structure;
obtaining a total number of immune cell receptor clonotypes detected within the cluster, based on per-cell experimental measurements from the immunogenic feature-by-cell data structure;
determining a quantitative measure of clonal expansion within the cluster from (i) the total number of unique immune cell receptor clonotypes and (ii) the total number of immune cell receptor clonotypes; and
computing a distribution of the counts of the first immunogenic feature bound to or presented by each cell in the respective cluster, based on per-cell experimental measurements of binding or presentation from the immunogenic feature-by-cell data structure; and (D) selecting a first cluster, in the plurality of clusters, as antigen-specific for the first immunogenic feature, based on (i) the measure of clonal expansion, displayed by the browser module, for the first cluster being higher than the measure of clonal expansion of other clusters in the plurality of clusters, and (ii) the distribution, displayed by the browser module, of the corresponding count of the first immunogenic feature for the first cluster indicating that the per cell count of the first immunogenic feature bound to or presented by cells in the first cluster is higher than in cells of other clusters in the plurality of clusters.

25. A computer readable storage medium storing one or more programs, the one or more programs comprising instructions, which when executed by an electronic device with one or more processors and a memory cause the electronic device to identify cells that are antigen-specific for a first immunogenic feature by a method comprising:

A) obtaining, in electronic form, an immunogenic feature-by-cell data structure, at a browser module for the computer system, that comprises, for each respective immune cell in a population of cells comprising at least 1000 immune cells, and for each respective immunogenic feature in a set comprising at least 20 immunogenic features, a corresponding count that represents an extent to which the respective immune cell cells binds to or presents the respective immunogenic feature, wherein:

the set of immunogenic features includes the first immunogenic feature, and for each respective immunogenic feature in the set of immunogenic features, the population of immune cells includes at least one immune cell that is bound to or presents the respective immunogenic feature;

B) clustering the population of immune cells based on similarity of their corresponding sets of counts across the set of immunogenic features, thereby generating a plurality of clusters, wherein each cluster in the plurality of clusters is a unique subset of the population of immune cells; and C) for each respective cluster in the plurality of clusters:

obtaining a total number of unique immune cell receptor clonotypes detected within the cluster, based on per-cell experimental measurements from the immunogenic feature-by-cell data structure;

obtaining a total number of immune cell receptor clonotypes detected within the cluster, based on per-cell experimental measurements from the immunogenic feature-by-cell data structure;

determining a quantitative measure of clonal expansion within the cluster from (i) the total number of unique immune cell receptor clonotypes and (ii) the total number of immune cell receptor clonotypes; and computing a distribution of the counts of the first immunogenic feature bound to or presented by each cell in the respective cluster, based on per-cell experimental measurements of binding or presentation from the immunogenic feature-by-cell data structure; and (D) selecting a first cluster, in the plurality of clusters, as antigen-specific for the first immunogenic feature, based on (i) the measure of clonal expansion, displayed by the browser module, for the first cluster being higher than the measure of clonal expansion of other clusters in the plurality of clusters, and (ii) the distribution, displayed by the browser module, of the corresponding count of the first immunogenic feature for the first cluster indicating that the per cell count of the first immunogenic feature bound to or presented by cells in the first cluster is higher than in cells of other clusters in the plurality of clusters.

* * * * *